United States Patent
Schiemann et al.

(10) Patent No.: US 9,834,541 B2
(45) Date of Patent: Dec. 5, 2017

(54) 2-AMINOPYRIDINE COMPOUNDS

(71) Applicants: Merck Patent GmbH, Darmstadt (DE); CANCER RESEARCH TECHNOLOGY LIMITED, London (GB)

(72) Inventors: Kai Schiemann, Seeheim-Jugenheim (DE); Frank Stieber, Einhausen (DE); Julian Blagg, Surrey (GB); Aurelie Mallinger, Affleville (FR); Dennis Waalboer, Ijmuiden (NL); Christian Rink, Bonn (DE); Simon Ross Crumpler, Herfordshire (GB)

(73) Assignees: CANCER RESEARCH TECHNOLOGY LIMITED, London (GB); MERCK PATENT GMBH, Darmstadt (DE)

( * ) Notice: Subject to any disclaimer, the term of this patent is extended or adjusted under 35 U.S.C. 154(b) by 192 days.

(21) Appl. No.: 14/437,561

(22) PCT Filed: Oct. 2, 2013

(86) PCT No.: PCT/EP2013/002966
§ 371 (c)(1),
(2) Date: Apr. 22, 2015

(87) PCT Pub. No.: WO2014/063778
PCT Pub. Date: May 1, 2014

(65) Prior Publication Data
US 2015/0353548 A1 Dec. 10, 2015

(30) Foreign Application Priority Data
Oct. 27, 2012 (EP) .................... 12006952

(51) Int. Cl.
| | |
|---|---|
| *C07D 471/10* | (2006.01) |
| *A61K 31/444* | (2006.01) |
| *A61K 31/4545* | (2006.01) |
| *C07D 401/04* | (2006.01) |
| *C07D 401/14* | (2006.01) |
| *A61K 31/5377* | (2006.01) |
| *A61K 31/499* | (2006.01) |
| *A61K 31/4709* | (2006.01) |
| *C07D 417/14* | (2006.01) |
| *C07D 491/10* | (2006.01) |
| *C07D 498/10* | (2006.01) |

(52) U.S. Cl.
CPC .......... *C07D 401/14* (2013.01); *A61K 31/444* (2013.01); *A61K 31/4545* (2013.01); *A61K 31/4709* (2013.01); *A61K 31/499* (2013.01); *A61K 31/5377* (2013.01); *C07D 401/04* (2013.01); *C07D 417/14* (2013.01); *C07D 471/10* (2013.01); *C07D 491/10* (2013.01); *C07D 498/10* (2013.01)

(58) Field of Classification Search
CPC ........................... C07D 401/14; A61K 31/444
USPC .......................................................... 546/16
See application file for complete search history.

(56) References Cited

U.S. PATENT DOCUMENTS

| | | | |
|---|---|---|---|
| 8,193,207 | B2 | 6/2012 | Zhuo et al. |
| 8,778,925 | B2 | 7/2014 | McDonald et al. |
| 2007/0129345 | A1 | 6/2007 | Zhuo et al. |
| 2010/0168077 | A1 | 7/2010 | Hannah |
| 2011/0190297 | A1 | 8/2011 | McDonald et al. |
| 2014/0350015 | A1 | 11/2014 | McDonald et al. |

FOREIGN PATENT DOCUMENTS

| | | | |
|---|---|---|---|
| WO | WO 02/24679 | * | 3/2002 |
| WO | 2007067504 | A2 | 6/2007 |
| WO | 2008122378 | A1 | 10/2008 |
| WO | 2010041054 | A1 | 4/2010 |

OTHER PUBLICATIONS

Farhanullah et al 2002 , Synthesis of Aminonicotinonitriles and Diaminopyridines through Base Catalysed Ring transformation of 2H-Pyran-2-ones.*
International Search Report from PCT/EP2013/002966 dated Dec. 13, 2013.

* cited by examiner

*Primary Examiner* — Rita Desai
(74) *Attorney, Agent, or Firm* — Millen White Zelano and Branigan, PC; John Sopp; Csaba Henter

(57) ABSTRACT

The invention provides novel substituted 2-aminopyridine compounds according to Formula (I), their manufacture and use for the treatment of hyperproliferative diseases such as cancer, inflammatory or degenerative diseases.

7 Claims, No Drawings

2-AMINOPYRIDINE COMPOUNDS

FIELD OF THE INVENTION

The invention relates to a series of novel substituted 2-aminopyridine compounds that are useful in the treatment of hyperproliferative diseases such as cancer, as well as inflammatory or degenerative diseases, in mammals. Also encompassed by the present invention is the use of such compounds in the treatment of hyperproliferative, inflammatory or degenerative diseases in mammals, especially humans, and pharmaceutical compositions containing such compounds.

SUMMARY OF THE RELATED ART

Wnt proteins comprise a large family of cysteine-rich secreted ligands that are highly conserved among species. Currently, three different pathways are believed to be activated by Wnt signaling: the canonical Wnt/β-catenin cascade, the noncanonical planar cell polarity pathway, and the Wnt/$Ca^{2+}$ pathway. Of these three, the canonical pathway is best understood and has the highest cancer relevance. Therefore, this project is focusing on canonical Wnt/β-catenin signaling.

In the canonical pathway, β-catenin is the key mediator of Wnt signaling. In the absence of Wnt ligands, a protein complex, that contains Axin, adenomatous polyposis coli (APC), glycogen synthase kinase 3β (GSK3β) and casein kinase 1 (CK1), functions in phosphorylating β-catenin and thereby marking it for destruction via ubiquitination and degradation by the proteasome. Following Wnt binding to a receptor complex composed of members of the Frizzled (Fz) family of seven transmembrane, serpentine receptors and low density lipoprotein receptor-related proteins 5/6 (LRP5/6), Disheveled (Dsh) and Axin are recruited to the plasma membrane. Subsequently, the Axin-APC-GSK3β complex is inhibited, non-phosphorylated β-catenin accumulates in the cytoplasm and then translocates into the nucleus where it regulates target gene expression in combination with members of the DNA-binding T cell factor/lymphoid enhancer factor (TCF/LEF) family. Many different target genes of canonical Wnt/β-catenin signaling have been described (e.g. c-Myc, Cyclin D1, VEGF, survivin) which are involved in cell growth, migration and survival (Logan & Nusse, Annu Rev Cell Dev Biol. 2004; 20:781-810).

The Wnt/β-catenin signaling cascade is frequently over-activated in different tumor types and several proteins of the pathway act as oncogenes or tumor suppressors (Giles et al., Biochim Biophys Acta. 2003 Jun. 5; 1653(1):1-24, van Es et al., Curr Opin Genet Dev. 2003 February; 13(1):28-33).

Most prominently, the tumor suppressor APC is mutated in nearly 60% of all colon cancers. In addition, many colon cancers express mutated β-catenin which cannot be phosphorylated and is therefore stabilized. Furthermore, loss of function mutations of the tumor suppressor Axin have been detected in hepatocellular, lung and colon cancers Thus, interference with Wnt/β-catenin signaling is a conceivable strategy for the treatment of cancer (reviewed in Dihlmann & von Knebel Doeberitz, Int. J. Cancer: 113, 515-524 (2005), Luu et al., Curr Cancer Drug Targets. 2004 December; 4(8):653-71).

WO 2010/041054 discloses a series of chemical compounds which act on the Wnt pathway.

However, as a therapeutic directed to this pathway has yet to be commercialized, a significant unmet medical need still exists, so that further promising Wnt pathway inhibitors have to be identified and developed.

For instance, compound "E60" disclosed on page 73 of WO 2010/041054, while exhibiting promising inhibitory activity (see Table A on page 93), at the same time has a high human hepatic microsomal intrinsic clearance (CLint). This is an unfavourable property for a pharmaceutical active ingredient, as it leads to higher and/or more frequent dosing as compared to compounds with a low CLint.

DESCRIPTION OF THE INVENTION

It is, therefore, the object of the present invention to provide novel Wnt pathway inhibitors useful in the treatment of inflammatory or hyperproliferative diseases, such as cancer in mammals, with superior pharmacological properties both with respect to their activities as well as their solubility, metabolic clearance and bioavailability characteristics.

As a result, this invention provides novel substituted 2-aminopyridine compounds or their stereoisomers or tautomers, or pharmaceutically acceptable salts, that are Wnt pathway inhibitors and useful as medicaments, especially in the treatment of the diseases mentioned above and below.

The compounds are defined by Formula (I):

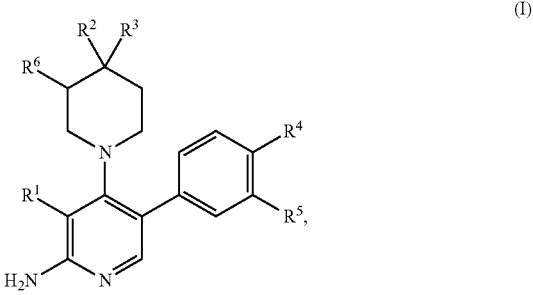

wherein:
$R^1$ is H, LA, Hal, CN, S(LA), CA,
$R^2$ is H, $NH_2$, LA, NH(LA), Hal, X-Cyc,
$R^3$ is LA, Hal, CN, $CONH_2$, CONH(LA)
or
$R^2$, $R^3$ together with the C atom they are attached to, form a 5 or 6 membered aliphatic heterocycle, having 1-3 heteroatoms, selected from O, S and N, which is substituted by 1 or 2 oxo groups, which heterocycle may further be monosubstituted by LA, and which heterocycle may form a condensed ring system with a phenyl or pyridyl group
$R^4$ is H, LA, CONH(LA) or X-Cyc,
$R^5$ is H, F,
or
$R^4$, $R^5$ together with the atoms they are attached to, form a 5 or 6 membered heterocycle, having 1-3 heteroatoms, selected from O, S and N, which is, optionally, independently mono- di- or trisubstituted by oxo, LA, $NH_2$, NH(LA), N(LA)$_2$, HO(LA)-, or which is, optionally, monosubsituted by CA,
$R^6$ is H, LA, OH or F,
Cyc is a 5 or 6 membered monocyclic, aliphatic or aromatic homo- or heterocycle having 1-3 heteroatoms, selected from 0, S and N, which may be mono- or di-substituted by oxo, LA, $NH_2$, NH(LA), N(LA)$_2$, HO(LA)-, or monosubstituted by CA, X is —CH$_2$—, —C$_2$H$_4$—, —NH—, —O—, or a bond,
LA is unbranched or branched alkyl, having 1, 2, 3, 4 or 5 carbon atoms, which may be saturated or partially unsaturated,
wherein 1, 2 or 3H atoms may be replaced by Hal, and/or 1 CH$_2$ group may be replaced by —O—, —NH— or —SO$_2$—, and/or
1 CH group may be replaced by N,
CA is cycloalkyl having 3, 4, 5 or 6 carbon atoms, or cycloalkyl alkyl having 3, 4, 5 or 6 ring carbon atoms and 1 or 2 non-ring carbon atoms, in which cycloalkyl, or cycloalkyl alkyl, 1 CH$_2$ group may be replaced by —O—, or 1 CH group may be replaced by N,
Hal is F, Cl, Br or I.

In general, all residues which occur more than once may be identical or different, i.e. are independent of one another. Above and below, the residues and parameters have the meanings indicated for the Formula (I), unless expressly indicated otherwise. Accordingly, the invention relates, in particular, to the compounds of the Formula (I) in which at least one of the said residues has one of the preferred meanings indicated below.

Hal denotes fluorine, chlorine, bromine or iodine, in particular fluorine, chlorine or bromine.

"LA" denotes for example methyl, ethyl, trifluoromethyl, difluoromethyl, 1,1,1-trifluoroethyl, propyl, isopropyl, methoxyethyl, dimethylaminomethyl, butyl, isobutyl, sec-butyl or tert-butyl, isopropenyl, ethenyl, ethynyl or prop-1-ynyl.

"CA" denotes for example cyclopropyl, (cyclopropyl)methyl, cyclobutyl, (cyclopentyl)ethyl, tetrahydopyranyl, pyrrolidin-1-yl-ethyl, piperidinyl or oxetanyl.

"Cyc" denotes, for example phenyl, oxazolidine-2-, 3-, 4- or 5-yl, isoxazolidine-2-, 3-, 4- or 5-yl, 2,3-dihydro-2-, -3-, -4- or -5-furyl, 2,5-dihydro-2-, -3-, -4- or -5-furyl, tetrahydro-2- or -3-furyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3-, 1-, 5- or 6-piperidinyl, 2-, 3- or 4-morpholinyl, tetrahydro-2-, -3- or -4-pyranyl, hexahydro-1-, -3- or -4-pyridazinyl, hexahydro-1-, -2-, -4- or -5-pyrimidinyl, 1-, 2- or 3-piperazinyl, 2- or 3-furyl, 1-, 2- or 3-pyrrolyl, 1-, 2- or 3-pyrrolidinyl, 1-, 2, 4- or 5-imidazolyl, 1-, 3-, 4- or 5-pyrazolyl, 2-, 3- or 4-pyridyl, 2-, 4-, 5- or 6-pyrimidinyl, pyrazin-2- or 3-yl, pyridazin-3- or 4-yl, 1,2,3-triazol-1-, -4- or -5-yl, 1,2,4-triazol-1-, -3- or 5-yl, 1- or 5-tetrazolyl.

In a preferred embodiment the compounds of the invention conform to Subformulae 1 to 13 of Formulae (I), wherein
in Subformula 1
R$^2$, R$^3$ together with the piperidine ring they are attached to, form (2,8-diaza-spiro[4.5]decan-1-one)-8-yl, (2,8-diaza-spiro[4.5]decane-1,3-dione)-8-yl, (1-oxa-3,8-diaza-spiro[4.5]decan-2-one)-8-yl, (1,3,8-triaza-spiro[4.5]decane-2,4-dione)-8-yl, (1,4,9-triaza-spiro[5.5]undecan-5-one)-9-yl, (4-oxo-1,3,8-triazaspiro[4.5]decan-8-yl,
R$^6$ is H,
in Subformula 2
R$^2$, R$^3$ together with the C atom they are attached to, form 1,3-Dihydro-indol-2-one-3-yl or Aza-1,3-dihydro-indol-2-one-3-yl,
R$^6$ is H,
in Subformula 3
R$^4$ is morpholin-4-yl, piperazin-1-yl, 1H-pyrazol-3-yl, pyridin-3-yl, 1H-pyrazol-4-yl,
each of which may be unsubstituted, or monosubstituted by LA, OH, NH$_2$, HO(LA)- or NH$_2$(LA)-,
R$^5$ is H,
in Subformula 4
R$^4$, R$^5$ together with the phenyl ring they are attached to, form 1H-indazol-5-yl, 1H-indazol-6-yl, 2-oxo-2,3-dihydro-benzooxazol-5-yl, 2-oxo-2,3-dihydro-1H-indol-5-yl, 2-oxo-2,3-dihydro-1H-indol-6-yl, (3,4-dihydro-1H-quinolin-2-one)-6-yl, 1H-indol-6-yl, 2-oxo-2,3-dihydro-1H-indol-6-yl, (3,4-dihydro-1H-quinolin-2-one)-6-yl, 2,2-dioxo-2,3-dihydro-1H-2l6-benzo[c]isothiazol-5-yl, 2,2-dioxo-2,3-dihydro-1H-2l6-benzo[c]isothiazol-6-yl, 1,1-dioxo-2,3-dihydro-1H-1l6-benzo[b]thiophen-5-yl, 1-dioxido-2,3-dihydrobenzo[d]isothiazol-6-yl,
each of which may be unsubstituted, or substituted by LA, OH, NH$_2$, HO(LA)- or NH$_2$(LA)-,
in Subformula 6
R$^1$ is Hal or C(Hal)$_3$,
in Subformula 7
R$^4$ is morpholin-4-yl, 4-methyl-piperazin-1-yl, 1-methyl-1H-pyrazol-3-yl, 6-amino-pyridin-3-yl, 1-(2-hydroxyethyl)-1H-pyrazol-4-yl, 1-methyl-1H-pyrazol-4-yl,
R$^5$ is H,
in Subformula 8
R$^4$, R$^5$ together with the phenyl ring they are attached to, form 1-methyl-1H-indazol-5-yl, 1H-indazol-5-yl, 1-methyl-1H-indazol-6-yl, 1-ethyl-1H-indazol-5-yl, 1-ethyl-1H-indazol-6-yl, 1-isopropyl-1H-indazol-6-yl, 2-oxo-2,3-dihydro-benzooxazol-5-yl, (3H-benzooxazol-2-one)-5-yl, 1-methyl-2-oxo-2,3-dihydro-1H-indol-5-yl, 2-oxo-2,3-dihydro-1H-indol-5-yl, 1-methyl-2-oxo-2,3-dihydro-1H-indol-6-yl, (3,4-dihydro-1H-quinolin-2-one)-6-yl, 1H-indol-6-yl, 2-oxo-2,3-dihydro-1H-indol-6-yl, (1-methyl-3,4-dihydro-1H-quinolin-2-one)-6-yl, 3-amino-1H-indazol-6-yl, 1-methyl-2,2-dioxo-2,3-dihydro-1H-2l6-benzo[c]isothiazol-5-yl, 1-ethyl-2,2-dioxo-2,3-dihydro-1H-2l6-benzo[c]isothiazol-5-yl, 2,2-dioxo-2,3-dihydro-1H-2l6-benzo[c]isothiazol-6-yl, 1,1-dioxo-2,3-dihydro-1H-1l6-benzo[b]thiophen-5-yl, 2-ethyl-1,1-dioxido-2,3-dihydrobenzo[d]isothiazol-6-yl,
in Subformula 9
R$^1$ is F, Cl or CF$_3$,
in Subformula 10
R$^2$, R$^3$ together with the piperidine ring they are attached to, form (2,8-diaza-spiro[4.5]decan-1-one)-8-yl, (1-oxa-3,8-diaza-spiro[4.5]decan-2-one)-8-yl, (1,3,8-triaza-spiro[4.5]decane-2,4-dione)-8-yl,
R$^6$ is H,
in Subformula 11
R$^1$ is F, Cl or CF$_3$,
R$^2$, R$^3$ together with the piperidine ring they are attached to, form (2,8-diaza-spiro[4.5]decan-1-one)-8-yl, (1-oxa-3,8-diaza-spiro[4.5]decan-2-one)-8-yl, (1,3,8-triaza-spiro[4.5]decane-2,4-dione)-8-yl,
R$^6$ is H,
in Subformula 12
R$^2$ is H,
R$^3$ is CN, CONH$_2$,
R$^6$ is H,
in Subformula 13
R$^2$ is H,
R$^3$ is CN,
R$^6$ is OH,
and the remaining residues have the meaning as indicated for Formula (I).

The compounds of the Formula (I) may have one or more centres of chirality. They may accordingly occur in various enantiomeric forms and be in racemic or optically active form. The invention, therefore, also relates to the optically active forms, enantiomers, racemates, diastereomers, collectively: stereoisomers, of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis. In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3. An elegant method for the resolution of racemates containing ester groups (for example acetyl esters) is the use of enzymes, in particular esterases.

It is well known that atoms may have atomic masses or mass numbers which differ from the atomic masses or mass numbers of the atoms which usually occur naturally. Examples of isotopes which are readily commercially available and which can be incorporated into a compound of the present invention by well-known methods include isotopes of hydrogen, carbon, nitrogen, oxygen, phosphorus, fluorine and chlorine, for example $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Incorporation of heavier isotopes, especially deuterium ($^{2}H$), into a compound of the invention has therapeutic advantages owing to the higher metabolic stability of this isotope-labelled compound. Higher metabolic stability translates directly into an increased in vivo half-life or lower dosages. Therefore, these isotopes are included in the definition of atoms H, C, N etc., as used in the chemical compounds of this invention.

The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like. If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials The compounds of the present invention can be in the form of a pharmaceutically acceptable salt, a pharmaceutically acceptable solvate, or a pharmaceutically acceptable solvate of a pharmaceutically acceptable salt.

The term "pharmaceutically acceptable salts" refers to salts prepared from pharmaceutically acceptable bases or acids, including inorganic bases or acids and organic bases or acids. In cases where the compounds of the present invention contain one or more acidic or basic groups, the invention also comprises their corresponding pharmaceutically acceptable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

The term "pharmaceutically acceptable solvates" means addition forms with pharmaceutically acceptable solvents that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, e.g. a mono- or dihydrate. If the solvent is alcohol, the solvate formed is an alcoholate, e.g., a methanolate or ethanolate. If the solvent is an ether, the solvate formed is an etherate, e.g., diethyl etherate.

Therefore, the following items are also in accordance with the invention:
a) all stereoisomers or tautomers of the compounds, including mixtures thereof in all ratios,
b) prodrugs of the compounds, or stereoisomers or tautomers of these prodrugs,
c) pharmaceutically acceptable salts of the compounds and of the items mentioned under (a) and (b),
d) pharmaceutically acceptable solvates of the compounds and of the items mentioned under (a), (b) and (c).

It should be understood that all references to compounds above and below are meant to include these items, in particular pharmaceutically acceptable solvates of the compounds, or pharmaceutically acceptable solvates of their pharmaceutically acceptable salts.

Furthermore, the present invention relates to pharmaceutical compositions comprising a compound of the present invention, or its stereoisomers or tautomers, or pharmaceutically acceptable salts of each of the foregoing, including mixtures thereof in all ratios, as active ingredient, together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or other Wnt pathway inhibitors.

The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, colon, epidermoid, squamous cell, bladder, gastric, pancreatic, breast, head & neck, renal, kidney, liver, ovarian, prostate, uterine, oesophageal, testicular, gynecological, thyroid cancer, melanoma, as well as hematologic malignancies such as acute myelogenous leukemia, multiple myeloma, chronic myelogneous leukemia, myeloid cell leukemia, Kaposi's sarcoma, or any other type of solid or liquid tumors. Preferably, the cancer to be treated is chosen from colon, lung, breast and hematological tumor types.

In addition, said compounds and pharmaceutical composition are for the treatment of inflammatory diseases such as multiple sclerosis, rheumatoid arthritis, systemic lupus, inflammatory bowel diseases or degenerative diseases such as osteoarthritis and Alzheimer's disease.

This invention also relates to a compound or pharmaceutical composition for inhibiting abnormal cell growth in a mammal which comprises an amount of a compound of the present invention, in combination with an amount of another anti-cancer therapeutic, wherein the amounts of the compound, and of the other anti-cancer therapeutic are together effective in inhibiting abnormal cell growth. Many anti-cancer therapeutics are presently known in the art. In one embodiment, the anti-cancer therapeutic is selected from the following groups of agents:

Alkylating agents such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302, VAL-083.

Platinum Compounds such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin.

DNA altering agents such as amrubicin, bisantrene, decitabine, mitoxantrone, procarbazine, trabectedin, clofarabine; amsacrine, brostallicin, pixantrone, laromustine.

Topoisomerase Inhibitors such as etoposide, irinotecan, razoxane, sobuzoxane, teniposide, topotecan; amonafide, belotecan, elliptinium acetate, voreloxin.

Microtubule modifiers such as cabazitaxel, docetaxel, eribulin, ixabepilone, paclitaxel, vinblastine, vincristine, vinorelbine, vindesine, vinflunine; fosbretabulin, tesetaxel.

Antimetabolites such as asparaginase, azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur, trimetrexate;

Anticancer antibiotics such as bleomycin, dactinomycin, doxorubicin, epirubicin, idarubicin, levamisole, miltefosine, mitomycin C, romidepsin, streptozocin, valrubicin, zinostatin, zorubicin, daunorubicin, plicamycin; aclarubicin, peplomycin, pirarubicin.

Hormones/Antagonists such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide.

Aromatase inhibitors such as aminoglutethimide, anastrozole, exemestane, fadrozole, letrozole, testolactone; formestane.

Small molecule kinase inhibitors such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate, ibrutinib, icotinib, buparlisib, cipatinib, cobimetinib, idelalisib, fedratinib, XL-647.

Photosensitizers such as methoxsalen; porfimer sodium, talaporfin, temoporfin;

Antibodies such as alemtuzumab, besilesomab, brentuximab vedotin, cetuximab, denosumab, ipilimumab, ofatumumab, panitumumab, rituximab, tositumomab, trastuzumab, bevacizumab, pertuzumab; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab, onartuzumab, racotumomab, tabalumab, EMD-525797, nivolumab.

Cytokines such as aldesleukin, interferon alfa[2], interferon alfa2a[3], interferon alfa2b; celmoleukin, tasonermin, teceleukin, oprelvekin[1,3], recombinant interferon beta-1a.

Drug Conjugates such as denileukin diftitox, ibritumomab tiuxetan, iobenguane 1123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab, vintafolide.

Vaccines such as sipuleucel; vitespen, emepepimut-S, oncoVAX, rindopepimut[3], troVax, MGN-1601, MGN-1703.

Miscellaneous: alitretinoin, bexarotene, bortezomib, everolimus, ibandronic acid, imiquimod, lenalidomide, lentinan, metirosine, mifamurtide, pamidronic acid, pegaspargase, pentostatin, sipuleucel, sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine, picibanil, reolysin, retaspimycin hydrochloride, trebananib, virulizin, carfilzomib, endostatin, immucothel, belinostat, MGN-1703.

This invention further relates to a method for inhibiting abnormal cell growth in a mammal or treating a hyperproliferative disorder that comprises administering to the mammal an amount of a compound of the present invention or pharmaceutical composition, in combination with radiation therapy, wherein the amounts of the compound or pharmaceutical composition, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of a compound of the invention, or pharmaceutical composition, in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention or pharmaceutical composition, which amount is effective in sensitizing abnormal cells to treatment with radiation. The amount of the compound in this method can be determined according to the means for ascertaining effective amounts of such compounds described herein.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating inflammatory, degenerative or hyperproliferative diseases for which compounds of the present invention are indicated, generally satisfactory results are obtained when the compounds of the present invention are administered at a daily dosage of from about 0.01 milligram to about 100 milligram per kilogram of body weight, preferably given as a single daily dose. For most large mammals, the total daily dosage is from about 0.1 milligrams to about 1000 milligrams, preferably from about 0.2 milligram to about 50 milligrams. In the case of a 70 kg adult human, the total daily dose will generally be from about 0.2 milligrams to about 200 milligrams. This dosage regimen may be adjusted to provide the optimal therapeutic response.

The invention also relates to a set (kit) consisting of separate packs of
a) an effective amount of a compound according to the invention or its stereoisomers or tautomers, or pharmaceutically acceptable salts of each of the foregoing, including mixtures thereof in all ratios, and
b) an effective amount of a further medicament active ingredient.

The set comprises suitable containers, such as boxes, individual bottles, bags or ampoules.

By way of example, the set may comprise separate ampoules, each containing an effective amount of a compound according to the invention, and an effective amount of a further medicament active ingredient in dissolved or lyophilised form.

EXPERIMENTAL SECTION

Some abbreviations that may appear in this application are as follows:

ABBREVIATIONS

| Designation | |
|---|---|
| aq. | Aqueous |
| ATP | Adenosine triphosphate |
| b | Broad peak |
| Boc | tert-Butyl carbamate |
| Boc₂O | Di-tert-butyl dicarbonate |
| calc | Calculated |
| cHex | Cyclohexane |
| CDCl₃ | Deutero-Chloroforme |
| d | Doublet |
| dba | Dibenzylidene acetone |
| DCM | Dichloromethane |
| DME | Ethylene glycol dimethylether |
| DMF | Dimethylformamide |
| DMSO | Dimethyl sulfoxide |
| dppf | Bis(diphenylphosphino)ferrocene |
| EtOAc | Ethyl acetate |
| EtOH | Ethanol |
| ESI | Electrospray ionisation |
| h | Hour |
| HPLC | High Pressure Liquid Chromatography |
| HRMS | High resolution mass spectrometry |
| LC/MS | Liquid Chromatography coupled to Mass Spectrometry |
| m | Multiplet |
| m/z | Mass-to-charge ratio |
| min | Minute |
| MS | Mass spectrometry |
| N | Normal (unit of concentration) |
| nd | Not determined |
| NMP | N-Methyl-2-pyrrolidinone |
| NMR, 1H | Nuclear Magnetic Resonance, proton |
| PMB | Para methoxy benzyl |
| q | Quartette (or quartet) |
| Rf | Retention factor |
| RT | Room temperature |
| Rt | Retention time |
| s | Singlet |
| sat. | Saturated |
| t | Triplet |
| tert | Tertiary |
| TFA | Trifluoro acetic acid |
| THF | Tetrahydrofuran |
| UV | Ultraviolet |
| Xphos | 2-Dicyclohexylphosphino-2',4',6'-triisopropylbiphenyl |

The compounds of the present invention can be prepared according to the procedures of the following Schemes and Examples, using appropriate materials and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

The invention will be illustrated, but not limited, by reference to the specific embodiments described in the following examples. Unless otherwise indicated in the schemes, the variables have the same meaning as described above.

Unless otherwise specified, all starting materials are obtained from commercial suppliers and used without further purifications. Unless otherwise specified, all temperatures are expressed in ° C. and all reactions are conducted at RT. Compounds were purified by either silica chromatography or preparative HPLC.

The present invention relates also to a process for the manufacture of compounds of Formula (I), wherein a compound of Formula (V)

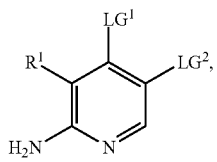

is reacted with a compound of Formula (IV)

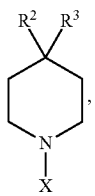

to yield a compound of Formula (III)

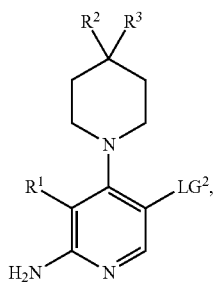

which is then further reacted with a compound of Formula (II)

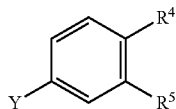

to yield a compound of Formula (I).

$LG^1$ is a leaving group typically used in nucleophilic aromatic substitutions, preferably Hal, such as F, Cl or Br. $LG^2$ is a reactive group capable of reacting in metal-catalyst reactions (e.g. Suzuki reaction), such as Cl, Br or I.

X is H, or a typical amine protecting group such as BOC, which is cleaved off under the reaction conditions. Y is a boronic acid or a boronic ester.

Examples

HPLC Method (A)
  Solvent A: water+0.1% trifluoroacetic acid
  Solvent B: acetonitrile+0.1% trifluoroacetic acid
  Flow: 2 mL/min, wave length: 220 nm
  Gradient:
  0.0 min 1% B
  0.2 min 1% B
  3.8 min 100% B
  4.2 min 100% B
  Column: Chromolith Speed ROD RP-18e 100-3.0 mm (Merck KGaA)
HPLC Method (B)
  Solvent A: water+0.1% formic acid
  Solvent B: methanol+0.1% formic acid
  Flow: 1.5 mL/min, wave length: 254 nm
  Gradient:
  0.0 min 10% B
  2.5 min 90% B
  3.5 min 90% B
  3.8 min 10% B
  4.0 min 10% B
  Column: Purospher STAR RP-18e 30×4 mm (Merck KGaA)
HPLC Method (C)
  Solvent A: water+0.1% formic acid
  Solvent B: methanol+0.1% formic acid
  Flow: 1.5 mL/min, wave length: 220 nm
  Gradient:
  0.0 min 10% B
  2.5 min 90% B
  3.5 min 90% B
  3.8 min 10% B
  4.0 min 10% B
  Column: Purospher STAR RP-18e 30×4 mm (Merck KGaA)
HPLC Method (D)
  Solvent A: water+0.05% formic acid
  Solvent B: acetonitrile+0.04% formic acid
  Flow: 2 mL/min, wave length: 220 nm
  Gradient:
  0.0 min 4% B
  2.8 min 100% B
  3.3 min 100% B
  Column: Chromolith Performance RP18e 100-3

The working examples presented below are intended to illustrate particular embodiments of the invention, and are not intended to limit the scope of the specification or the claims in any way.

Chemical Synthesis

In this section experimental details are provided for a number of Example compounds according to Formula (I), and synthetic intermediates thereof.

1. 8-(2-Amino-3-chloro-5-phenyl)pyridin-4-yl)-2,8-diazaspiro[4.5]decan-1-one derivatives (22, 7, 16)

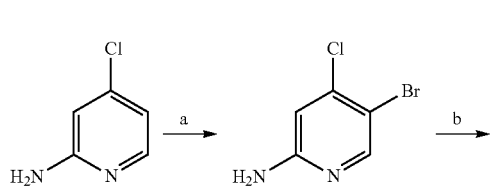

-continued

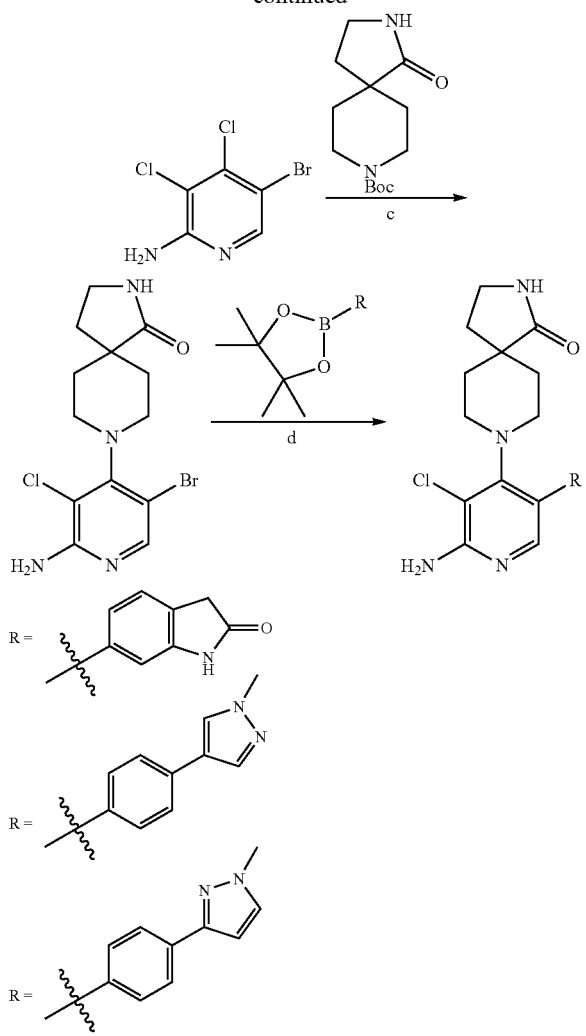

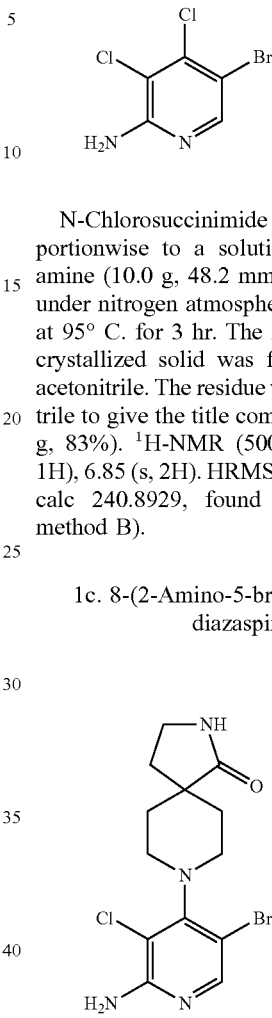

1a. 5-Bromo-4-chloropyridin-2-amine

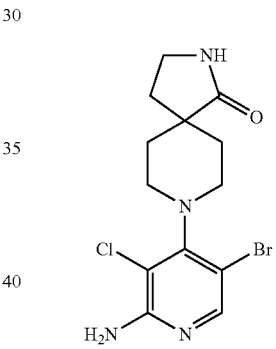

N-Bromosuccinimide (10.9 g, 61.3 mmol) was added to a solution of 4-chloro-2-amino-pyridine (7.50 g, 58.3 mmol) in acetonitrile (130 mL) at RT under nitrogen atmosphere. The yellow solution was stirred for 3 hr. The solvent was evaporated under reduced pressure and the residue purified by chromatography on silica gel (cyclohexane/ethyl acetate) to give the title compound as a light yellow solid (10.0 g, 83%). $^1$H-NMR (500 MHz, CDCl$_3$) ppm=8.16 (s, 1H), 6.62 (s, 1H), 4.57 (bs, 2H). HRMS m/z (ESI$^+$) [M+H]$^+$ C$_5$H$_5$BrClN$_2$, calc 208.9297, found 208.9297, Rt=2.96 min (HPLC method B).

1b. 5-Bromo-3,4-dichloropyridin-2-amine

N-Chlorosuccinimide (6.11 g, 45.8 mmol) was added portionwise to a solution of 5-bromo-4-chloropyridin-2-amine (10.0 g, 48.2 mmol) in acetonitrile (180 mL) at RT under nitrogen atmosphere and the reaction mixture stirred at 95° C. for 3 hr. The mixture was cooled to RT and the crystallized solid was filtered off and washed with cold acetonitrile. The residue was recrystallized from hot acetonitrile to give the title compound as a light brown solid (10.0 g, 83%). $^1$H-NMR (500 MHz, DMSO-d6) ppm=8.13 (s, 1H), 6.85 (s, 2H). HRMS m/z (ESI$^+$) [M+H]$^+$ C$_5$H$_4$BrCl$_2$N$_2$, calc 240.8929, found 240.8928, Rt=2.96 min (HPLC method B).

1c. 8-(2-Amino-5-bromo-3-chloropyridin-4-yl)-2,8-diazaspiro[4.5]decan-1-one

5-Bromo-3,4-dichloropyridin-2-amine (300 mg, 1.24 mmol), 8-boc-2,8-diaza-spiro-[4.5]decan-1-one (347 mg, 1.36 mmol) and potassium fluoride (144 mg, 2.48 mmol) were loaded in a microwave vial. The capped vial was evacuated using high vacuum and purged with nitrogen (each three times). Triethylamine (0.48 mL, 3.72 mmol) and NMP (3 mL) were added and the mixture was degassed using high vacuum and purged with nitrogen three times. The reaction mixture was heated in the microwave at 220° C. for 2 hr, cooled and then ethyl acetate and water were added and the organic layer was separated. The aqueous layer was extracted twice with ethyl acetate. The combined organic layers were dried over MgSO$_4$, filtered and the solvent was evaporated under reduced pressure. The resulting precipitate was purified by chromatography on silica gel (dichloromethane/ethanol) to give the title compound as a white solid containing 5% of NMP (260 mg, 60%). $^1$H-NMR (500 MHz, DMSO-d6) ppm=7.92 (s, 1H), 7.59 (s, 1H), 6.34 (bs, 2H), 3.27-2.99 (m, 6H), 2.01 (t, J=6.8, 2H), 1.93-1.79 (m, 2H), 1.43-1.37 (m, 2H). HRMS m/z (ESI$^+$) [M+H]$^+$ C$_{13}$H$_{17}$BrClN$_4$O, calc 359.0269, found 359.0268, Rt=2.05 min (HPLC method B).

1d1. 8-(2-Amino-3-chloro-5-(4-(1-methyl-1H-pyrazol-3-yl)phenyl)pyridin-4-yl)-2,8-diazaspiro[4.5]decan-1-one (22)

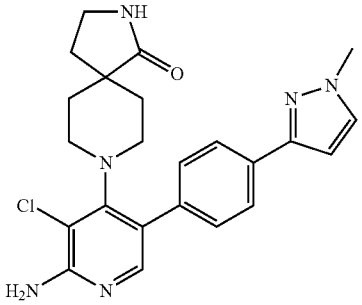 [SMILES: Cn1ccc(-c2ccc(-c3cnc(N)c(Cl)c3N3CCC4(CCNC4=O)CC3)cc2)n1]

8-(2-Amino-5-bromo-3-chloropyridin-4-yl)-2,8-diazaspiro[4.5]decan-1-one (30.0 mg, 0.083 mmol), 1-methyl-3-(4-(4,4,5,5-tetramethyl-1,3,2-dioxaborolan-2-yl)phenyl)-1H-pyrazole (23.7 mg, 0.083 mmol) and Pd(dppf)Cl$_2$.CH$_2$Cl$_2$ (3.05 mg, 4.17 μmol) were loaded in a microwave vial. The capped vial was evacuated using high vacuum and purged with nitrogen (each three times). Acetonitrile (0.7 mL) and aqueous sodium carbonate (0.5M, 0.23 mL, 0.12 mmol) were added and the mixture was degassed again by using the high vacuum and purged with nitrogen again (each three times). The mixture was heated in the microwave at 120° C. for 1 h before it was transferred into a flask with the help of chloroform/methanol and the water was evaporated by azeotropic removal with toluene twice. The resulting residue was purified by chromatography on silica gel (dichloromethane/ethanol), further purified by prep. HPLC (Gilson, acetonitrile/water) and recrystallized from ethyl acetate to give the title compound as a white solid (6.00 mg, 16%). $^1$H-NMR (500 MHz, DMSO-d6) ppm=7.82 (d, J=8.2, 2H), 7.74 (d, J=2.2, 1H), 7.66 (s, 1H), 7.50 (s, 1H), 7.27 (d, J=8.2, 2H), 6.72 (d, J=2.2, 1H), 6.13 (s, 2H), 3.89 (s, 3H), 3.10 (t, J=6.8, 2H), 2.96 (d, J=12.4, 2H), 2.74-2.61 (m, 2H), 1.81 (t, J=6.8, 2H), 1.75-1.63 (m, 2H), 1.25-1.12 (m, 2H). HRMS m/z (ESI$^+$) [M+H]$^+$ C$_{23}$H$_{26}$ClN$_6$O, calc 437.1851, found 437.1838, Rt=2.00 min (HPLC method B).

1d2. 6-(6-Amino-5-chloro-4-(1-oxo-2,8-diazaspiro[4.5]decan-8-yl)pyridin-3-yl)indolin-2-one (7)

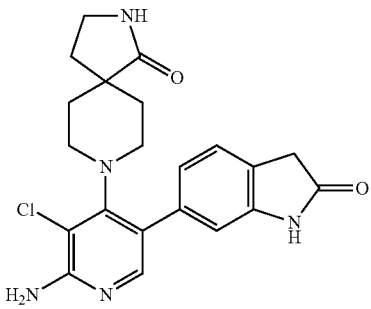 [SMILES: Nc1ncc(-c2ccc3c(c2)NC(=O)C3)c(N2CCC3(CCNC3=O)CC2)c1Cl]

8-(2-Amino-5-bromo-3-chloropyridin-4-yl)-2,8-diazaspiro[4.5]decan-1-one (15.0 mg, 0.042 mmol), 6-(4,4,5,5-tetramethyl-1,3,2-dioxaborolan-2-yl)indolin-2-one (11.9 mg, 0.046 mmol) and tetrakis(triphenylphosphine)palladium(0) (2.41 mg, 2.09 μmol) were loaded in a microwave vial. The capped vial was evacuated using high vacuum and purged with nitrogen (each three times). Acetonitrile (0.4 mL) and aqueous sodium carbonate (0.5M, 0.18 mL, 0.058 mmol) were added and the mixture was degassed using high vacuum and purged with nitrogen again three times. The mixture was heated in the microwave at 120° C. for 1 h before it was transferred into a flask with the help of chloroform/methanol and the water was evaporated by azeotropic removal with toluene twice. The resulting residue was purified by chromatography on silica gel (dichloromethane/ethanol) and recrystallization from ethyl acetate/diethyl ether to give the title compound as a white solid (6.0 mg, 35%). $^1$H-NMR (500 MHz, DMSO-d6) ppm=10.39 (s, 1H), 7.61 (s, 1H), 7.52 (s, 1H), 7.23 (d, J=7.6, 1H), 6.81 (dd, J=7.5, 1.3, 1H), 6.68 (s, 1H), 6.11 (s, 2H), 3.51 (s, 2H), 3.12 (t, J=6.8, 2H), 2.95 (d, J=12.6, 2H), 2.65 (d, J=9.8, 2H), 1.82 (t, J=6.8, 2H), 1.71 (td, J=12.6, 3.6, 2H), 1.23 (d, J=12.6, 2H). HRMS m/z (ESI$^+$) [M+H]$^+$ C$_{21}$H$_{23}$ClN$_5$O$_2$, calc 412.1535, found 412.1526, Rt=1.72 min (HPLC method B).

1d3. 8-(2-Amino-3-chloro-5-(4-(1-methyl-1H-pyrazol-4-yl)phenyl)pyridin-4-yl)-2,8-diazaspiro[4.5]decan-1-one (16)

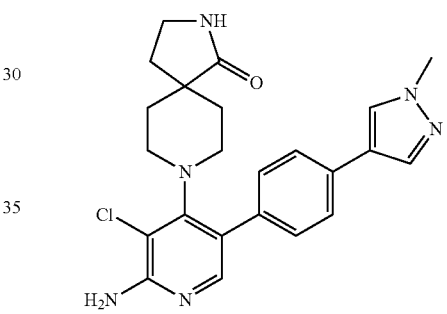

8-(2-Amino-5-bromo-3-chloropyridin-4-yl)-2,8-diazaspiro[4.5]decan-1-one (30.0 mg, 0.083 mmol), 1-methyl-4-(4-(4,4,5,5-tetramethyl-1,3,2-dioxaborolan-2-yl)phenyl)-1H-pyrazole (24.9 mg, 0.088 mmol) and tetrakis(triphenylphosphine)palladium(0) (4.82 mg, 4.17 μmol) were loaded in a microwave vial. The capped vial was evacuated using high vacuum and purged with nitrogen (each three times). Acetonitrile (0.77 mL) and sodium carbonate (0.5M, 0.23 mL, 0.117 mmol) were added and the mixture was degassed using high vacuum and purged with nitrogen three times. The mixture was heated in the microwave at 120° C. for 1 h before it was cooled and transferred into a flask with the help of chloroform/methanol and the water was evaporated by azeotropic removal with toluene twice. The resulting residue was purified by chromatography on silica gel (dichloromethane/ethanol) followed by further purification by using a SCX$_2$-cartridge (eluting with dichloromethane/1N NH$_3$ in methanol). Recrystallization from ethyl acetate/diethyl ether give the title compound as a white solid (10.0 mg, 27%). $^1$H-NMR (500 MHz, DMSO-d6) ppm=8.17 (s, 1H), 7.89 (d, J=0.6, 1H), 7.64 (s, 1H), 7.60 (d, J=8.3, 2H), 7.50 (s, 1H), 7.23 (d, J=8.2, 2H), 6.11 (s, 2H), 3.87 (s, 3H), 3.10 (t, J=6.8, 2H), 3.01-2.91 (m, 2H), 2.73-2.60 (m 2H), 1.76-1.63 (m, 2H), 1.81 (t, J=6.8, 2H). HRMS m/z (ESI$^+$) [M+H]$^+$ C$_{23}$H$_{26}$ClN$_6$O, calc 437.1851, found 437.1862, Rt=1.98 min (HPLC method B).

An alternative approach is to protect the 2-amino function of the pyridine during the displacement reactions.

2. 8-[2-Amino-3-chloro-5-(1-methyl-1H-indazol-5-yl)-pyridin-4-yl]-2,8-diaza-spiro[4.5]decan-1-one (25)

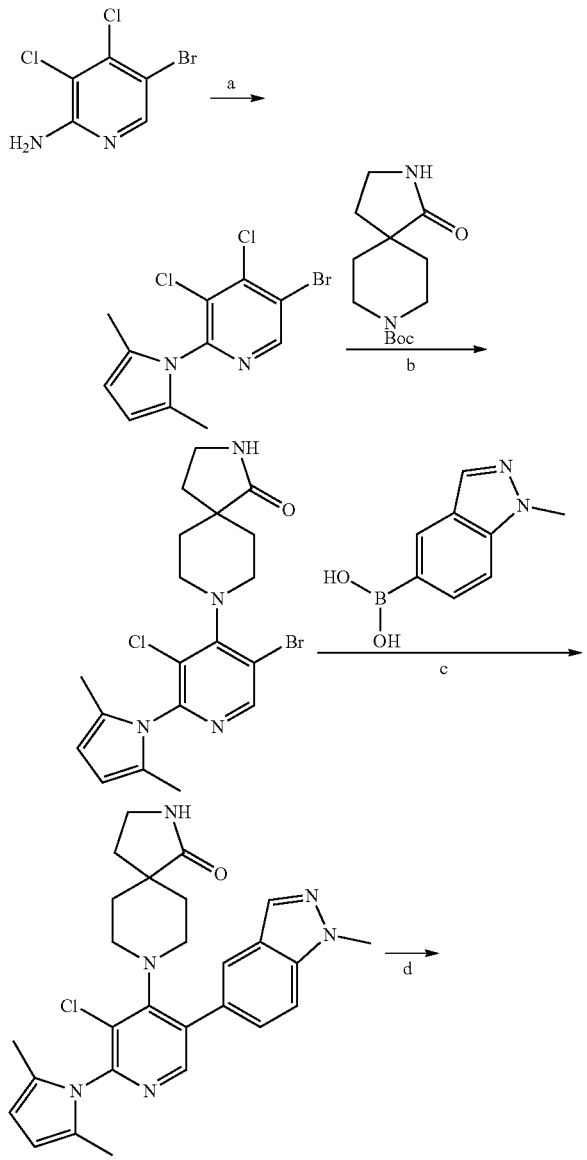

2a. 5-Bromo-3,4-dichloro-2-(2,5-dimethyl-1H-pyrrol-1-yl)pyridine

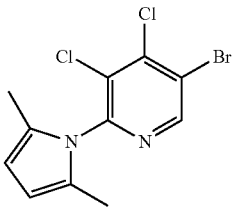 [SMILES: Cc1ccc(C)n1-c1ncc(Br)c(Cl)c1Cl]

A solution of 5-bromo-3,4-dichloropyridin-2-amine (500 mg, 2.07 mmol), acetyl acetone (0.27 mL, 2.27 mmol) and p-toluene sulfonic acid monohydrate (39.3 mg, 0.21 mmol) in toluene (3.5 mL) was stirred at reflux for 5 hr. The mixture was cooled to RT and the solvent evaporated under reduced pressure. The residue was dissolved in ethyl acetate and washed with brine, dried over $MgSO_4$, filtered and the solvent was evaporated under reduced pressure. The resulting brown oil was purified by chromatography on silica gel (cyclohexane/ethyl acetate) to give the title compound as a light brown oil (360 mg, 55%). $^1$H-NMR (500 MHz, $CDCl_3$) ppm=8.69 (s, 1H), 5.95 (s, 2H), 2.02 (s, 6H). HRMS m/z (ESI$^+$) [M+H]$^+$ $C_{11}H_{10}BrCl_2N_2$, calc 318.9399, found 318.9384, Rt=3.40 min (HPLC method B).

2b. 8-(5-Bromo-3-chloro-2-(2,5-dimethyl-1H-pyrrol-1-yl)pyridin-4-yl)-2,8-diazaspiro[4.5]decan-1-one 5-Bromo-3,4-dichloro-2-(2,5-dimethyl-1H-pyrrol-1-yl)pyridine (225 mg, 0.70 mmol) and 8-boc-2,8-diaza-spiro-[4.5]decan-1-one (197 mg, 0.77 mmol) were loaded in a microwave vial. The capped vial was evacuated using high vacuum and purged with nitrogen (each three times). Triethylamine (0.27 mL, 2.11 mmol) and NMP (2.3 mL) were added and the mixture was degassed by using the high vacuum and purged with nitrogen three times. The reaction mixture was heated in the microwave at 220° C. for 1 h before it was cooled and dropped in vigorously stirred water (8 mL). The resulting precipitate was filtered off and the residue was purified by chromatography on silica gel (dichloromethane/ethanol) to give the title compound as a light brown solid (153 mg, 50%). $^1$H-NMR (500 MHz, $CDCl_3$) ppm=8.47 (s, 1H), 6.53 (bs, 1H), 5.90 (s, 2H), 3.52-3.32 (m, 6H), 2.25-2.10 (m, 4H), 2.01 (s, 6H), 1.58 (d, J=13.0, 2H).

HRMS m/z (ESI⁺) [M+H]⁺ C₁₉H₂₂BrClN₄O, calc 437.0738, found 437.0733, Rt=3.05 min (HPLC method B).

2c. 8-(3-Chloro-2-(2,5-dimethyl-1H-pyrrol-1-yl)-5-(1-methyl-1H-indazol-5-yl)pyridin-4-yl)-2,8-diazaspiro[4.5]decan-1-one

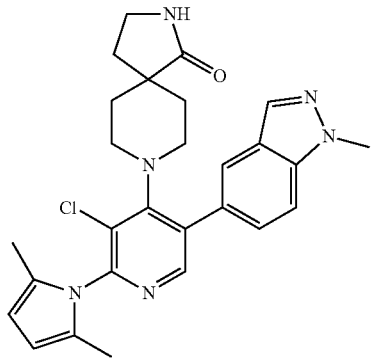 [SMILES: Cc1ccc(C)n1-c1ncc(-c2ccc3c(cnn3C)c2)c(N2CCC3(CCNC3=O)CC2)c1Cl]

8-(5-Bromo-3-chloro-2-(2,5-dimethyl-1H-pyrrol-1-yl)pyridin-4-yl)-2,8-diazaspiro[4.5]decan-1-one (140 mg, 0.32 mmol), 1-methyl-1H-indazole-5-boronic acid (61.9 mg, 0.35 mmol) and Pd(dppf)Cl₂.CH₂Cl₂ (11.7 mg, 0.016 mmol) were loaded in a microwave vial. The capped vial was evacuated using high vacuum and purged with nitrogen (each three times). Acetonitrile (3 mL) and aqueous sodium carbonate (0.5M, 0.895 mL, 0.448 mmol) were added and the mixture was degassed again by using the high vacuum and purged with nitrogen again (each three times). The mixture was heated in the microwave at 120° C. for 1 h before it was transferred into a flask with the help of chloroform/methanol and the water was evaporated by azeotropic removal with toluene twice. The resulting residue was purified by chromatography on silica gel (dichloromethan/ethanol) to give the title compound as a light brown solid (126 mg, 81%). ¹H-NMR (500 MHz, CDCl₃) ppm=8.27 (s, 1H), 8.08 (s, 1H), 7.74 (s, 1H), 7.54 (d, J=8.6, 1H), 7.41 (d, J=8.6, 1H), 6.17 (bs, 1H), 5.94 (s, 2H), 4.16 (s, 3H), 3.31-3.20 (m, 4H), 2.78 (s, 2H), 2.10 (s, 6H), 1.99-1.91 (m, 4H), 1.36 (d, J=13.2, 2H). HRMS m/z (ESI⁺) [M+H]⁺ C₂₇H₃₀ClN₆O, calc 489.2164, found 489.2157, Rt=3.01 min (HPLC method B).

2d. 8-(2-Amino-3-chloro-5-(1-methyl-1H-indazol-5-yl)pyridin-4-yl)-2,8-diazaspiro[4.5]decan-1-one (25)

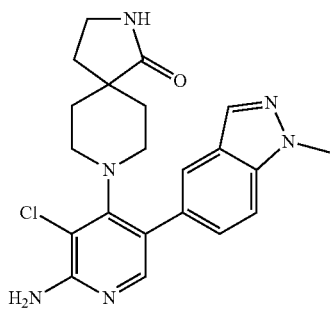 [SMILES: Cn1ncc2cc(-c3cnc(N)c(Cl)c3N3CCC4(CCNC4=O)CC3)ccc21]

A suspension of 8-(3-chloro-2-(2,5-dimethyl-1H-pyrrol-1-yl)-5-(1-methyl-1H-indazol-5-yl)pyridin-4-yl)-2,8-diazaspiro[4.5]decan-1-one (50.0 mg, 0.102 mmol) and hydroxylamine hydrochloride (249 mg, 3.58 mmol) in ethanol (0.6 mL) and water (0.3 mL) was stirred at reflux for 8 h. The mixture was cooled to RT before dichloromethane and saturated Na₂CO₃ solution were added and the organic layer was separated. The aqueous layer was extracted twice with dichloromethane. The combined organic layers were dried over MgSO₄, filtered and the solvent was evaporated under reduced pressure. The residue was purified by chromatography on silica gel (dichloromethane/ethanol) and further purified by using a SCX₂-cartridge (eluting with dichloromethane/1N NH₃ in methanol) to give the title compound as a white solid (10.0 mg, 24%). ¹H-NMR (500 MHz, DMSO-d6) ppm=8.06 (s, 1H), 7.68-7.64 (m, 2H), 7.48 (s, 1H), 7.27 (dd, J=8.7, 1.6, 1H), 6.09 (bs, 2H), 4.07 (s, 3H), 3.07 (t, J=6.8, 2H), 3.01-2.92 (m, 2H), 2.70-2.55 (m, 2H), 1.75 (t, J=6.8, 2H), 1.71-1.59 (m, 2H), 1.20-1.12 (m, 2H). HRMS m/z (ESI⁺) [M+H]⁺ C₂₁H₂₃ClN₆O, calc 411.1695, found 411.1692, Rt=1.78 min (HPLC method B).

The 2-amino function of the pyridine can also be protected as the bis(4-methoxybenzyl) derivative instead of the 2,5-dimethyl-pyrrolo derivative.

3. 8-(2-Amino-3-chloro-5-(4-(1-methyl-1H-pyrazol-4-yl)phenyl)pyridin-4-yl)-2,8-diazaspiro[4.5]decane-1,3-dione (38) and 8-[2-Amino-3-chloro-5-(1-methyl-1H-indazol-5-yl)-pyridin-4-yl]-2,8-diazaspiro[4.5]decan-1-one (25)

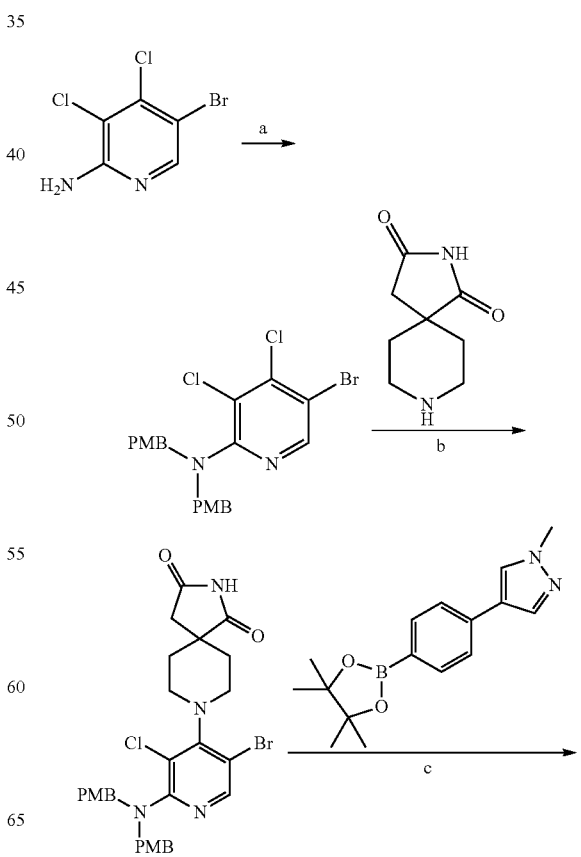

-continued

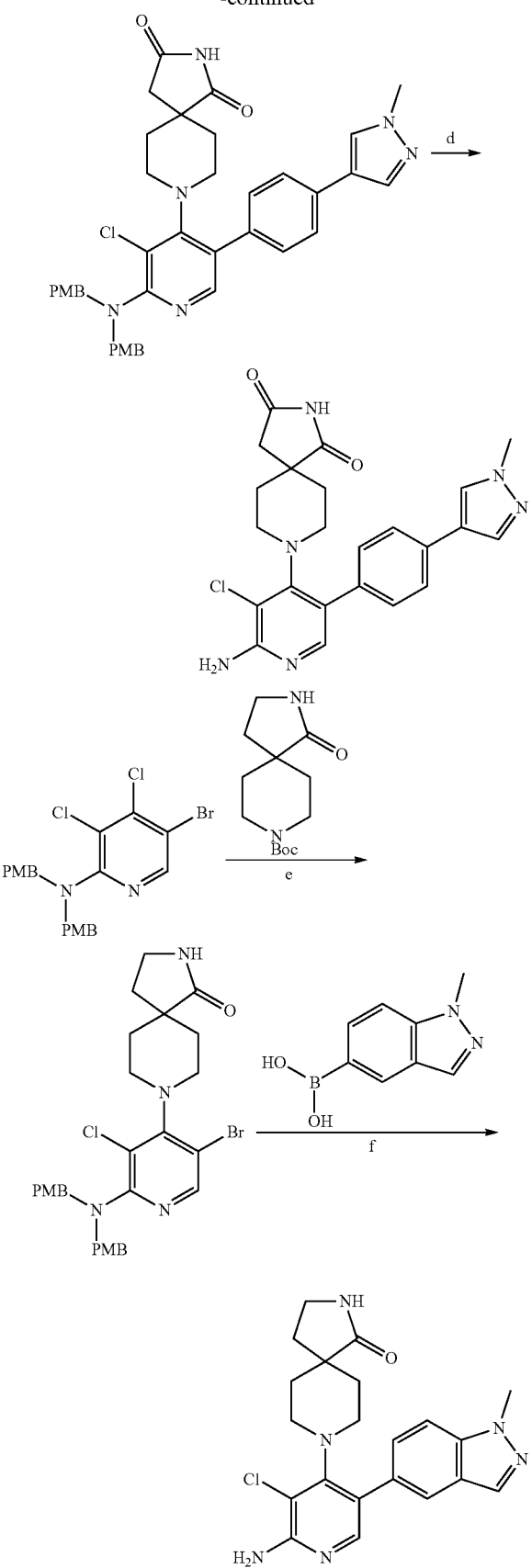

3a. 5-Bromo-3,4-dichloro-N,N-bis(4-methoxybenzyl)pyridin-2-amine

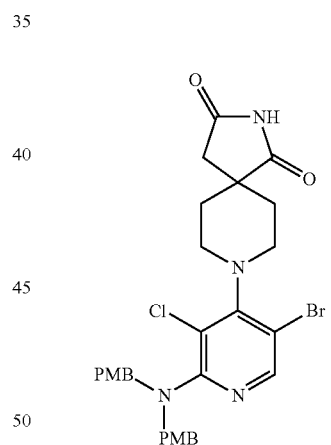

5-Bromo-3,4-dichloro-pyridin-2-ylamine (7.50 g, 31.0 mmol) was dissolved in DMF (75 mL) and 4-methoxybenzyl chloride (12.4 g, 77.5 mmol) was added. Under stirring, sodium hydride (3.70 g, 93.0 mmol, 60% solution in paraffin oil) was added slowly and the mixture was stirred 2 h at RT. 600 mL sat. NaHCO$_3$ solution was added and the mixture was extracted twice with dichloromethane (300 mL). The organic layers were combined, washed with brine, dried and evaporated. The residue was purified using flash chromatography (petrol ether/ethyl acetate) to obtain an off-white solid (12.5 g, 25.9 mmol, 84%). $^1$H-NMR (500 MHz, CDCl$_3$) ppm=8.26 (s, 1H), 7.20 (d, J=8.6, 4H), 6.85 (d, J=8.7, 4H), 4.42 (s, 4H), 3.81 (s, 6H). HRMS m/z (ESI$^+$) [M+H-PMB]$_+$ C$_{13}$H$_{12}$BrCl$_2$N$_2$O, calc 360.9505, found 360.9492, Rt=3.51 min (HPLC method B).

3b. 8-(2-(Bis(4-methoxybenzyl)amino)-5-bromo-3-chloropyridin-4-yl)-2,8-diazaspiro[4.5]decane-1,3-dione 5-Bromo-3,4-dichloro-N,N-bis(4-methoxybenzyl)pyridin-2-amine (200 mg, 0.415 mmol), 2,8-diazaspiro[4.5]decane-1,3-dione (77.0 mg, 0.456 mmol) and potassium fluoride (48.2 mg, 0.830 mmol) were loaded in a microwave vial. The capped vial was evacuated using high vacuum and purged with nitrogen (each three times). Triethylamine (0.16 mL, 1.24 mmol) and NMP (1 mL) were added and the mixture was degassed again by using the high vacuum and purged with nitrogen again (each three times). The reaction mixture was heated in the microwave at 220° C. for 2 h and cooled, then ethyl acetate and water were added and the organic layer was separated. The aqueous layer was extracted twice with ethyl acetate. The combined organic layers were dried over MgSO$_4$, filtered and the solvent was evaporated under reduced pressure. The residue was purified by chromatography on silica gel (dichloromethane/ethanol) to give the title compound as a colourless oil. The product mixture was used in the next step without further purification.

3c. 8-(2-(Bis(4-methoxybenzyl)amino)-3-chloro-5-(4-(1-methyl-1H-pyrazol-4-yl)phenyl)pyridin-4-yl)-2,8-diazaspiro[4.5]decane-1,3-dione

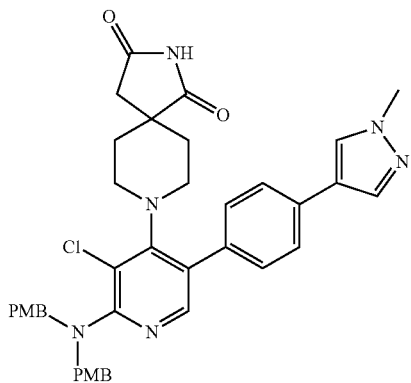

8-(2-(Bis(4-methoxybenzyl)amino)-5-bromo-3-chloropyridin-4-yl)-2,8-diazaspiro[4.5]decane-1,3-dione (90.0 mg, 0.110 mmol), 1-methyl-4-(4-(4,4,5,5-tetramethyl-1,3,2-dioxaborolan-2-yl)phenyl)-1H-pyrazole (34.4 mg, 0.121 mmol) and Pd(dppf)Cl$_2$·CH$_2$Cl$_2$ (4.02 mg, 5.50 μmol) were loaded in a microwave vial. The capped vial was evacuated using high vacuum and purged with nitrogen (each three times). Acetonitrile (0.8 mL) and aqueous sodium carbonate (0.5M, 0.308 mL, 0.154 mmol) were added and the mixture was degassed again by using the high vacuum and purged with nitrogen again (each three times). The mixture was heated in the microwave at 120° C. for 1 h before it was cooled and transferred into a flask with the help of chloroform/methanol and the water evaporated by azeotropic removal with toluene twice. The resulting residue was purified by chromatography on silica gel (dichloromethane/ethanol) to give the title compound as a light yellow oil (35.0 mg, 46%), which was used in the following step without further purification.

3d. 8-(2-Amino-3-chloro-5-(4-(1-methyl-1H-pyrazol-4-yl)phenyl)pyridin-4-yl)-2,8-diazaspiro[4.5]decane-1,3-dione (38)

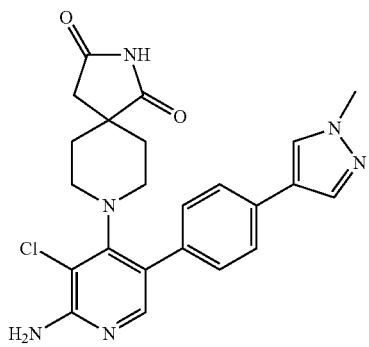 [SMILES: Cn1cc(-c2ccc(-c3cnc(N)c(Cl)c3N3CCC4(CC3)CC(=O)NC4=O)cc2)cn1]

8-(2-(Bis(4-methoxybenzyl)amino)-3-chloro-5-(4-(1-methyl-1H-pyrazol-4-yl)phenyl)pyridin-4-yl)-2,8-diazaspiro[4.5]decane-1,3-dione (35.0 mg, 0.051 mmol was dissolved in trifluoroacetic acid (1 mL) and the orange solution was stirred at RT for 1 h. The mixture was added into saturated NaHCO$_3$ dropwise before dichloromethane was added and the organic layer was separated. The aqueous layer was extracted twice with dichloromethane. The combined organic layers were washed with brine, dried over MgSO$_4$, filtered and the solvent was evaporated under reduced pressure. The resulting precipitate was filtrated off and the residue was purified by chromatography on silica gel (cyclohexane/ethyl acetate) followed by purification using a SCX$_2$-cartridge (eluting with dichloromethane/1N NH$_3$ in methanol). The resulting white solid is finally purified by preparative HPLC (Gilson, acetonitrile/water) to give the title compound as a white solid (5.00 mg, 7% over 3 steps). $^1$H-NMR (500 MHz, DMSO-d6) ppm=8.18 (s, 1H), 7.90 (d, J=0.5, 1H), 7.65 (s, 1H), 7.61 (d, J=8.2, 2H), 7.24 (d, J=8.2, 2H), 6.13 (s, 2H), 3.87 (s, 3H), 2.98 (d, J=12.8, 2H), 2.74-2.58 (m, 2H), 2.43 (s, 2H), 1.78 (t, J=11.9, 2H), 1.44 (d, J=11.9, 2H). HRMS m/z (ESI$^+$) [M+H]$^+$ C$_{23}$H$_{24}$ClN$_6$O$_2$, calc 451.1644, found 451.1632, Rt=1.93 min (HPLC method B).

3e. 8-{2-[Bis-(4-methoxy-benzyl)-amino]-5-bromo-3-chloro-pyridin-4-yl}-2,8-diaza-spiro[4.5]decan-1-one

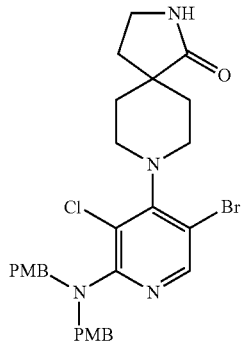

(5-Bromo-3,4-dichloro-pyridin-2-yl)-bis-(4-methoxy-benzyl)-amine (1.60 g, 3.32 mmol), 1-oxo-2,8-diaza-spiro[4.5]decane-8-carboxylic acid tert-butyl ester (1.52 g, 5.97 mmol) and triethylamine (0.755 g, 7.47 mmol) in NMP (10 mL) were heated in a microwave vial for 60 min at 220° C. The mixture was poured in water (600 mL), the formed precipitate was filtered and washed. The residue was purified using flash chromatography (petroleum ether/ethyl acetate). 1.08 g (1.80 mmol, 54%) of a colorless solid was obtained.

3f. 8-[2-Amino-3-chloro-5-(1-methyl-1H-indazol-5-yl)-pyridin-4-yl]-2,8-diaza-spiro[4.5]decan-1-one (25)

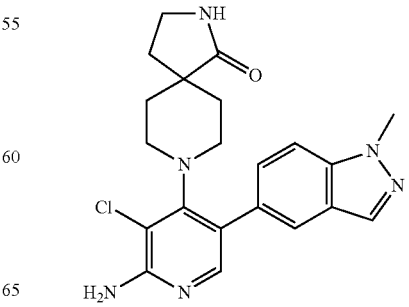

8-{2-[Bis-(4-methoxy-benzyl)-amino]-5-bromo-3-chloro-pyridin-4-yl}-2,8-diaza-spiro[4.5]decan-1-one (500 mg, 0.768 mmol) and 1-methylindazole-5-boronic acid (165 mg, 0.94 mmol) were suspended in 0.5 M sodium carbonate solution (2.5 mL) and acetonitrile (10 mL). The mixture was degassed, (1,1'-bis(diphenylphosphino)ferrocene)-palladium dichloride dichloromethane complex (25.5 mg, 0.031 mmol) was added and the mixture was microwaved under nitrogen atmosphere for 60 min at 120° C. The reaction mixture was evaporated to dryness and purified using flash chromatography. For the removal of the protecting group, the residue was dissolved in 5 mL trifluoro acetic acid and stirred for 2 h at RT. The solution was evaporated to dryness, 20 mL water was added and a weakly basic pH was adjusted adding solid sodium hydrogen carbonate and the aqueous layer was extracted twice with dichloromethane. The organic layer was dried over sodium sulfate, evaporated and purified using flash chromatography (methanol/dichloromethane). 143 mg (0.348 mmol, 45% (2 steps)) of the title compound were obtained as a colourless oil. $^1$H NMR (400 MHz, DMSO) ppm=8.06 (s, 1H), 7.68-7.64 (m, 2H), 7.48 (s, 1H), 7.27 (dd, J=8.7, 1.6, 1H), 6.09 (bs, 2H), 4.07 (s, 3H), 3.07 (t, J=6.8, 2H), 3.01-2.92 (m, 2H), 2.70-2.55 (m, 2H), 1.75 (t, J=6.8, 2H), 1.71-1.59 (m, 2H), 1.20-1.12 (m, 2H).

Compounds 1, 3, 7, 12, 13, 14, 15, 16, 17, 18, 19, 22, 23, 24, 25, 26, 28, 32, 33, 35, 38, 39, 43, 44, 49, 58, 59, 62, 67, 69, 70, 71, 72 and 73 have been prepared by one of the methods described above.

The same reaction cascade was employed to react 1-oxa-3,8-diaza-spiro[4.5]decan-2-one or 2,4-dioxo-1,3,8-triaza-spiro[4.5]decane-8-carboxylic acid tert-butyl ester with non- or protected 5-bromo-3,4-dichloro-pyridin-2-yl amine, followed by Suzuki reaction and deprotection, if applicable, resulting in 2, 4, 5, 6, 8, 9, 10, 20, 21, 29, 34, 36, 37, 41, 42, 54, 55, 60 and 63,

4. 1'-(2-Amino-3-chloro-5-(1-methyl-1H-indazol-5-yl)pyridin-4-yl)spiro[indoline-3,4'-piperidin]-2-one (31) and 1'-(2-amino-3-chloro-5-(4-(1-methyl-1H-pyrazol-4-yl)phenyl)pyridin-4-yl)spiro[indoline-3,4'-piperidin]-2-one (11)

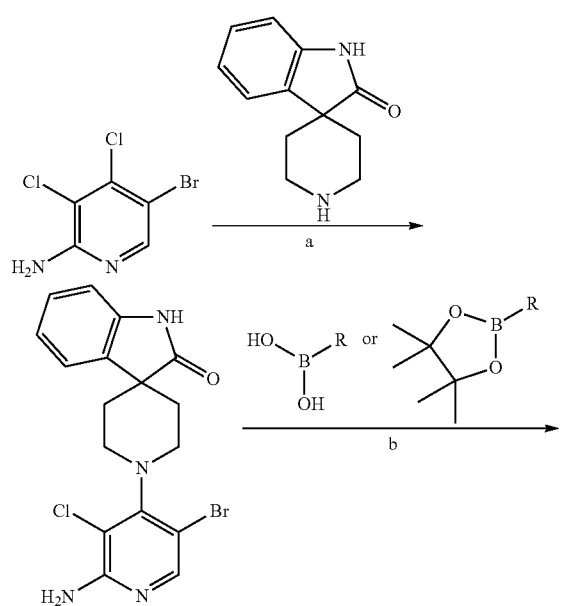

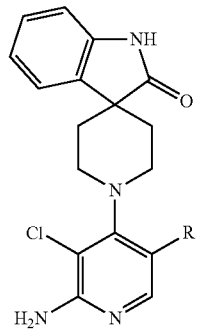

R = 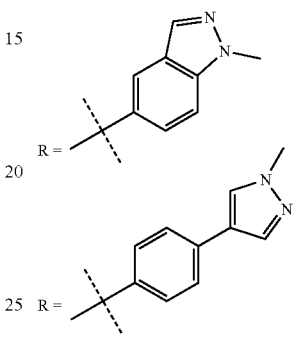

R = 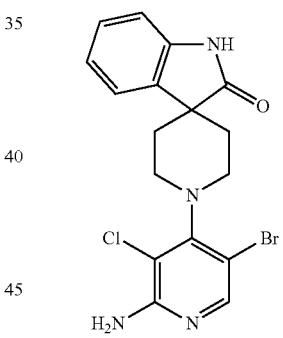

4a. 1'-(2-Amino-5-bromo-3-chloropyridin-4-yl)spiro[indoline-3,4'-piperidin]-2-one 5-Bromo-3,4-dichloro-N,N-bis(4-methoxybenzyl)pyridin-2-amine (100 mg, 0.413 mmol), spiro[indoline-3,4'-piperidin]-2-one (92.0 mg, 0.455 mmol) and potassium fluoride (48.0 mg, 0.827 mmol) were loaded in a microwave vial. The capped vial was evacuated using high vacuum and purged with nitrogen (each three times). Triethylamine (0.159 mL, 1.24 mmol) and NMP (1 mL) were added and the mixture was degassed again by using the high vacuum and purged with nitrogen again (each three times). The reaction mixture was heated in the microwave at 220° C. for 1.5 h before the mixture was added to vigorously stirred water (20 mL) dropwise. The resulting precipitate was filtrated off and purified by chromatography on silica gel (dichloromethane/ethanol). Recrystallization from ethyl acetate/diethyl ether gave the title compound as a white solid (45.5 mg, 27%). $^1$H-NMR (500 MHz, DMSO-d6) ppm=10.45 (s, 1H), 7.97 (s, 1H), 7.46 (d, J=7.2, 1H), 7.22 (t, J=7.7, 1H), 7.01 (dd, J=7.2, 7.2, 1H), 6.88 (d, J=7.2, 1H), 6.39 (s, 2H), 3.70-3.36

(m, 4H), 2.08-1.64 (m, 4H). HRMS m/z (ESI+) [M+H]+ $C_{17}H_{17}BrClN_4O$, calc 407.0269, found 407.0264, Rt=2.99 min (HPLC method B).

4b1. 1'-(2-Amino-3-chloro-5-(1-methyl-1H-indazol-5-yl)pyridin-4-yl)spiro[indoline-3,4'-piperidin]-2-one (31)

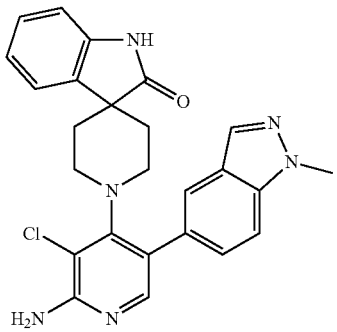 [SMILES: Cn1ncc2cc(-c3cnc(N)c(Cl)c3N3CCC4(CC3)C(=O)Nc3ccccc34)ccc21]

1'-(2-Amino-5-bromo-3-chloropyridin-4-yl)spiro[indoline-3,4'-piperidin]-2-one (20.0 mg, 0.049 mmol), 1-methyl-1H-indazol-5-ylboronic acid (8.63 mg, 0.049 mmol) and tetrakis(triphenylphosphine) palladium(0) (2.83 mg, 2.45 μmol) were loaded in a microwave vial. The capped vial was evacuated using high vacuum and purged with nitrogen (each three times). Acetonitrile (0.5 mL) and aqueous sodium carbonate (0.5M, 0.137 mL, 0.069 mmol) were added and the mixture was degassed again by using the high vacuum and purged with nitrogen again (each three times). The mixture was heated in the microwave at 120° C. for 1 h before it was transferred into a flask with the help of chloroform/methanol and the water was evaporated by azeotropic removal with toluene twice. The resulting residue was purified by chromatography on silica gel (dichloromethane/ethanol) followed by purification using a $SCX_2$-cartridge (eluting with dichloromethane/1N $NH_3$ in methanol). Recrystallization from ethyl acetate/diethyl ether gave the title compound as a white solid (10.0 mg, 44%). $^1$H-NMR (500 MHz, DMSO-d6) ppm=10.34 (s, 1H), 8.15 (s, 1H), 7.83-7.67 (m, 3H), 7.41 (d, J=8.2, 1H), 7.21 (d, J=7.5, 1H), 7.15 (dd, J=7.6, 7.6, 1H), 6.88 (dd, J=7.6, 7.6, 1H), 6.8 (d, J=7.5, 1H), 6.15 (s, 2H), 4.09 (s, 3H), 3.23-3.07 (m, 2H), 3.07-2.87 (m, 2H), 1.87-1.62 (m, 2H), 1.53-1.21 (m, 2H). HRMS m/z (ESI+) [M+H]+ $C_{25}H_{23}ClN_6O$, calc 459.1695, found 459.1682, Rt=2.33 min (HPLC method B).

4b2. 1'-(2-Amino-3-chloro-5-(4-(1-methyl-1H-pyrazol-4-yl)phenyl)pyridin-4-yl)spiro[indoline-3,4'-piperidin]-2-one (11)

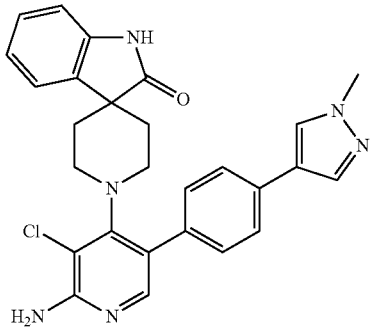

1'-(2-Amino-5-bromo-3-chloropyridin-4-yl)spiro[indoline-3,4'-piperidin]-2-one (22 mg, 0.054 mmol), 1-methyl-4-(4-(4,4,5,5-tetramethyl-1,3,2-dioxaborolan-2-yl)phenyl)- 1H-pyrazole (15.3 mg, 0.054 mmol) and tetrakis(triphenylphosphine)palladium(0) (3.12 mg, 2.70 μmol) were loaded in a microwave vial. The capped vial was evacuated using high vacuum and purged with nitrogen (each three times). Acetonitrile (0.6 mL) and aqueous sodium carbonate (0.5M, 0.151 mL, 0.076 mmol) were added and the mixture was degassed again by using the high vacuum and purged with nitrogen again (each three times). The mixture was heated in the microwave at 120° C. for 1 h before it was transferred into a flask with the help of chloroform/methanol and the water was evaporated by azeotropic removal with toluene twice. The resulting residue was purified by chromatography on silica gel (dichloromethane/ethanol) followed by further purification by prep. HPLC (Gilson, acetonitrile/water) to give the title compound as a white solid (10.0 mg, 38%). $^1$H-NMR (500 MHz, DMSO-d$^6$) ppm=10.35 (s, 1H), 8.20 (s, 1H), 7.93 (s, 1H), 7.70 (s, 1H), 7.69 (d, J=6.1, 2H), 7.35 (d, J=8.0, 2H), 7.30 (d, J=7.4, 1H), 7.17 (dd, J=7.7, 0.9, 1H), 6.97 (dd, J=7.6, 0.9, 1H), 6.83 (d, J=7.6, 1H), 6.16 (s, 2H), 3.88 (s, 3H), 3.26-3.15 (m, 2H), 3.07-2.98 (m, 2H), 1.89-1.71 (m, 2H), 1.56-1.34 (m, 2H). HRMS m/z (ESI+) [M+H]+ $C_{27}H_{26}ClN_6O$, calc 485.1851, found 485.1831, Rt=2.38 min (HPLC method B).

5. 8-(2-Amino-5-(1-methyl-1H-indazol-5-yl)-3-(trifluoromethyl)pyridin-4-yl)-2,8-diazaspiro[4.5]decan-1-one (39)

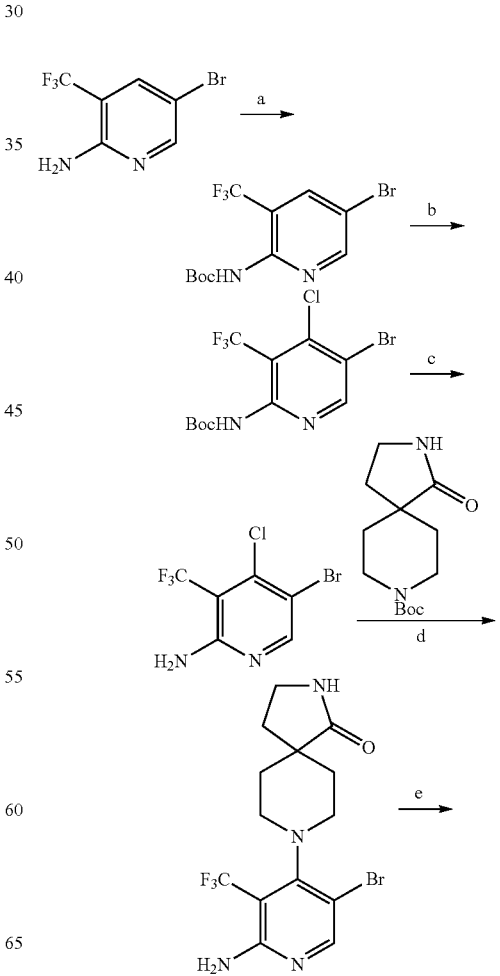

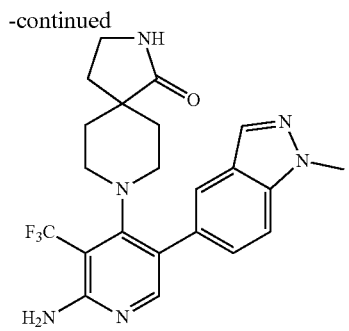

5a. tert-Butyl 5-bromo-3-(trifluoromethyl)pyridin-2-ylcarbamate

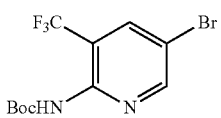

NaH (0.398 g, 9.96 mmol) was added to a solution of 5-bromo-3-(trifluoromethyl)pyridin-2-amine (1.00 g, 4.15 mmol) in THF (40 mL) at 0° C. under nitrogen atmosphere. The reaction was stirred at RT for 60 min after which the reaction was cooled to 0° C. and Boc$_2$O (0.906 g, 4.15 mmol) in THF (10 mL) was added. The reaction was warmed to RT and stirred for 16 h. The reaction was quenched with sat. NaHCO$_3$ (aq) and extracted with diethyl ether. The combined organic layers were washed with water and brine, dried with MgSO$_4$, filtered and the solvent evaporated. Purification by flash chromatography (EtOAc/cyclohexane) was unsuccessful and the product was still contaminated with approximately 4% of unreacted starting material. Sublimation overnight (30 mbar, 110° C.) afforded the product (0.54 g, 38%) as colourless crystals. $^1$H-NMR (500 MHz, CDCl$_3$) ppm=8.68 (d, J=2.4, 1H), 8.01 (dd, J=2.4, 0.6, 1H), 7.00 (s, 1H), 1.54 (s, 9H). HRMS m/z (ESI$^+$) [M+H-Boc]$^+$ C$_6$H$_5$BrF$_3$N$_2$ calc 240.9583, found 240.9581, Rt=2.92 min ((HPLC method B).

5b. tert-Butyl 5-bromo-4-chloro-3-(trifluoromethyl)pyridin-2-ylcarbamate

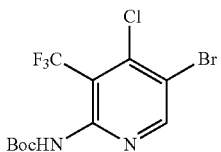

Butyl lithium (1.6 M in hexanes, 0.766 mL, 1.23 mmol) was added to diisopropylamine (0.189 mL, 1.34 mmol) in THF (3.5 mL) at −78° C. under nitrogen atmosphere. After 30 min tert-butyl 5-bromo-3-(trifluoromethyl)pyridin-2-ylcarbamate (190 mg, 0.557 mmol) in THF (1.5 mL) was added dropwise resulting in a dark yellow solution. After 1 h, hexachloroethane (343 mg, 1.448 mmol) in THF (1 mL) was added dropwise to the yellow brown suspension, resulting in a dark brown solution. After stirring at −78° C. for 80 min, the reaction was allowed to warm to RT over 15 min, and then quenched with sat. NH$_4$Cl(aq). The reaction mixture was extracted with diethyl ether (3×) and the combined organic layers were washed with water (2×) and brine, dried with MgSO$_4$, filtered and the solvent evaporated. The crude was purified by flash chromatography (EtOAc/cyclohexane) to give product (157 mg, 75%) as a cream solid. $^1$H-NMR (500 MHz, CDCl$_3$) ppm=8.67 (s, 1H), 7.24 (bs, 1H), 1.51 (s, 9H). HRMS m/z (ESI$^+$) [M+H-Boc]$^+$ C$_6$H$_4$BrClF$_3$N$_2$, calc 274.9193, found 274.9191, Rt=3.11 min (HPLC method B).

5c. 5-Bromo-4-chloro-3-(trifluoromethyl)pyridin-2-amine

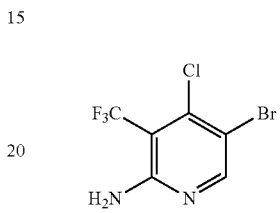

tert-Butyl 5-bromo-4-chloro-3-(trifluoromethyl)pyridin-2-ylcarbamate (150 mg, 0.399 mmol) was dissolved in DCM (2 mL) and TFA (2 mL) was added at RT. After 2.5 h the reaction was complete and the solvent was evaporated. The crude product was redissolved in DCM and washed with aq. Na$_2$CO$_3$ (0.5 M) and brine. The organic layer was dried over MgSO$_4$, filtered and the solvent evaporated to give the product (109 mg, 99%) as a pale yellow solid. $^1$H-NMR (500 MHz, CDCl$_3$) ppm=8.31 (s, 1H), 5.27 (s, 2H). HRMS m/z (ESI$^+$) [M+H]$^+$ C$_6$H$_4$BrClF$_3$N$_2$ calc 274.9193, found 274.9190, Rt=3.02 min (HPLC method B).

5d. 8-(2-Amino-5-bromo-3-(trifluoromethyl)pyridin-4-yl)-2,8-diazaspiro[4.5]decan-1-one

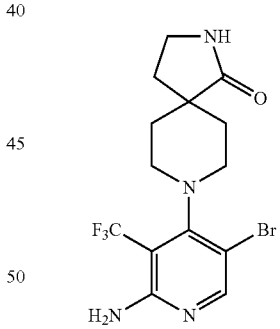

A mixture of 5-bromo-4-chloro-3-(trifluoromethyl)pyridin-2-amine (87.0 mg, 0.316 mmol), tert-butyl 1-oxo-2,8-diazaspiro[4.5]decane-8-carboxylate (241 mg, 0.948 mmol) and triethylamine (0.044 mL, 0.316 mmol) in 2-methoxy-2-isopropanol (1 mL) was reacted for 2 h at 220° C. in the microwave under nitrogen atmosphere. The solvent was evaporated and the crude purified by flash chromatography (DCM/MeOH) to give the title compound (35.0 mg, 28%) as a pale yellow solid. $^1$H-NMR (500 MHz, CDCl$_3$) ppm=8.19 (s, 1H), 5.75 (s, 1H), 5.24-4.92 (m, 2H), 3.37 (t, J=6.7, 2H), 3.67-2.80 (m, 4H), 2.16 (t, J=6.7, 2H), 2.15-2.05 (m, 2H), 1.47 (d, J=13.8, 2H). HRMS m/z (ESI$^+$) [M+H]$^+$ C$_{14}$H$_{17}$BrF$_3$N$_4$O calc 393.0532, found 393.0535, Rt=2.51 min (HPLC method B).

5e. 8-(2-Amino-5-(1-methyl-1H-indazol-5-yl)-3-(trifluoromethyl)pyridin-4-yl)-2,8-diazaspiro[4.5]decan-1-one (39)

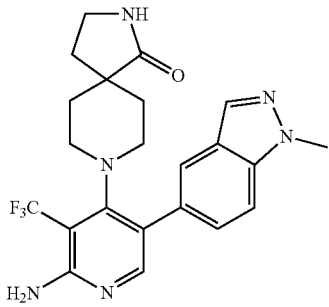

8-(2-Amino-5-bromo-3-(trifluoromethyl)pyridin-4-yl)-2,8-diazaspiro[4.5]decan-1-one (22.0 mg, 0.056 mmol), 1-methyl-1H-indazol-5-ylboronic acid (10.8 mg, 0.062 mmol) and Pd(dppf)Cl$_2$.CH$_2$Cl$_2$ (2.30 mg, 2.80 μmol) were loaded in a microwave vial which was sealed and flushed with nitrogen. Acetonitrile (0.7 mL) and aq. sodium carbonate (0.5 M, 0.154 mL, 0.077 mmol) were added and the rubber septum was removed and the vial capped. The reaction mixture was heated in the microwave at 120° C. for 75 min and then concentrated. Purification by flash chromatography (DCM/MeOH) followed by preparative TLC (MeOH/DCM) afforded the title compound (3.30 mg, 13%) as a white solid. $^1$H-NMR (500 MHz, CDCl$_3$) ppm=8.03 (d, J=1.0, 1H), 7.94 (s, 1H), 7.63 (dd, J=1.6, 0.8, 1H), 7.49 (d, J=8.6, 1H), 7.36 (d, J=8.6, 1H), 5.33 (bs, 1H), 5.07 (bs, 2H), 4.14 (s, 3H), 3.21 (t, J=6.8, 2H), 3.07 (dt, J=12.3, 3.4, 2H), 2.85-2.71 (m, 2H), 1.87-1.71 (m, 4H), 1.16 (d, J=13.1, 2H). HRMS m/z (ESI$^+$) [M+H]$^+$ C$_{22}$H$_{24}$F$_3$N$_6$O calc 445.1958, found 445.1955, Rt=1.94 min (HPLC method B).

6. 1-(2-Amino-3-chloro-5-(4-(4-methylpiperazin-1-yl)phenyl)pyridin-4-yl)piperidine-4-carbonitrile (30) and 1-(2-amino-3-chloro-5-(4-morpholinophenyl)pyridin-4-yl)piperidine-4-carbonitrile (27)

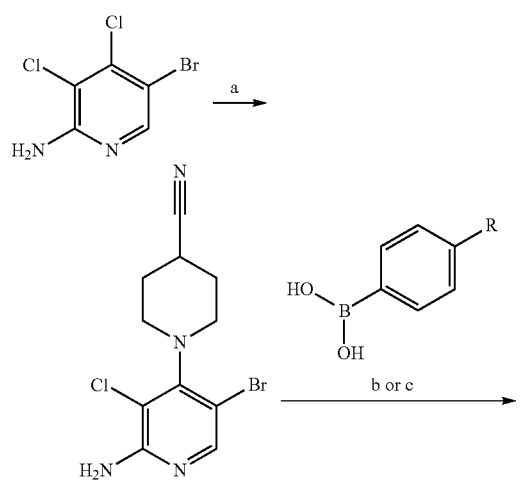

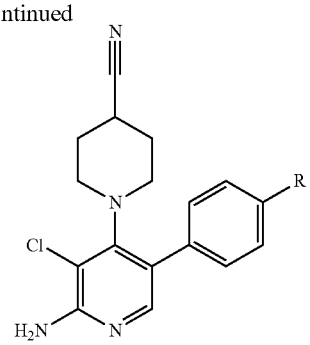

R = 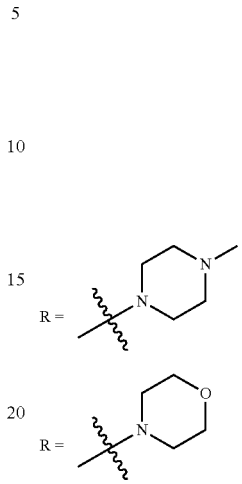

6a. 1-(2-Amino-5-bromo-3-chloropyridin-4-yl)piperidine-4-carbonitrile

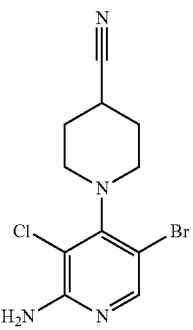 [SMILES: N#CC1CCN(c2c(Br)cnc(N)c2Cl)CC1]

5-Bromo-3,4-dichloropyridin-2-amine (400 mg, 1.65 mmol) was dissolved in NMP (2.5 mL) and 4-cyanopiperidine (911 mg, 8.27 mmol) was added. The vial was sealed and placed under high vacuum until effervescence ceased. After five vacuum/nitrogen cycles the septum was removed and the vial was capped and heated in the microwave under nitrogen atmosphere at 200° C. for 3 h. The reaction was poured into water and extracted with EtOAc/cHex (1:1, 3×). The combined organic layers were washed with water (2×) and brine, dried over Na$_2$SO$_4$, filtered and the solvent evaporated. The crude product was purified by flash chromatography (EtOAc/cyclohexane/DCM) to give the product (0.393 g, 75%) as a white solid. $^1$H-NMR (500 MHz, CDCl$_3$) ppm=8.00 (s, 1H), 4.90 (s, 2H), 3.49-3.32 (m, 2H), 3.23 (ddd, J=12.7, 6.7, 4.6, 2H), 2.97-2.71 (m, 1H), 2.11-1.94 (m, 4H). HRMS m/z (ESI$^+$) [M+H]$^+$ C$_{11}$H$_{13}$BrClN$_4$ calc 315.0007, found 315.0008, Rt=2.44 min (HPLC method B).

6b. 1-(2-Amino-3-chloro-5-(4-(4-methylpiperazin-1-yl)phenyl)pyridin-4-yl)piperidine-4-carbonitrile (30)

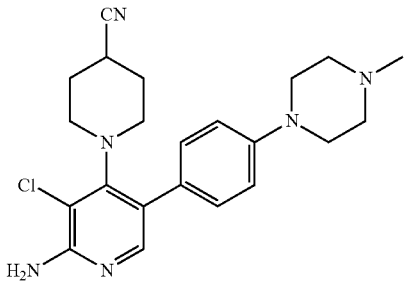 [SMILES: CN1CCN(c2ccc(-c3cnc(N)c(Cl)c3N3CCC(C#N)CC3)cc2)CC1]

1-(2-Amino-5-bromo-3-chloropyridin-4-yl)piperidine-4-carbonitrile (50.0 mg, 0.158 mmol), 4-(4-methylpiperazin-1-yl)phenylboronic acid (36.6 mg, 0.166 mmol) and Pd(dppf)Cl$_2$.CH$_2$Cl$_2$ (6.47 mg, 7.92 µmol) were loaded in a microwave vial which was sealed and flushed with nitrogen, acetonitrile (1 mL) and aq. sodium carbonate (0.5 M, 0.437 mL, 0.219 mmol) were added and the vial was capped and heated in the microwave at 120° C. for 1 h. The solvent was evaporated and the product was purified by flash chromatography ("1M NH$_3$ in MeOH" in DCM). A small amount of impurity co-eluted with the product and was subsequently removed by recrystallization from hot EtOAc to give the title compound (20.0 mg, 31%) as a white solid. $^1$H-NMR (500 MHz, CDCl$_3$) ppm=7.75 (s, 1H), 7.11 (d, J=8.7, 2H), 6.96 (d, J=8.7, 2H), 4.81 (s, 2H), 3.27-3.25 (m, 4H), 3.12-3.03 (m, 2H), 2.85-2.60 (m, 3H), 2.61-2.59 (m, 4H), 2.37 (s, 3H), 1.89-1.77 (m, 4H). HRMS m/z (ESI$^+$) [M+H]$^+$ C$_{22}$H$_{28}$ClN$_6$ calc 411.2058, found 411.2056, Rt=1.38 min (HPLC method B).

6c. 1-(2-Amino-3-chloro-5-(4-morpholinophenyl)pyridin-4-yl)piperidine-4-carbonitrile (27)

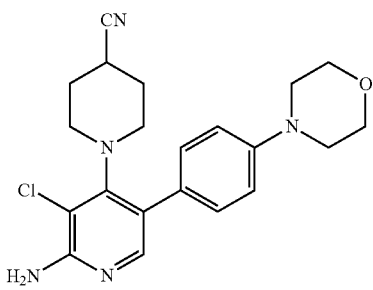

1-(2-Amino-5-bromo-3-chloropyridin-4-yl)piperidine-4-carbonitrile (50.0 mg, 0.158 mmol) was reacted with 4-morpholinophenylboronic acid (34.4 mg, 0.166 mmol) and Pd(dppf)Cl$_2$.CH$_2$Cl$_2$ (6.47 mg, 7.92 µmol) in acetonitrile (1 mL) according to the procedure used above. Purification by flash chromatography ("1M NH$_3$ in MeOH" in DCM) followed by recrystallization from hot EtOAc afforded the title compound (20.0 mg, 32%) as a white solid. $^1$H-NMR (500 MHz, CDCl$_3$) ppm=7.76 (s, 1H). 7.15-7.11 (m, 2H), 6.97-6.93 (m, 2H), 4.82 (s, 2H), 3.90-3.88 (m, 4H), 3.22-3.20 (m, 4H), 3.13-3.01 (m, 2H), 2.90-2.52 (m, 3H), 1.91-1.76 (m, 4H). HRMS m/z (ESI$^+$) [M+H]$^+$ C$_{21}$H$_{25}$ClN$_5$O, calc 398.1742, found 398.1733, Rt=2.04 min (HPLC method B).

In a similar fashion isonipecotamide or its derivatives can be reacted instead of 4-cyanopiperidine. These intermediated also underwent Pd-catalyzed reactions to form the final cpds 47 and 48.

7. 8-(2-Amino-3-chloro-5-(1-methyl-2,2-dioxido-1,3-dihydrobenzo[c]isothiazol-5-yl)pyridin-4-yl)-2,8-diazaspiro[4.5]decan-1-one (26)

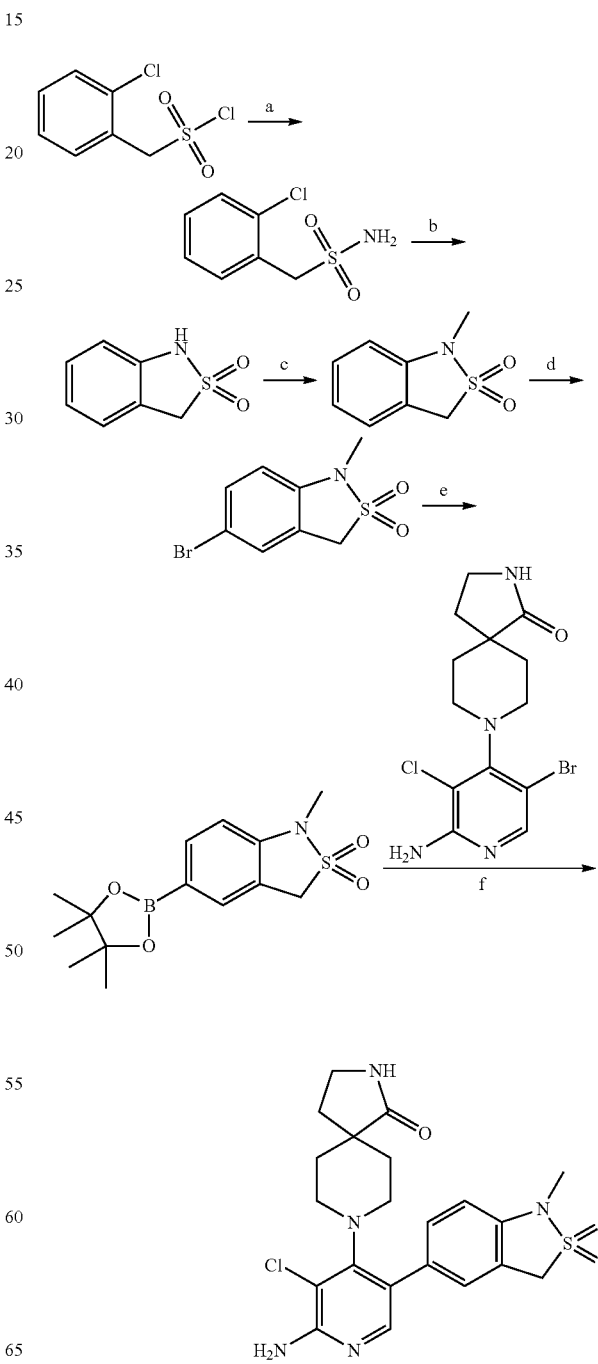

7a. (2-Chlorophenyl)methanesulfonamide

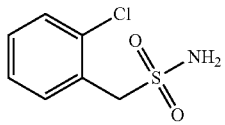 [SMILES: NS(=O)(=O)Cc1ccccc1Cl]

2-Chlorobenzylsulfonyl chloride (1.86 g, 8.26 mmol) was dissolved in acetone (27 mL) and then ammonium hydroxide (18.0 mL, 158 mmol) was added. The reaction was stirred for 2.5 h at RT and the solvent was evaporated. The reaction mixture was diluted with ethyl acetate and water was added. The two layers were separated and the aqueous layer was extracted with ethyl acetate. The combined organic layers were dried over magnesium sulphate and concentrated under vacuum. The crude product was purified by column chromatography (DCM/EtOH) to afford the title compound as a white solid (1.50 g, 88%). $^1$H NMR (500 MHz, CDCl$_3$) ppm=7.56-7.53 (m, 1H), 7.47-7.44 (m, 1H), 7.36-7.30 (m, 2H), 4.66 (bs, 2H), 4.57 (s, 2H). Rt=1.77 min (HPLC method C).

7b. 1,3-Dihydrobenzo[c]isothiazole 2,2-dioxide

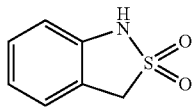 [SMILES: O=S1(=O)Cc2ccccc2N1]

(2-Chlorophenyl)methanesulfonamide (450 mg, 2.19 mmol), tris(dibenzylideneacetone)dipalladium (100 mg, 0.109 mmol), 2-di-tert-butylphosphino-2',4',6'-tri-isopropylbiphenyl (186 mg, 0.438 mmol) and potassium carbonate (605 mg, 4.38 mmol) were loaded in a microwave vial and THF (8.8 mL) was added. The reaction mixture was stirred at 80° C. for 13 h before being quenched with a saturated solution of ammonium chloride. The solvent was then evaporated and the residue was purified by column chromatography (cyclohexane/acetone) to afford the title compound as a white solid (296 mg, 80%). $^1$H NMR (500 MHz, CDCl$_3$) ppm=7.31-7.26 (m, 1H), 7.26-7.23 (m, 1H), 7.07 (td, J=7.6, 0.9, 1H), 6.90 (d, J=8.0, 1H), 6.48 (bs, 1H), 4.39 (s, 2H). Rt=1.69 min (HPLC method C).

7c. 1-Methyl-1,3-dihydrobenzo[c]isothiazole-2,2-dioxide

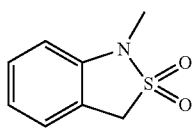

To a suspension of 1,3-dihydrobenzo[c]isothiazole-2,2-dioxide (280 mg, 1.655 mmol) and potassium carbonate (229 mg, 1.66 mmol) in DMF (5 mL) was added iodomethane (414 µL, 6.62 mmol). The reaction was stirred for 6 h at RT and was then quenched with a saturated solution of ammonium chloride. The reaction mixture was concentrated and purified by column chromatography (cyclohexane/acetone) to afford the title compound as a white solid (270 mg, 89%). $^1$H NMR (500 MHz, CDCl$_3$) ppm=7.37-7.32 (m, 1H), 7.27-7.24 (m, 1H), 7.02 (td, J=7.6, 1.0, 1H), 6.73 (d, J=8.0, 1H), 4.34 (s, 2H), 3.14 (s, 3H). Rt=2.07 min (HPLC method C).

7d. 5-Bromo-1-methyl-1,3-dihydrobenzo[c]isothiazole-2,2-dioxide

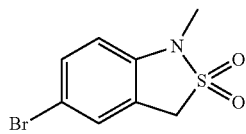

1-Methyl-1,3-dihydrobenzo[c]isothiazole-2,2-dioxide (272 mg, 1.49 mmol) was dissolved in DMF (1.5 mL) and then N-bromosuccinimide (264 mg, 1.49 mmol) was added. The reaction mixture was stirred at RT for 4 h. After addition of water, the reaction mixture was concentrated. The residue was purified by column chromatography (cyclohexane/acetone) to afford the title compound as a white solid (330 mg, 85%). $^1$H NMR (500 MHz, CDCl$_3$) ppm=7.45-7.41 (m, 1H), 7.37-7.35 (m, 1H), 6.59 (d, J=8.5, 1H), 4.30 (s, 2H), 3.09 (s, 3H). Rt=2.46 min (HPLC method B).

7e. 1-Methyl-5-(4,4,5,5-tetramethyl-1,3,2-dioxaborolan-2-yl)-1,3-dihydrobenzo[c]isothiazole 2,2-dioxide

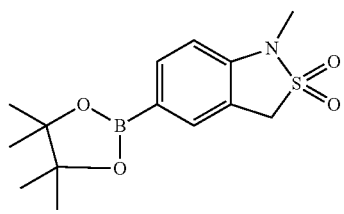 [SMILES: CN1c2ccc(B3OC(C)(C)C(C)(C)O3)cc2CS1(=O)=O]

5-Bromo-1-methyl-1,3-dihydrobenzo[c]isothiazole-2,2-dioxide (267 mg, 1.02 mmol), bis(pinacolato)diboron (388 mg, 1.53 mmol), potassium acetate (300 mg, 3.06 mmol) and Pd(dppf)Cl$_2$.CH$_2$Cl$_2$ (42.0 mg, 0.051 mmol) were loaded in a microwave vial and DME (7.4 mL) was added. The reaction was stirred in an oil bath at 80° C. overnight. The reaction was concentrated and purified by column chromatography (cyclohexane/acetone) to afford the title compound as a white solid (290 mg, 92%). $^1$H NMR (500 MHz, CDCl$_3$) ppm=7.80-7.77 (m, 1H), 7.69-7.67 (m, 1H), 6.71 (d, J=8.0, 1H), 4.32 (s, 2H), 3.15 (s, 3H), 1.33 (s, 12H). LC-MS (ESI, m/z) Rt=2.82 min-310 (M+)$^+$ (HPLC method B).

7f. 8-(2-Amino-3-chloro-5-(1-methyl-2,2-dioxido-1,3-dihydrobenzo[c]isothiazol-5-yl)pyridin-4-yl)-2,8-diazaspiro[4.5]decan-1-one (26)

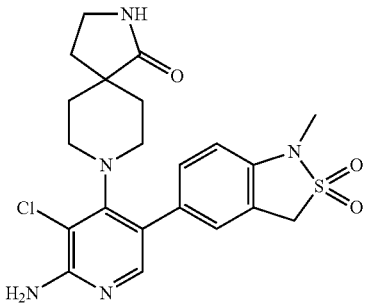

8-(2-Amino-5-bromo-3-chloropyridin-4-yl)-2,8-diazaspiro[4.5]decan-1-one (40.0 mg, 0.111 mmol), 1-methyl-5-(4,4,5,5-tetramethyl-1,3,2-dioxaborolan-2-yl)-1,3-dihydrobenzo[c]isothiazole-2,2-dioxide (41.0 mg, 0.133 mmol) and tetrakis(triphenylphosphine) palladium(0) (6.40 mg, 5.56 µmol) were loaded in a microwave vial and then degassed acetonitrile (2 mL) and degassed 0.5 M aqueous sodium carbonate (310 µL, 0.156 mmol) were added. The reaction was heated at 120° C. under microwave irradiation for 60 min. Then, the reaction mixture was concentrated and purified by column chromatography (DCM/EtOH) to afford the title compound as a white solid (22 mg, 43%). $^1$H NMR (500 MHz, DMSO-d$^6$) ppm=7.62 (s, 1H), 7.53 (s, 1H), 7.28 (s, 1H), 7.23 (d, J=8.2, 1H), 6.98 (d, J=8.2, 1H), 6.14 (bs, 2H), 4.71 (s, 2H), 3.11 (t, J=6.9, 2H), 3.07 (s, 3H), 2.98-2.91 (m, 2H), 2.77-2.65 (m, 2H), 1.84 (t, J=6.9, 2H), 1.69-1.60 (m, 2H), 1.21-1.16 (m, 2H). HRMS m/z (ESI$^+$) [M+H]$^+$ C$_{21}$H$_{24}$ClN$_5$OS, calc 462.1361, found 462.1352, Rt=1.76 min (HPLC method B).

Preparation of Additional Boronic Acids or Esters

Preparation of 1-methyl-4-(4-(4,4,5,5-tetramethyl-1,3,2-dioxaborolan-2-yl)phenyl)-1H-pyrazole

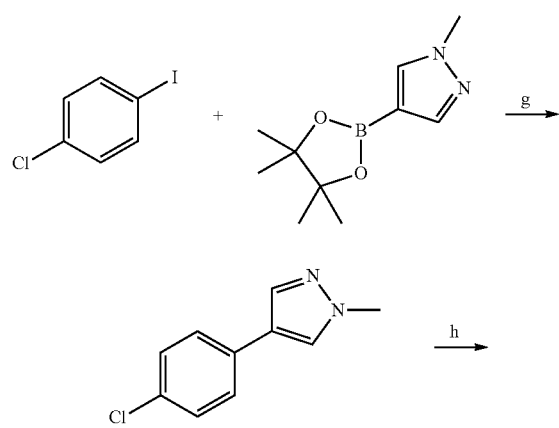

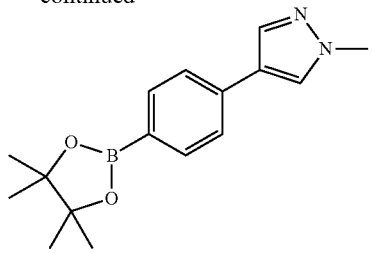

7g. 4-(4-Chlorophenyl)-1-methyl-1H-pyrazole

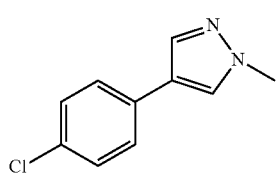

1-Chloro-4-iodobenzene (6.39 g, 26.8 mmol), 1-methyl-4-(4,4,5,5-tetramethyl-1,3,2-dioxaborolan-2-yl)-1H-pyrazole (5.58 g, 26.8 mmol), sodium carbonate (6.25 g, 59.0 mmol) and Pd(dppf)Cl$_2$.CH$_2$Cl$_2$ (2.20 g, 2.68 mmol) were loaded in a flask and then a mixture of THF/H$_2$O 3/1 (117 mL) was added. The reaction mixture was heated in an oil bath at 80° C. overnight. It was then concentrated under vacuum and the residue purified by column chromatography (cyclohexane/EtOAc) to afford the title compound as a white solid (3.80 g, 74%). $^1$H NMR (500 MHz, CDCl$_3$) ppm=7.72 (s, 1H), 7.57 (s, 1H), 7.38 (d, J=8.7, 2H), 7.31 (d, J=8.7, 2H), 3.93 (s, 3H). LC-MS (ESI, m/z) Rt=2.88 min-193 (M+H)$^+$ (HPLC method B).

7h. 1-Methyl-4-(4-(4,4,5,5-tetramethyl-1,3,2-dioxaborolan-2-yl)phenyl)-1H-pyrazole

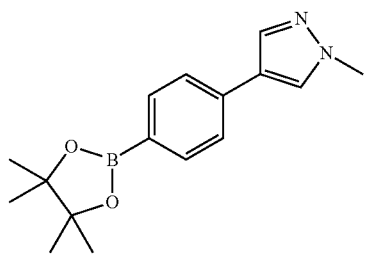

4-(4-Chlorophenyl)-1-methyl-1H-pyrazole (3.30 g, 17.1 mmol), bis(pinacolato)diboron (5.20 g, 20.6 mmol), potassium acetate (5.00 g, 51.4 mmol), Xphos (650 mg, 1.37 mmol) and Pd$_2$dba$_3$ (310 mg, 0.343 mmol) were loaded in a flask and then dioxane (34.3 mL) was added. The reaction mixture was stirred in an oil bath at 85° C. overnight. The solvent was evaporated and the crude product purified by column chromatography (cyclohexane/EtOAc) to afford the title compound as a white solid (3.9 g contaminated by 10% of 1-methyl-4-phenyl-1H-pyrazole, corrected yield 75%). 1H NMR (500 MHz, CDCl$_3$) ppm=7.79 (d, J=8.3, 2H), 7.79 (s, 1H), 7.64 (s, 1H), 7.47 (d, J=8.3, 2H), 3.93 (s, 3H), 1.35 (s, 12H). LC-MS (ESI, m/z) Rt=3.06 min-285 (M+H)$^+$ (HPLC method B).

7i. 6-(4,4,5,5-Tetramethyl-1,3,2-dioxaborolan-2-yl)indolin-2-one

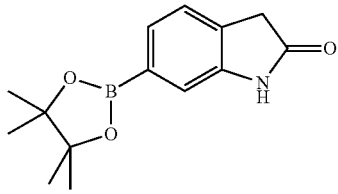 [SMILES: CC1(C)OB(c2ccc3c(c2)NC(=O)C3)OC1(C)C]

Four microwave vials were loaded as follows: 6-Bromoindolin-2-one (500 mg, 2.36 mmol), bis(pinacolato)diboron (898 mg, 3.54 mmol), potassium acetate (694 mg, 7.07 mmol) and Pd(dppf)Cl$_2$.CH$_2$Cl$_2$ (96.0 mg, 0.118 mmol) were dissolved in DME (17 mL). The reaction was heated at 80° C. overnight. The content of the four vials was then combined, concentrated and purified by column chromatography (cyclohexane/EtOAc) to afford the title compound as a white solid (2.27 g, 75%, purity 80%). 1H NMR (500 MHz, CDCl$_3$) ppm=8.57 (bs, 1H), 7.48 (d, J=7.3, 1H), 7.31 (s, 1H), 7.23 (d, J=7.3, 1H), 3.55 (s, 2H), 1.33 (s, 12H). LC-MS (ESI, m/z) Rt=2.75 min-260 (M+H)$^+$ (HPLC method B).

7j. 1-Methyl-3-(4-(4,4,5,5-tetramethyl-1,3,2-dioxaborolan-2-yl)phenyl)-1H-pyrazole

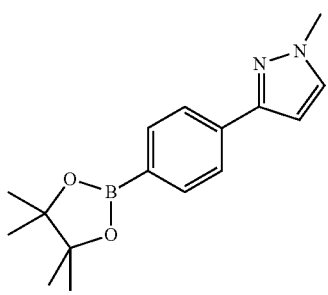 [SMILES: Cn1ccc(-c2ccc(B3OC(C)(C)C(C)(C)O3)cc2)n1]

3-(4-Bromophenyl)-1-methyl-1H-pyrazole (500 mg, 2.11 mmol), bis(pinacolato)diboron (876 mg, 3.45 mmol), potassium acetate (621 mg, 6.33 mmol) and Pd(dppf)Cl$_2$.CH$_2$Cl$_2$ (86 mg, 0.105 mmol) were loaded in a microwave vial and then DME (15 mL) was added. The reaction mixture was stirred in an oil bath at 80° C. overnight and then concentrated. The residue was purified by column chromatography (cyclohexane/EtOAc) to afford the title compound as a white solid (551 mg, 92%). $^1$H NMR (500 MHz, CDCl$_3$) ppm=7.83 (d, J=8.3, 2H), 7.80 (d, J=8.3, 2H), 7.37 (d, J=2.2, 1H), 6.57 (d, J=2.2, 1H), 3.95 (s, 3H), 1.35 (s, 12H). LC-MS (ESI, m/z) Rt=3.06 min-285 (M+H)$^+$ (HPLC method B).

7k. 5-[4-(4,4,5,5-Tetramethyl-[1,3,2]dioxaborolan-2-yl)-phenyl]-pyridin-2-ylamine

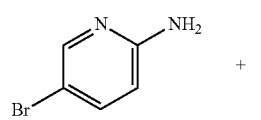

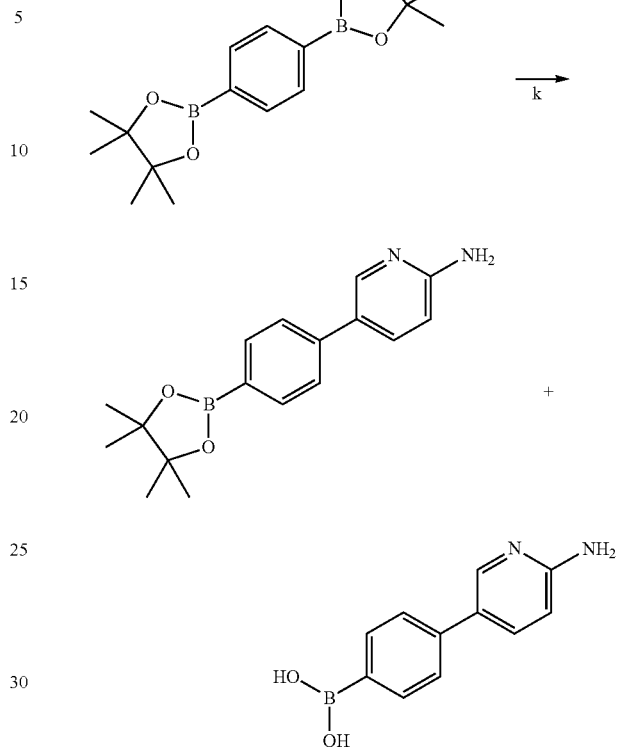

5-Bromo-pyridin-2-ylamine (98%, 500 mg, 2.89 mmol) and 1,4-benzenediboronic acid bis(pinacol) ester (1.40 g, 4.25 mmol) were suspended in 1M sodium carbonate solution (5.7 mL) and acetonitrile (10 mL). The mixture was degassed, (1,1'-bis(diphenylphosphino)ferrocene)-palladium dichloride dichloromethane complex (116 mg, 0.143 mmol) was added and the mixture was microwaved under nitrogen atmosphere for 60 min at 120° C. The reaction mixture was filtered and the filtrate was concentrated and purified using flash chromatography. 534 mg (1.80 mmol, 64%) of a colorless oil were obtained.

Preparation of 1-[2-(tetrahydro-pyran-2-yloxy)-ethyl]-4-[4-(4,4,5,5-tetramethyl-[1,3,2]dioxaborolan-2-yl)-phenyl]-1H-pyrazole

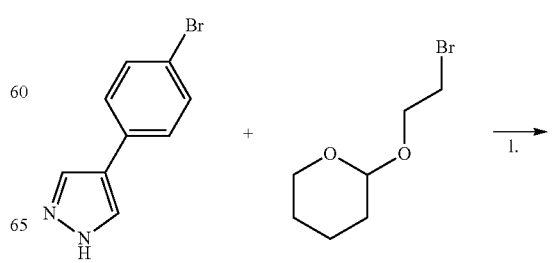

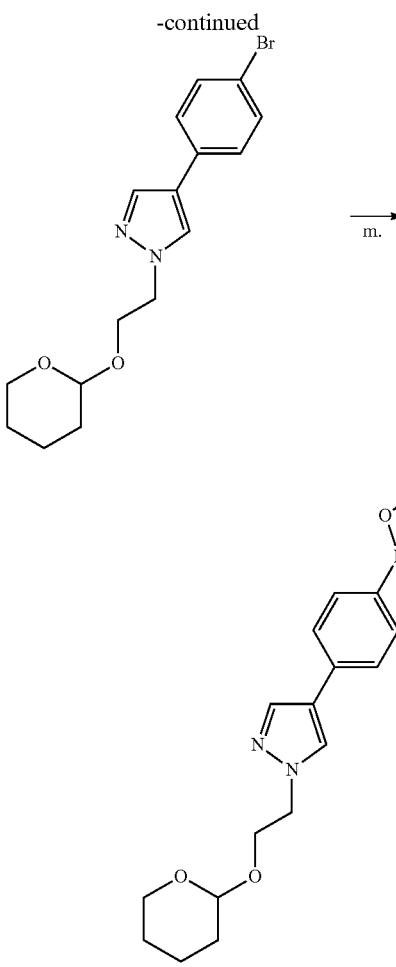

7l. 4-(4-Bromo-phenyl)-1-[2-(tetrahydro-pyran-2-yloxy)-ethyl]-1H-pyrazole 4-(4-Bromophenyl)pyrazole (2.00 g, 8.97 mmol) was dissolved in acetonitrile (300 mL). Cesium carbonate (4.38 g, 13.4 mmol) and 2-(2-bromo-ethoxy)-tetrahydro-pyran (96%, 2.54 g, 11.7 mmol) were added and the mixture was stirred overnight at RT. Subsequently, the mixture was stirred for 24 hours at 70° C. The pale yellow reaction mixture was filtered over Celite and washed with ethyl acetate. The filtrate was evaporated to dryness and used in the next step without further purification to yield in a yellow oil (94% purity, 3.10 g, 8.31 mmol, 93%).

7m. 1-[2-(Tetrahydro-pyran-2-yloxy)-ethyl]-4-[4-(4,4,5,5-tetramethyl-[1,3,2]dioxaborolan-2-yl)-phenyl]-1H-pyrazole

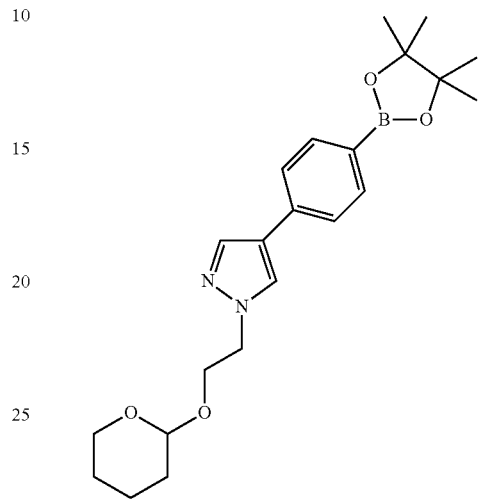

4-(4-Bromo-phenyl)-1-[2-(tetrahydro-pyran-2-yloxy)-ethyl]-1H-pyrazole (93%, 3.10 g, 8.31 mmol) was dissolved in THF (100 mL) and bis(pinacolato)diboron (4.22 g, 16.6 mmol), potassium acetate (2.45 g, 24.9 mmol) and (1,1'-bis(diphenylphosphino)ferrocene)-palladium dichloride dichloromethane complex (664 mg, 0.83 mmol) were added and the mixture was stirred under nitrogen atmosphere at 70° C. overnight. The reaction mixture was diluted with ethyl acetate, filtered and evaporated. The dark brown residue was purified by flash chromatography (dichloromethane/methanole) to yield in 2.35 g (94% purity, 5.55 mmol, 67%) of a yellow, viscous oil.

The THP-protecting group was cleaved off at the conditions used to deprotect the amino function of the pyridine applying TFA as described in 3f.

Preparation of (3-amino-1H-indazol-6-yl) boronic acid

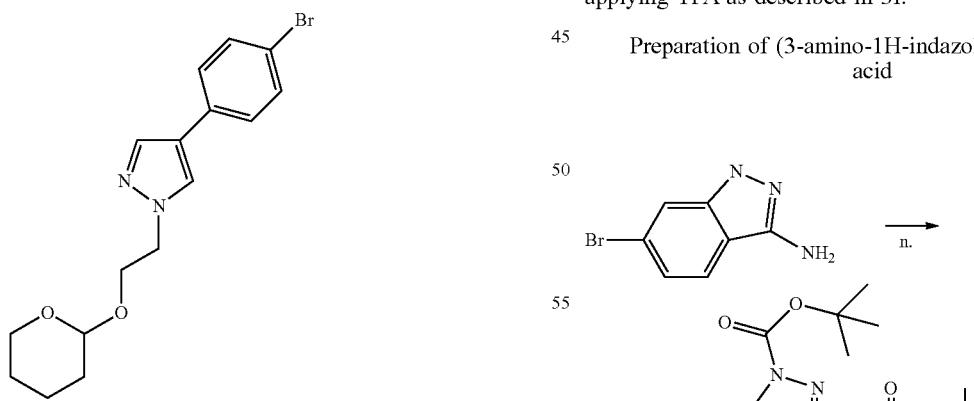

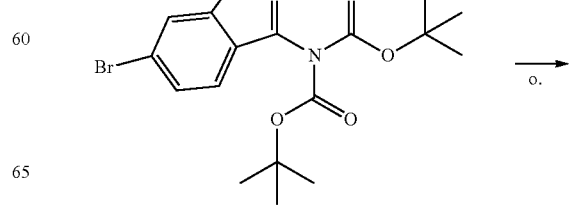

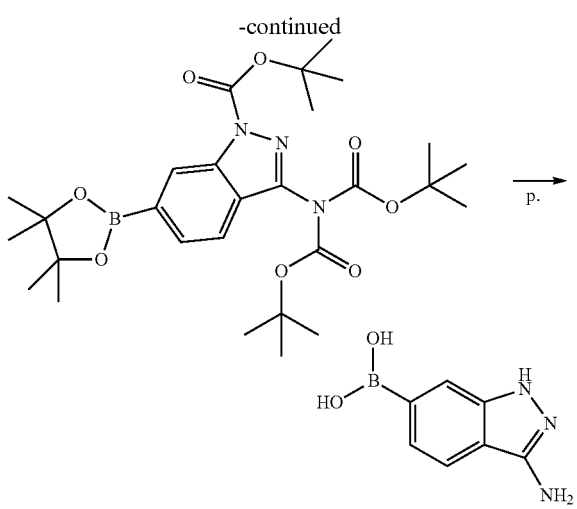

7n. tert-Butyl 3-[bis(tert-butoxycarbonyl)amino]-6-bromo-indazole-1-carboxylate

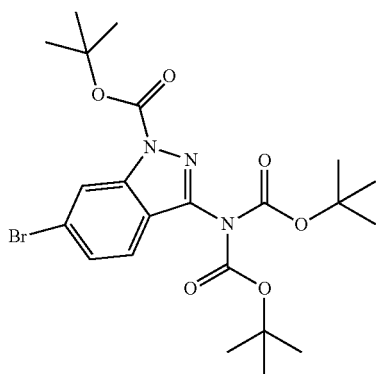 [SMILES: CC(C)(C)OC(=O)N(C(=O)OC(C)(C)C)c1nn(C(=O)OC(C)(C)C)c2cc(Br)ccc12]

6-Bromo-1H-indazol-3-amine (500 mg, 2.36 mmol) was dissolved in THF (10 mL). Di-tert-butyl dicarbonate (2.52 mL, 11.8 mmol) and triethylamine (3.27 mL, 23.6 mmol) were added and the reaction as stirred 3 days at RT. The reaction mixture was poured into 100 ml of water. The mixture was extracted twice with ethyl acetate. The organic layer was washed with water, dried, filtered and evaporated to dryness to yield in 1.42 g (73% purity, 2.02 mmol, 86%) of a brown oil.

7o. tert-Butyl 3-[bis(tert-butoxycarbonyl)amino]-6-(4,4,5,5-tetramethyl-1,3,2-dioxaborolan-2-yl)indazole-1-carboxylate

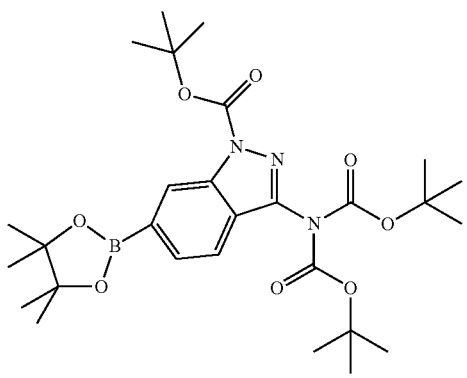 [SMILES: CC(C)(C)OC(=O)N(C(=O)OC(C)(C)C)c1nn(C(=O)OC(C)(C)C)c2cc(B3OC(C)(C)C(C)(C)O3)ccc12]

tert-Butyl 3-[bis(tert-butoxycarbonyl)amino]-6-bromo-indazole-1-carboxylate (86%, 1.14 g, 1.91 mmol) was dissolved in tetrahydrofuran (16 mL). Bis(pinacolato)diboron (486 mg, 1.91 mmol) and potassium acetate (375 mg, 3.83 mmol) were added. The mixture was degassed, (1,1'-bis(diphenylphosphino)ferrocene)-palladium dichloride dichloromethane complex (78.1 mg, 0.096 mmol) was added and the mixture was stirred under nitrogen atmosphere at 70° C. overnight. Additional bis(pinacolato)diboron (486 mg, 191 mmol), potassium acetate (130 mg, 1.33 mmol) and (1,1'-bis(diphenylphosphino)ferrocene)-palladium dichloride dichloromethane complex (78.1 mg, 0,096 mmol) were added and the reaction mixture was stirred under nitrogen atmosphere at 70° C. for 4 hours. The reaction mixture was diluted with ethyl acetate, filtered and evaporated. The dark brown residue was purified by flash chromatography (heptane/dichloromethane) to yield in 1.00 g (1.79 mmol, 94%) of a yellow glass like solid.

7p. (3-Amino-1H-indazol-6-yl)boronic acid

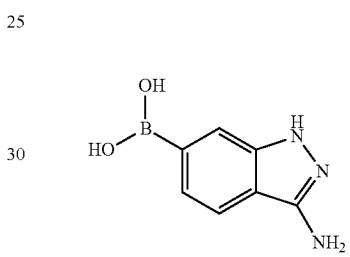

tert-Butyl 3-[bis(tert-butoxycarbonyl)amino]-6-(4,4,5,5-tetramethyl-1,3,2-dioxaborolan-2-yl)indazole-1-carboxylate (1 g, 1.79 mmol) was treated with hydrogen chloride solution (4M in dioxane, 5 mL, 20.0 mmol) in dioxane (25 mL). The pale yellow solution was stirred at room temperature overnight. The solution was evaporated to dryness and the residue was treated with diethyl ether to obtain an off-white solid. The mixture was filtered and washed with diethyl ether. The residue was dried overnight to result a pale brown solid (370 mg, 1.73 mmol, 97%) identified as HCl salt.

8. 8. 9-(2-amino-3-chloro-5-(4-(1-methyl-1H-pyrazol-4-yl)phenyl)pyridin-4-yl)-1,4,9-triazaspiro[5.5]undecan-5-one (40)

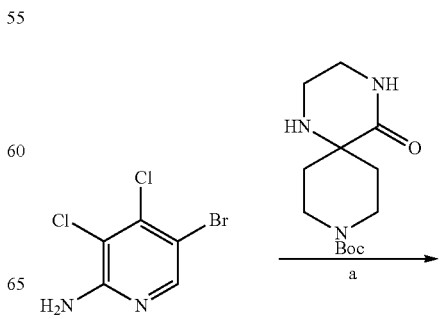

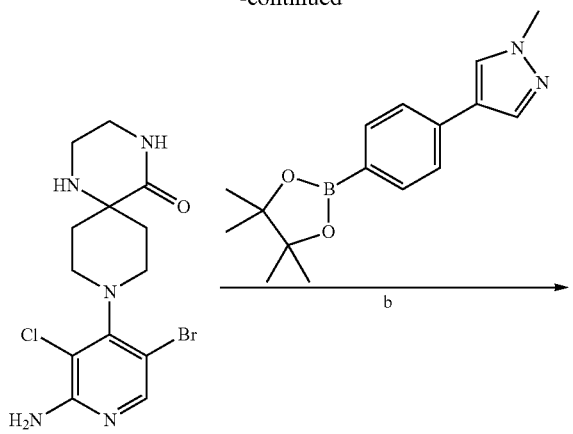

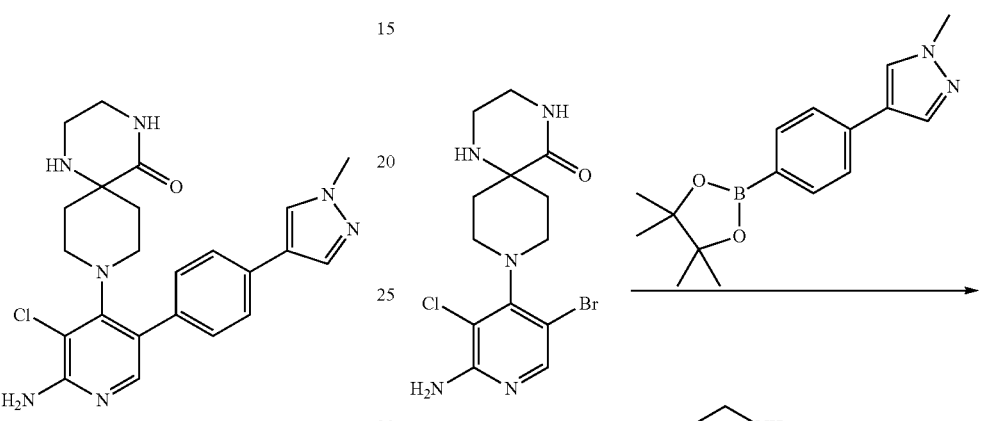

8a. 9-(2-Amino-5-bromo-3-chloropyridin-4-yl)-1,4,9-triazaspiro[5.5]undecan-5-one

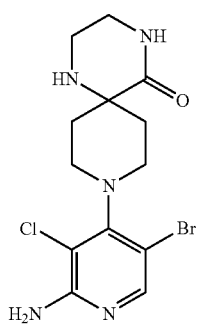 [SMILES: Nc1ncc(Br)c(N2CCC3(CC2)NCCNC3=O)c1Cl]

5-Bromo-3,4-dichloropyridin-2-amine (450 mg, 1.86 mmol), tert-butyl-5-oxo-1,4,9-triazaspiro[5.5]undecane-9-carboxylate (501 mg, 1.86 mmol) and potassium fluoride (216 mg, 3.72 mmol) were loaded in a microwave vial. The capped vial was evacuated using high vacuum and purged with nitrogen (each three times). Triethylamine (0.715 ml, 5.58 mmol) and NMP (4.5 mL) were added and the mixture was degassed again by using the high vacuum and purged with nitrogen again (each three times). The reaction mixture was heated in the microwave at 220° C. for 2 h. The dark brown solution was diluted with water and EtOAc and the organic layer was separated. The aqueous layer was extracted twice with EtOAc. The combined organic layers were washed with water, dried over MgSO₄, filtered and the solvent was evaporated under reduced pressure. The resulting brown oil was purified by chromatography on silica gel (CH₂Cl₂/EtOH) to give the product (380 mg, 55%) as a white solid. ¹H NMR (500 MHz, DMSO-d⁶) ppm=7.90 (s, 1H), 7.50 (s, 1H), 6.29 (bs, 2H), 3.53 (td, J=12.1, 2.1, 2H), 3.14 (td, J=5.4, 2.4, 2H), 2.92-2.81 (m, 4H), 2.31-2.25 (m, 1H), 2.11 (td, J=12.5, 3.7, 2H), 1.64-1.56 (m, 2H). HRMS m/z (ESI⁺) [M+H]⁺ C₁₃H₁₈BrClN₄₅O calc 374.0378, found 374.0374, Rt=0.61 min (HPLC method B).

8 b. 9-(2-Amino-3-chloro-5-(4-(1-methyl-1H-pyrazol-4-yl)phenyl)pyridin-4-yl)-1,4,9-triazaspiro[5.5]undecan-5-one (40)

1-Methyl-4-(4-(4,4,5,5-tetramethyl-1,3,2-dioxaborolan-2-yl)phenyl)-1H-pyrazole (45.5 mg, 0.16 mmol), 9-(2-amino-5-bromo-3-chloropyridin-4-yl)-1,4,9-triazaspiro[5.5]undecan-5-one (50.0 mg, 0.133 mmol) and tetrakis(triphenylphosphine) palladium(0) (7.70 mg, 6.67 µmol) were loaded in a microwave vial and then degassed acetonitrile (2.4 mL) and degassed 0.5 M aqueous sodium carbonate (374 µL, 0.156 mmol) were added. The reaction was heated at 120° C. under microwave irradiation for 60 min. Then, the reaction mixture was concentrated under reduced pressure and purified by column chromatography (DCM/EtOH). The obtained solid was triturated with hot EtOAc and filtered off. The solid was then dissolved in a mixture of DCM and MeOH and filtered on SCX-2 column. The product was released with 1M ammonia in MeOH to afford the title compound as a white solid (29.0 mg, 50%). ¹H NMR (500 MHz, DMSO-d⁶) ppm=8.17 (s, 1H), 7.89 (s, 1H), 7.60 (s, 1H), 7.59 (d, J=8.3, 2H), 7.42 (s, 1H), 7.22 (d, J=8.3, 2H), 6.06 (bs, 2H), 3.87 (s, 3H), 3.08-3.04 (m, 2H), 3.00-2.91 (m, 2H), 2.79-2.71 (m, 4H), 2.01-1.93 (m, 2H), 1.44-1.38 (m, 2H). HRMS m/z (ESI⁺) [M+H]⁺ C₂₃H₂₇ClN₇O calc 452.1960, found 452.1952, Rt=1.37 min (HPLC method B). According to this procedure also compounds 45 and 46 were synthesized.

9. 8-[2-amino-3-fluoro-5-(1-methyl-2,2-dioxo-2,3-dihydro-1H-2l6-benzo[c]isothiazol-5-yl)-pyridin-4-yl]-2,8-diaza-spiro[4.5]decan-1-one (61) and 8-[2-amino-3-fluoro-5-(1-methyl-2,2-dioxo-2,3-dihydro-1H-2l6-benzo[c]isothiazol-5-yl)-pyridin-4-yl]-1-oxa-3,8-diaza-spiro[4.5]decan-2-one (60)
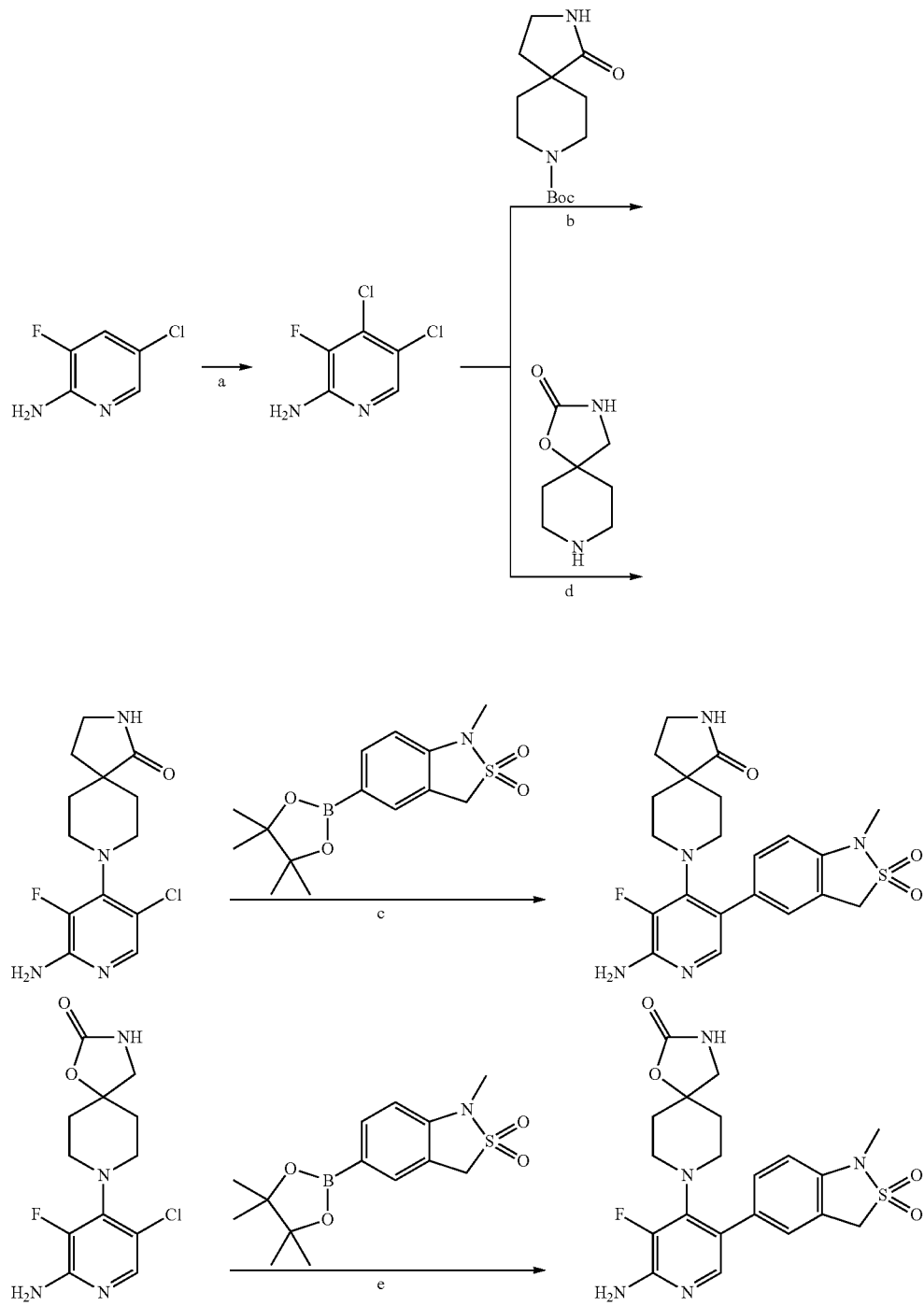

9a. 4,5-Dichloro-3-fluoropyridin-2-amine

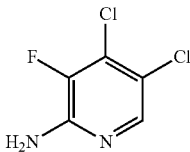

To a solution of LDA (8.0 mL, 15.93 mmol) in THF (31 mL) at −78° C. was added a solution of 5-chloro-3-fluoropyridin-2-amine (934 mg, 6.37 mmol) in THF (9.0 mL). After 50 min at −78° C., a solution of hexachloroethane (1.40 mL, 12.75 mmol) in THF (9.0 mL) was added. The reaction mixture was stirred for 40 min before being quenched with NH$_4$Cl. The layers were separated and the aqueous layer was extracted twice with DCM. The combined organic layers were dried over MgSO$_4$, filtered and the solvent was evaporated under reduced pressure. The crude mixture was purified by chromatography on silica gel (DCM) to give the title compound (950 mg, 82%) as a white solid. $^1$H NMR (500 MHz, CDCl$_3$) ppm=7.92 (d, J=0.9, 1H), 4.74 (s, 2H). LC-MS (ESI, m/z) Rt=2.66 min-180 (M+H)$^+$ (HPLC method B).

9b. 8-(2-Amino-5-chloro-3-fluoropyridin-4-yl)-2,8-diazaspiro[4.5]decan-1-one

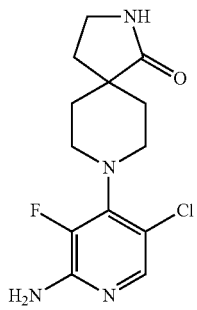 [SMILES: Nc1ncc(Cl)c(N2CCC3(CCNC3=O)CC2)c1F]

4,5-Dichloro-3-fluoropyridin-2-amine (100 mg, 0.55 mmol) and tert-butyl 1-oxo-2,8-diazaspiro[4.5]decane-8-carboxylate (211 mg, 0.83 mmol) were introduced in a microwave vial and then NMP (1.4 mL) was added. The vial was sealed and placed under high vacuum until effervescence ceased. After three vacuum/argon cycles, triethylamine (230 μL, 1.69 mmol) was added and the reaction mixture was heated in the microwave at 220° C. for 2 h. The reaction mixture was concentrated and the crude was purified by chromatography on silica gel (DCM/EtOH) to give the title compound (105 mg, 64%) as a white solid. $^1$H NMR (500 MHz, DMSO-d$^6$) ppm=7.67 (s, 1H), 7.59 (s, 1H), 6.17 (s, 2H), 3.34-3.27 (m, 2H), 3.19 (t, J=6.8, 2H), 3.12-3.05 (m, 2H), 2.01 (t, J=6.8, 2H), 1.83-1.76 (m, 2H), 1.44-1.38 (m, 2H). LC-MS (ESI, m/z) Rt=1.73 min-299 (M+H)$^+$ (HPLC method B).

9c. 8-[2-Amino-3-fluoro-5-(1-methyl-2,2-dioxo-2,3-dihydro-1H-2l6-benzo[c]isothiazol-5-yl)-pyridin-4-yl]-2,8-diaza-spiro[4.5]decan-1-one (61)

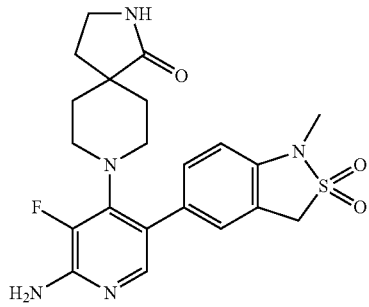

8-(2-Amino-5-chloro-3-fluoropyridin-4-yl)-2,8-diazaspiro[4.5]decan-1-one (20 mg, 6.7 μmol), 1-methyl-5-(4,4,5,5-tetramethyl-1,3,2-dioxaborolan-2-yl)-1,3-dihydrobenzo[c]isothiazole 2,2-dioxide (27 mg, 8.7 μmol) and trans-dichlorobis(tricyclohexylphosphine)palladium (2.50 mg, 3.35 μmol) were loaded in a microwave vial and then degassed acetonitrile (1.1 mL) and degassed 0.5 M aqueous sodium carbonate (187 μL, 9.4 μmol) were added. The reaction mixture was heated at 150° C. under microwave irradiation for 30 min. The solvent was evaporated and the product was purified by column chromatography (DCM/EtOH) to afford the title compound as a white solid (17 mg, 57%). $^1$H NMR (500 MHz, DMSO-d$^6$) ppm=7.54 (s, 1H), 7.48 (s, 1H), 7.45 (s, 1H), 7.41 (d, J=8.2, 1H), 6.97 (d, J=8.2, 1H), 6.02 (s, 2H), 4.67 (s, 2H), 3.13 (t, J=6.8, 2H), 3.07 (s, 3H), 3.07-3.01 (m, 2H), 2.92-2.86 (m, 2H), 1.91 (t, J=6.8, 2H), 1.60-1.53 (m, 2H), 1.20-1.15 (m, 2H). HRMS m/z (ESI$^+$) [M+H]$^+$ C$_{21}$H$_{25}$FN$_5$O$_3$S, calc 446.1657, found 446.1656, Rt=1.73 min (HPLC method B).

According to this procedure also compound 64 was synthesized.

9d. 8-(2-Amino-5-chloro-3-fluoropyridin-4-yl)-1-oxa-3,8-diazaspiro[4.5]decan-2-one

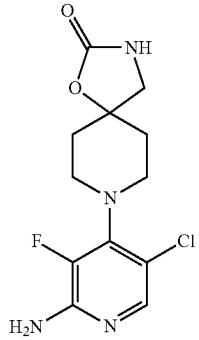 [SMILES: Nc1ncc(Cl)c(N2CCC3(CC2)CNC(=O)O3)c1F]

4,5-Dichloro-3-fluoropyridin-2-amine (100 mg, 0.55 mmol) and 1-oxa-3,8-diazaspiro[4.5]decan-2-one, acetate salt (178 mg, 0.83 mmol) were introduced in a microwave vial and then NMP (1.4 mL) was added. The vial was sealed and placed under high vacuum until effervescence ceased. After three vacuum/argon cycles, triethylamine (233 μL, 1.66 mmol) was added and the reaction mixture was heated in the microwave at 220° C. for 5 h. The reaction mixture was concentrated and the solid was washed with DCM and then with MeOH to give the title compound (60 mg, 36%) as a white solid. $^1$H NMR (500 MHz, DMSO-d$^6$) ppm=7.68 (s, 1H), 7.55 (s, 1H), 6.21 (s, 2H), 3.31 (s, 2H), 3.31-3.24 (m, 2H), 3.21-3.14 (m, 2H), 1.92-1.81 (m, 4H). LC-MS (ESI, m/z) Rt=1.63 min-301 (M+H)$^+$ (HPLC method B).

9e. 8-[2-Amino-3-fluoro-5-(1-methyl-2,2-dioxo-2,3-dihydro-1H-2l6-benzo[c]isothiazol-5-yl)-pyridin-4-yl]-1-oxa-3,8-diaza-spiro[4.5]decan-2-one (60)

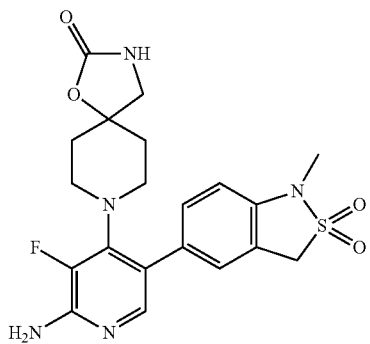 [SMILES: CN1c2ccc(-c3cnc(N)c(F)c3N3CCC4(CC3)CNC(=O)O4)cc2CS1(=O)=O]

8-(2-Amino-5-chloro-3-fluoropyridin-4-yl)-1-oxa-3,8-diazaspiro[4.5]decan-2-one (30 mg, 0.10 mmol), 1-methyl-5-(4,4,5,5-tetramethyl-1,3,2-dioxaborolan-2-yl)-1,3-dihydrobenzo[c]isothiazole 2,2-dioxide (62.0 mg, 0.20 mmol) and trans-dichlorobis(tricyclohexylphosphine)palladium (3.7 mg, 4.99 μmol) were loaded in a microwave vial. Degassed acetonitrile (1.7 mL) and degassed 0.5 M aqueous sodium carbonate (280 μL, 0.14 mmol) were then added. The reaction was heated at 150° C. under microwave irradiation for 30 min. Then, the reaction mixture was concentrated and purified by column chromatography (DCM/EtOH) to afford the title compound as a white solid (15 mg, 34%). $^1$H NMR (500 MHz, DMSO-d$^6$) ppm=7.484 (s, 1H), 7.477 (s, 1H), 7.44-7.41 (m, 2H), 6.98 (d, J=8.8, 1H), 6.06 (s, 2H), 4.69 (s, 2H), 3.22 (s, 2H), 3.11-3.03 (m, 2H), 3.06 (s, 3H), 2.96-2.90 (m, 2H), 1.70-1.56 (m, 4H). HRMS m/z (ESI$^+$) [M+H]$^+$ $C_{20}H_{23}FN_5O_4S$, calc 448.1449, found 448.1447, Rt=1.63 min (HPLC method B).

According to this procedure also compound 63 was synthesized.

10. 8-[2-amino-3-chloro-5-(2-ethyl-1,1-dioxo-2,3-dihydro-1H-1l6-benzo[d]isothiazol-5-yl)-pyridin-4-yl]-2,8-diaza-spiro[4.5]decan-1-one (68)

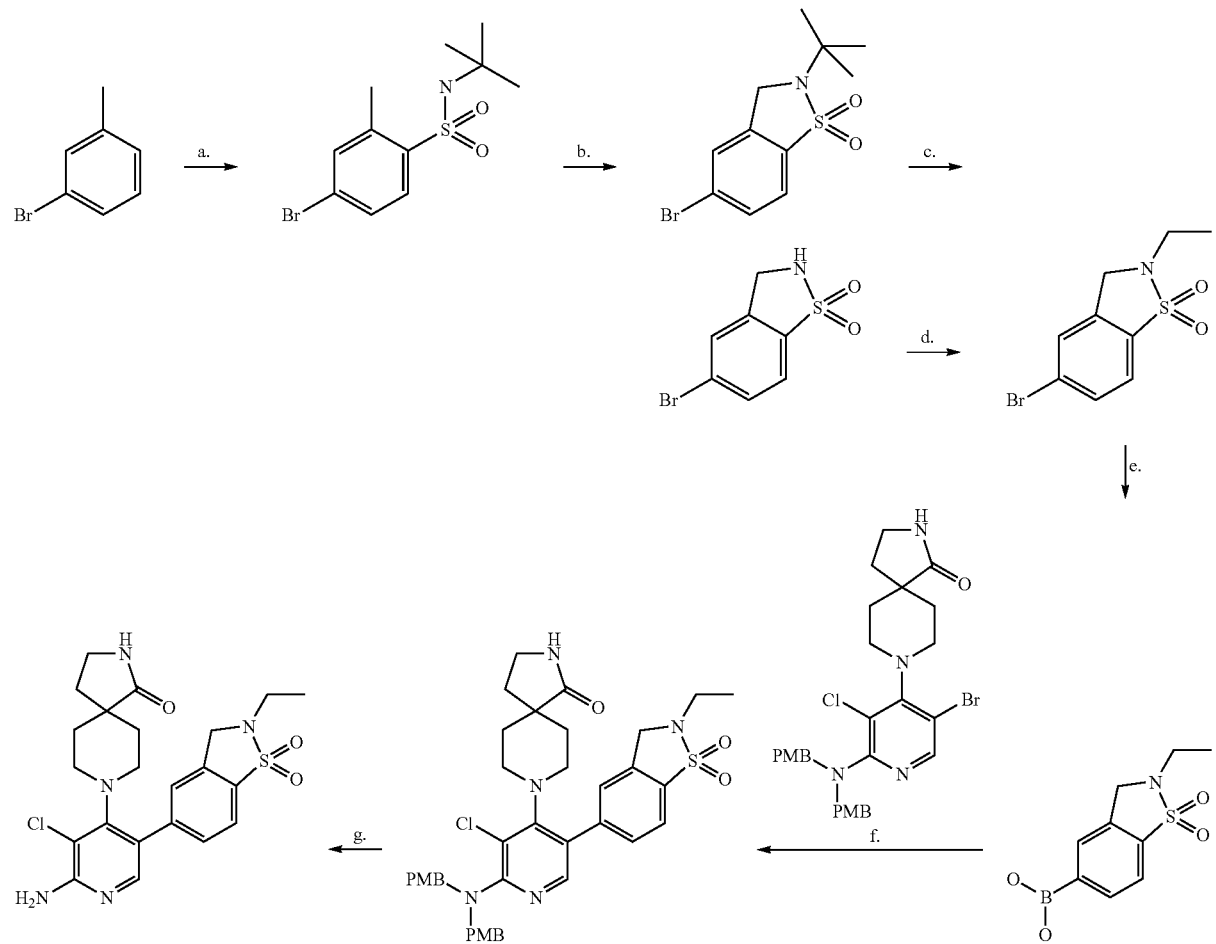

10a. 4-Bromo-N-(tert-butyl)-2-methylbenzenesulfonamide

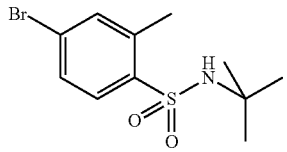 [SMILES: Cc1cc(Br)ccc1S(=O)(=O)NC(C)(C)C]

In a 100 mL three necked flask under N₂ containing 3-bromotoluene (3.55 mL, 29.2 mmol) dissolved in anhydrous DCM (50 mL) at −20° C. (dry ice bath with CH₃CN) was added chlorosulfonic acid (13.7 mL, 205 mmol) dropwise over 15 min. The reaction mixture was stirred under N₂ for 2 h at 0° C. and 4 h at RT. The reaction mixture was poured cautiously on ice and the resulting suspension was extracted with DCM (3 times 80 mL). The combined organic phases were washed with cold saturated brine, dried over MgSO₄, filtered and concentrated until 50 mL was reached.

To a 100 mL three necked flask under N₂ containing triethylamine (4.27 mL, 30.7 mmol) and tert-butylamine (3.23 mL, 30.7 mmol) dissolved in anhydrous DCM (30 mL) at RT, was added the solution of sulfonyl chloride prepared above. Addition was done over 20 minutes keeping the temperature below 20° C. The reaction mixture was stirred for 15 h at RT until completion.

The mixture was washed with HCl (0.1 N, 100 mL), a saturated solution of NaHCO₃, and brine. Then drying over MgSO₄, filtration and concentration gave the title compound (8.09 g, 90%) as yellowish solid.

10b. 5-Bromo-2-tert-butyl-2,3-dihydro-1,2-benzisothiazole 1,1-dioxide

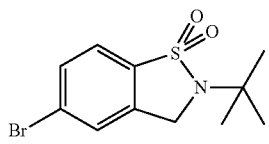 [SMILES: CC(C)(C)N1Cc2cc(Br)ccc2S1(=O)=O]

In a 150 mL flask containing 4-bromo-N-(tert-butyl)-2-methylbenzenesulfonamide (8.09 g, 26.4 mmol) in CHCl₃ (40 mL) at RT, N-bromosuccinimide (4.70 g, 26.4 mmol) was added in one portion followed by α,α'-azoisobutyronitrile (86.8 mg, 0.53 mmol). The reaction mixture was stirred for 16 h at reflux.

After concentration and dilution in MeOH (40 mL), sodium hydroxide (2.11 g, 52.8 mmol) was added and the reaction mixture was stirred for 3 h at RT under vigorous agitation. The mixture was poured into water and the resulting suspension was filtered to give a white solid, which was washed with diethyl ether and dried to give the title compound (1.72 g, 21.4%) as white solid.

10c. 5-Bromo-2,3-dihydro-benzo[d]isothiazole 1,1-dioxide

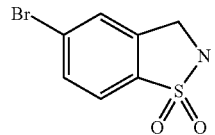 [SMILES: O=S1(=O)NCc2cc(Br)ccc21]

In a screw-capped-vial 5-bromo-2-tert-butyl-2,3-dihydro-benzo[d]isothiazole 1,1-dioxide (388 mg, 1.28 mmol) was dissolved in trifluoroacetic acid (6 mL) and stirred at 50° C. for 16 h. The mixture was evaporated to dryness. The pale beige residue was purified by flash-chromatography (n-heptane/DCM) to yield in 316 mg (1.28 mmol, 100%) of an off-white solid. Rt=2.063 min (HPLC method A)

10d. 5-Bromo-2-ethyl-2,3-dihydro-benzo[d]isothiazole 1,1-dioxide

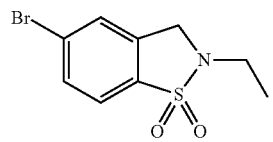

In a 12 mL screw-capped vessel 5-bromo-2,3-dihydro-benzo[d]isothiazole 1,1-dioxide (316 mg, 1.28 mmol) was dissolved in DMF (8 mL), potassium carbonate (0.44 g, 3.20 mmol) and iodoethane (399 mg, 2.56 mmol) were added and the reaction mixture was stirred at RT for 2 days. The mixture was treated with 50 mL water. The white precipitate formed was filtered under vacuum and washed with water. The solid was dissolved in DCM, filtered through a phase-separator and evaporated to dryness to give 246 mg (60%) of the title compound as an off-white solid. Rt=2.477 min (HPLC method A).

10e. 5-Dihydroxyboryl-2-ethyl-2,3-dihydro-benzo[d]isothiazole 1,1-dioxide

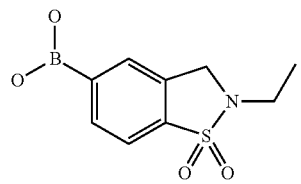 [SMILES: CCN1Cc2cc(B(O)O)ccc2S1(=O)=O]

In a 50 mL screw-capped vessel 5-bromo-2-ethyl-2,3-dihydro-benzo[d]isothiazole 1,1-dioxide (246 mg, 0.89 mmol) was dissolved in tetrahydrofuran (max. 0.0075% H₂O, 15 mL). Bis(pinacolato)diboron (339 mg, 1.34 mmol), potassium acetate (262 mg, 2.67 mmol) and Pd(dppf) Cl₂.CH₂Cl₂ (72.7 mg, 0.089 mmol) were added. The red reaction mixture was stirred at 70° C. for 16 h. The dark brown reaction mixture was treated with ethyl acetate, filtered and evaporated. The crude residue was purified by flash-chromatography (n-heptane/DCM) to give 107 mg (45%) of the title compound as a white solid. Rt=1.82 min (HPLC method A).

10f. 8-[2-[Bis-(4-methoxy-benzyl)-amino]-3-chloro-5-(2-ethyl-1,1-dioxo-2,3-dihydro-1H-1lambda6-benzo[d]isothiazol-5-yl)-pyridin-4-yl]-2,8-diaza-spiro[4.5]decan-1-one

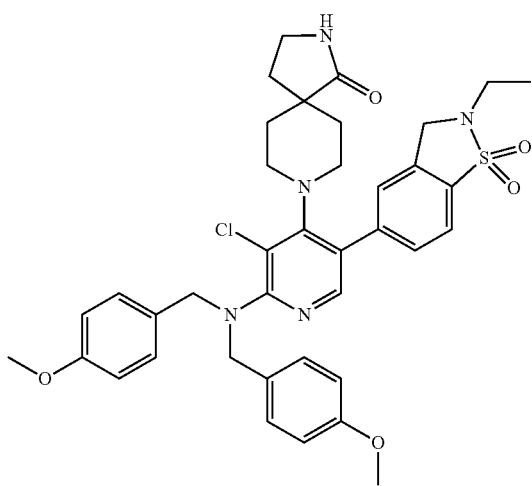 [SMILES: CCN1Cc2cc(-c3cnc(N(Cc4ccc(OC)cc4)Cc4ccc(OC)cc4)c(Cl)c3N3CCC4(CCNC4=O)CC3)ccc2S1(=O)=O]

In a microwave vial 8-{2-[bis-(4-methoxy-benzyl)-amino]-5-bromo-3-chloro-pyridin-4-yl}-2,8-diaza-spiro[4.5]decan-1-one (188 mg, 0.25 mmol) was suspended in acetonitrile (4 mL). 5-Bromo-2,3-dihydro-benzo[d]isothiazole 1,1-dioxide (67.0 mg, 0.25 mmol), sodium carbonate solution (1 mL, 0.50 mmol) and Pd(dppf)Cl$_2$·CH$_2$Cl$_2$ (18.3 mg, 0.025 mmol) were added. The closed vial was evacuated and flushed 3 times with nitrogen and agitated in the microwave oven (Emrys Optimizer) at 120° C. for 1 h. The reaction mixture was treated with ethyl acetate, filtered and evaporated. The crude brown residue was purified by flash-chromatography (n-heptane/DCM/MeOH) to give 167 mg (67%) of the title compound as a white solid. Rt=2.953 min (HPLC method A).

10g. 8-[2-Amino-3-chloro-5-(2-ethyl-1,1-dioxo-2,3-dihydro-1H-1l6-benzo[d]isothiazol-5-yl)-pyridin-4-yl]-2,8-diaza-spiro[4.5]decan-1-one (68)

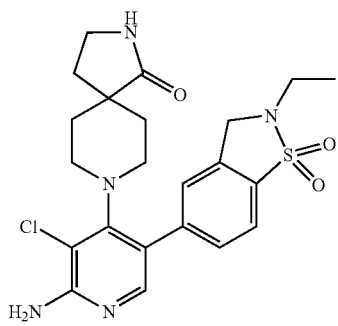 [SMILES: CCN1Cc2cc(-c3cnc(N)c(Cl)c3N3CCC4(CCNC4=O)CC3)ccc2S1(=O)=O]

In a 100 mL-roundbottom-flask 8-[2-[bis-(4-methoxy-benzyl)-amino]-3-chloro-5-(2-ethyl-1,1-dioxo-2,3-dihydro-1H-1lambda6-benzo[d]isothiazol-5-yl)-pyridin-4-yl]-2,8-diaza-spiro[4.5]decan-1-one (167 mg, 0.168 mmol) was dissolved in trifluoroacetic acid (3 mL). The dark red reaction solution was stirred overnight at RT. The reaction mixture was evaporated. The red residue was dissolved in DCM. Water and solid sodium carbonate was added to adjust the pH=9. It was filtered through a phase-separator and the DCM layer was evaporated. The brown residue was treated with acetonitrile to obtain a white precipitate. The reaction mixture was filtered under vacuum, washed with acetonitrile and diethyl ether and dried for 2 h in vacuum to give 43 mg (53%) of the title compound as a white solid. 1H NMR (500 MHz, DMSO-d6) ppm=7.85 (d, J=8.0, 1H), 7.70 (s, 1H), 7.58-7.52 (m, 1H), 7.50 (s, 1H), 7.49-7.44 (m, 1H), 6.28 (s, 2H), 4.50 (s, 2H), 3.35-3.23 (m, 4H), 3.12 (t, J=6.8, 2H), 3.04-2.93 (m, 2H), 1.86 (t, J=6.8, 2H), 1.72-1.60 (m, 2H), 1.28 (t, J=7.2, 3H), 1.25-1.18 (m, 2H). HPLC: (percent area) 100%; Rt=1.93 min (HPLC method A).

11. Racemic trans-2'-amino-3'-chloro-3-hydroxy-5'-(1-methyl-2,2-dioxo-2,3-dihydro-1H-2l6-benzo[c]isothiazol-5-yl)-3,4,5,6-tetrahydro-2H-[1,4]bipyridinyl-4-carbonitrile (57)

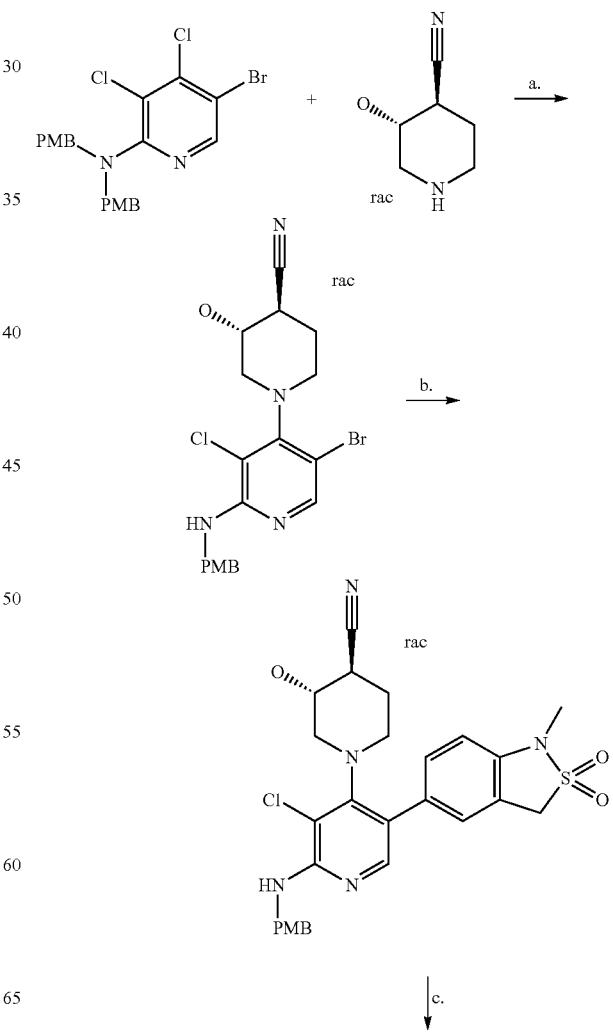

-continued

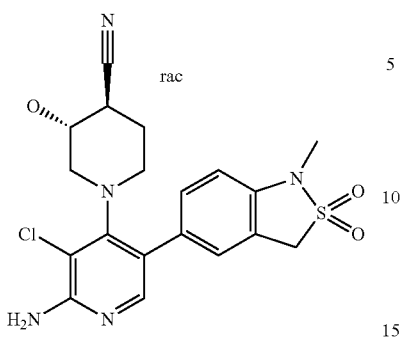

11a. Racemic trans-5'-bromo-3'-chloro-3-hydroxy-2'-(4-methoxy-benzylamino)-3,4,5,6-tetrahydro-2H-[1,4']bipyridinyl-4-carbonitrile

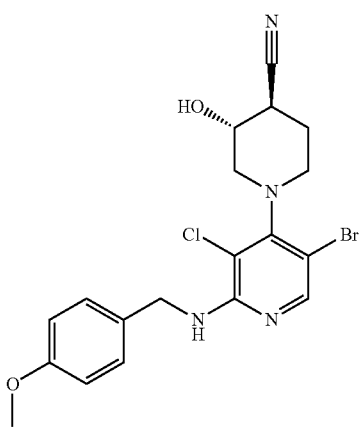 [SMILES: COc1ccc(CNc2ncc(Br)c(N3CC[C@H](C#N)[C@@H](O)C3)c2Cl)cc1]

In a 15 mL tube for microwave synthesis 5-bromo-3,4-dichloro-pyridin-2-yl)-bis-(4-methoxy-benzyl)-amine (1.00 g, 2.07 mmol) and racemic trans-4-cyano-3-hydroxy-piperidine-1-carboxylic acid tert-butyl ester (493 mg, 2.18 mmol) were dissolved in 1-methyl-2-pyrrolidone (5 mL) and triethylamine (0.57 mL, 4.15 mmol) was added at RT. The tube was sealed, evacuated and flushed with nitrogen. The reaction mixture was stirred in the microwave for 2 h at 220° C. HPLC/MS showed the desired product mass and the mass of the mono-protected PMB product but also starting material.

The mixture was heated for further 8 h at 220° C. in the microwave oven: no starting material was detected, only the mass of the mono-PMB product. The solvent was evaporated, the residue was dissolved in ethyl acetate and the organic layer was washed three times with water, then with brine, dried with sodium sulfate and the solvent was evaporated. The crude product was purified by flash chromatography to give 205 mg (13%) of the title compound as an off-white solid.

11b. Racemic trans-3'-chloro-3-hydroxy-2'-(4-methoxy-benzylamino)-5'-(1-methyl-2,2-dioxo-2,3-dihydro-1H-2lambda6-benzo[c]isothiazol-5-yl)-3,4,5,6-tetrahydro-2H-[1,4']bipyridinyl-4-carbonitrile

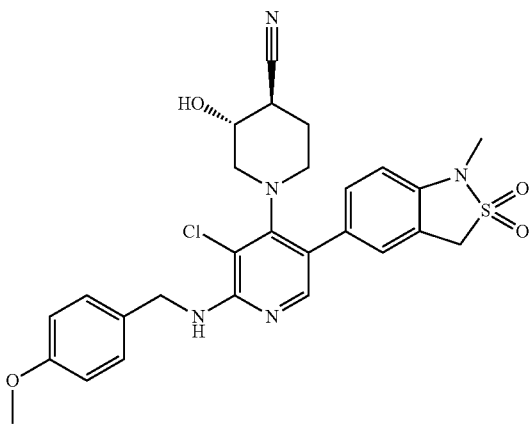 [SMILES: COc1ccc(CNc2ncc(-c3ccc4c(c3)CS(=O)(=O)N4C)c(N3CC[C@H](C#N)[C@@H](O)C3)c2Cl)cc1]

A vessel for microwave synthesis was charged with racemic trans-5'-bromo-3'-chloro-3-hydroxy-2'-(4-methoxy-benzylamino)-3,4,5,6-tetrahydro-2H-[1,4']bipyridinyl-4-carbonitrile (100 mg, 0.133 mmol), 1-methyl-5-(4,4,5,5-tetramethyl-[1,3,2]dioxaborolan-2-yl)-1,3-dihydro-benzo[c]isothiazole 2,2-dioxide (50.3 mg, 0.159 mmol), potassium carbonate (36.7 mg, 0.266 mmol) and Pd(dppf)Cl$_2$.CH$_2$Cl$_2$ (5.42 mg, 0.007 mmol) and then acetonitrile (5 mL) and water (2 mL) were added. The mixture was stirred for 1 h in the microwave oven at 120° C. The solvent was evaporated, the residue was dissolved in acetonitrile and non-soluble salts were filtered off. The filtrate was evaporated and the crude product was purified by preparative chromatography. Clear fractions were combined and evaporated to give the 32.3 mg (42%) of the desired product as a colorless solid.

11c. Racemic trans-2'-amino-3'-chloro-3-hydroxy-5'-(1-methyl-2,2-dioxo-2,3-dihydro-1H-2l6-benzo[c]isothiazol-5-yl)-3,4,5,6-tetrahydro-2H-[1,4']bipyridinyl-4-carbonitrile (57)

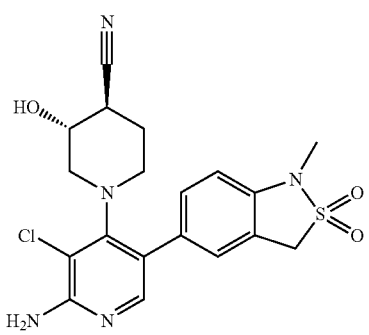 [SMILES: CN1c2ccc(-c3cnc(N)c(Cl)c3N3CC[C@H](C#N)[C@@H](O)C3)cc2CS1(=O)=O]

Racemic trans-3'-chloro-3-hydroxy-2'-(4-methoxy-benzylamino)-5'-(1-methyl-2,2-dioxo-2,3-dihydro-1H-2lambda6-benzo[c]isothiazol-5-yl)-3,4,5,6-tetrahydro-2H-[1,4']bipyridinyl-4-carbonitrile (32.3 mg, 0.055 mmol) was dissolved in trifluoroacetic acid (3 mL) and stirred 1 h at RT (yellow solution turned into red). The mixture was allowed to stir 16 h at RT. The trifluoroacetic acid was evaporated under reduced pressure and the residue was purified by preparative chromatography. The residue was dissolved again in ethyl acetate and washed once with saturated $Na_2CO_3$ solution to give the free base, dried with sodium sulfate, evaporated and freeze dried to get 17.3 mg (72%) of the desired product as colorless solid. 1H NMR (500 MHz, DMSO-d6) ppm=7.63 (s, 1H), 7.24-7.15 (m, 2H), 6.98 (d, J=8.1, 1H), 6.15 (s, 2H), 5.60 (d, J=5.4, 1H), 4.68 (s, 2H), 3.68-3.38 (m, 1H), 3.14-3.01 (m, 4H), 2.96-2.83 (m, 1H), 2.65-2.22 (m, 3H), 1.98-1.81 (m, 1H), 1.76-1.58 (m, 1H).

LC/MS: (percent area) 100%; Rt 1.372 min (HPLC method D).

According to this procedure compound 56 was synthesized.

Enantiomers were separated by chiral HPLC under standard conditions:
Machine: SFC MiniGram®
Column: Chiralpak AS-H, 250×4.6 mm
Eluent: CO2+30% Methanol+0.5% Diethylamin
Flow: 5 mL/min.
λ=220 nm
Sample injection: 100 µL/run (50 mg sample dissolved in 5 mL Methanol)
Rt (cpd 65)=4.20 min, 19.9 mg
Rt (cpd 66)=5.90 min, 21.2 mg New Boronic Esters 12. Preparation of 1-ethyl-4-(4-(4,4,5,5-tetramethyl-1,3,2-dioxaborolan-2-yl)phenyl)-1H-pyrazole and 1-isopropyl-4-(4-(4,4,5,5-tetramethyl-1,3,2-dioxaborolan-2-yl)phenyl)-1H-pyrazole 12a. 4-(4-(4,4,5,5-Tetramethyl-1,3,2-dioxaborolan-2-yl)phenyl)-1H-pyrazole

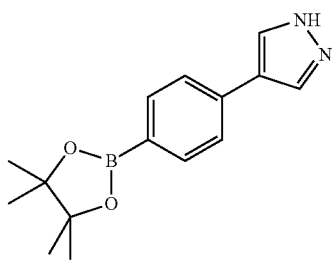

4-(4-Bromophenyl)-1H-pyrazole (1.00 g, 4.48 mmol), bis(pinacolate)diborane (1.70 g, 6.72 mmol), potassium acetate (1.32 g, 13.45 mmol) and Pd(dppf)Cl$_2$.CH$_2$Cl$_2$ (183 mg, 0.224 mmol) were loaded in a flask and DME (32.5 mL) was added. The reaction was heated at 80° C. overnight. Another 170 mg of Pd(dppf)Cl$_2$.CH$_2$Cl$_2$ were added and the reaction mixture was heated for another 30 h. After addition of water and DCM, the aqueous layer was extracted with DCM. The organic layers were dried over MgSO$_4$, filtered and the solvent was evaporated under reduced pressure. The crude was purified by chromatography on silica gel (cyclohexane/ethyl acetate) to give the title compound (820 mg, 68%) as a white solid. $^1$H NMR (500 MHz, CDCl$_3$) ppm=7.94 (s, 2H), 7.84 (d, J=8.2, 2H), 7.54 (d, J=8.2, 2H), 1.38 (s, 12H). LC-MS (ESI, m/z) Rt=2.94 min-271 (M+H)$^+$ (HPLC method B).

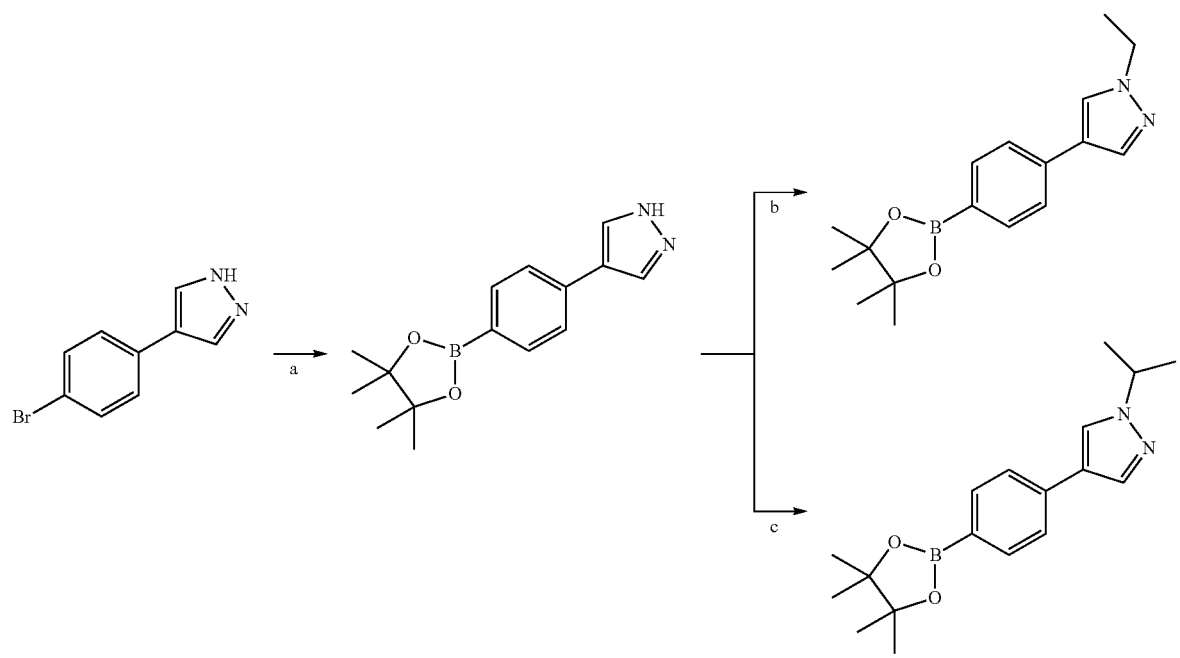 [SMILES: Brc1ccc(-c2cn[nH]c2)cc1 ; CC1(C)OB(c2ccc(-c3cn[nH]c3)cc2)OC1(C)C ; CC(C)n1cc(-c2ccc(B3OC(C)(C)C(C)(C)O3)cc2)cn1 ; CCn1cc(-c2ccc(B3OC(C)(C)C(C)(C)O3)cc2)cn1]

12b. 1-Ethyl-4-(4-(4,4,5,5-tetramethyl-1,3,2-dioxaborolan-2-yl)phenyl)-1H-pyrazole

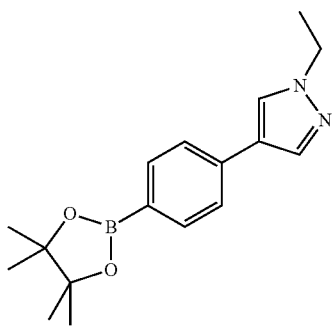 [SMILES: CCn1cc(-c2ccc(B3OC(C)(C)C(C)(C)O3)cc2)cn1]

To a solution of 4-(4-(4,4,5,5-tetramethyl-1,3,2-dioxaborolan-2-yl)phenyl)-1H-pyrazole (430 mg, 1.60 mmol) in DMF (8.0 mL) were added potassium carbonate (576 mg, 4.17 mmol) and iodoethane (340 μL, 4.17 mmol). The reaction mixture was stirred at RT overnight and then filtered and concentrated. The crude was purified by chromatography on silica gel (cyclohexane/ethyl acetate) to give the title compound (300 mg, 63%) as a white solid. 1H NMR (500 MHz, CDCl$_3$) ppm=7.83 (s, 1H), 7.81 (d, J=8.2, 2H), 7.69 (s, 1H), 7.50 (d, J=8.2, 2H), 4.20 (q, J=7.3, 2H), 1.53 (t, J=7.3, 3H), 1.36 (s, 12H). LC-MS (ESI, m/z) Rt=3.14 min-299 (M+H)$^+$ (HPLC method B).

12c. 1-Isopropyl-4-(4-(4,4,5,5-tetramethyl-1,3,2-dioxaborolan-2-yl)phenyl)-1H-pyrazole

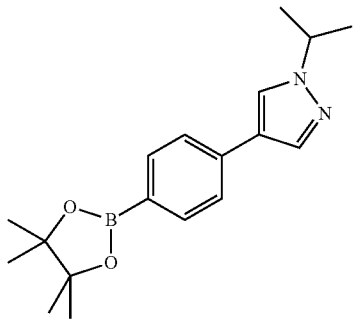 [SMILES: CC(C)n1cc(-c2ccc(B3OC(C)(C)C(C)(C)O3)cc2)cn1]

To a solution of 4-(4-(4,4,5,5-tetramethyl-1,3,2-dioxaborolan-2-yl)phenyl)-1H-pyrazole (390 mg, 1.43 mmol) in DMF (7.1 mL) was added potassium carbonate (515 mg, 3.72 mmol) and 2-iodopropane (180 μL, 1.80 mmol). The reaction was stirred at RT overnight. Another 180 μL of 2-iodopropane were added and the reaction mixture was stirred at RT for one day. The conversion was not complete at this stage therefore additional 360 μL of 2-iodopropane were added and the reaction mixture was stirred at RT for 2 days. It was then filtered and concentrated under reduced pressure. The crude was purified by chromatography on silica gel (cyclohexane/ethyl acetate) to give the title compound (150 mg, 34%) as a white solid. $^1$H NMR (500 MHz, CDCl$_3$) ppm=7.83 (s, 1H), 7.81 (d, J=8.2, 2H), 7.73 (s, 1H), 7.51 (d, J=8.2, 2H), 4.54 (septuplet, J=6.7, 1H), 1.56 (d, J=6.7, 6H), 1.37 (s, 12H). LC-MS (ESI, m/z) Rt=3.20 min-313 (M+H)$^+$ (HPLC method B).

13. Preparation of 1-ethyl-5-(4,4,5,5-tetramethyl-1,3,2-dioxaborolan-2-yl)-1,3-dihydrobenzo[c]isothiazole 2,2-dioxide, 1-isopropyl-5-(4,4,5,5-tetramethyl-1,3,2-dioxaborolan-2-yl)-1,3-dihydrobenzo[c]isothiazole 2,2-dioxide and 1-(cyclopropylmethyl)-5-(4,4,5,5-tetramethyl-1,3,2-dioxaborolan-2-yl)-1,3-dihydrobenzo[c]isothiazole 2,2-dioxide

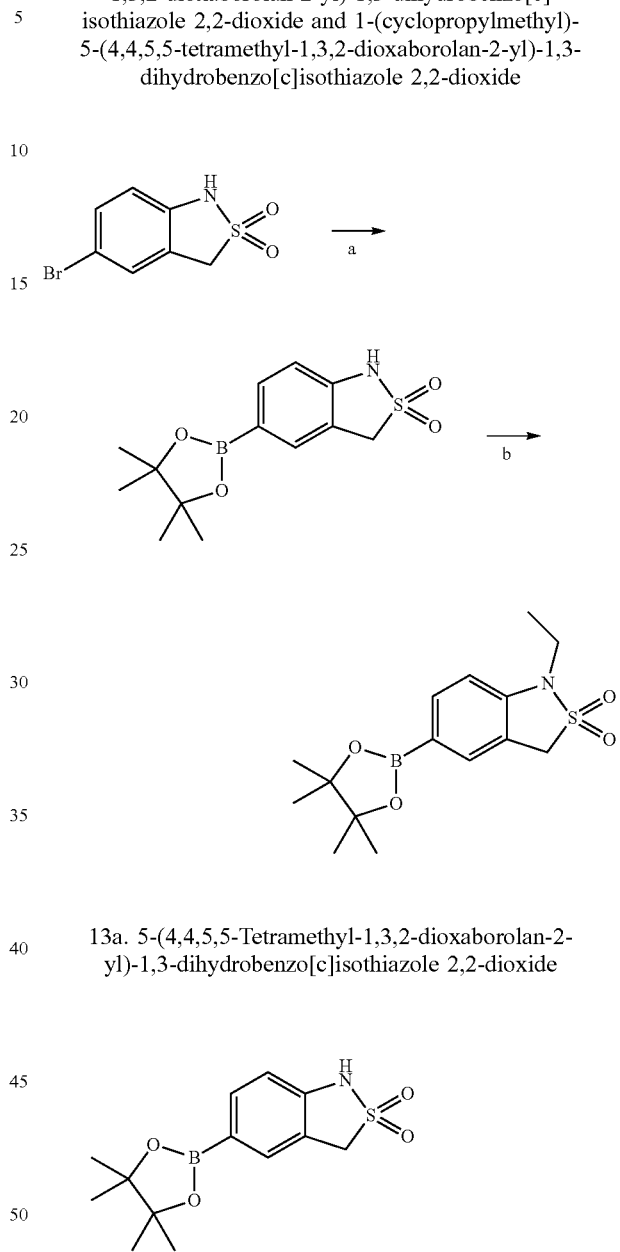

13a. 5-(4,4,5,5-Tetramethyl-1,3,2-dioxaborolan-2-yl)-1,3-dihydrobenzo[c]isothiazole 2,2-dioxide

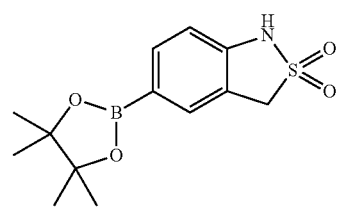 [SMILES: CC1(C)OB(c2ccc3c(c2)CS(=O)(=O)N3)OC1(C)C]

5-Bromo-1,3-dihydrobenzo[c]isothiazole 2,2-dioxide (500 mg, 2.02 mmol), bis(pinacolato)diboron (768 mg, 3.02 mmol), potassium acetate (593 mg, 6.05 mmol) and Pd(dppf)Cl$_2$.CH$_2$Cl$_2$ (82 mg, 0.10 mmol) were loaded in a microwave vial and DME (14.6 mL) was added. The reaction mixture was heated at 80° C. overnight. The solvent was evaporated and the crude was purified by column chromatography on silica gel (cyclohexane/acetone) to give the title compound (580 mg contaminated by 23% of pinacol, corrected yield 75%) as a white solid. $^1$H NMR (500 MHz, CDCl$_3$) ppm=7.72 (d, J=7.9, 1H), 7.68 (s, 1H), 7.85 (d, J=7.9, 1H), 6.79 (s, 1H), 4.37 (s, 2H), 1.33 (s, 12H). LC-MS (ESI, m/z) Rt=2.67 min-232 (M−SO2+H)$^+$ (HPLC method B).

13b. 1-Ethyl-5-(4,4,5,5-tetramethyl-1,3,2-dioxaborolan-2-yl)-1,3-dihydrobenzo[c]isothiazole 2,2-dioxide

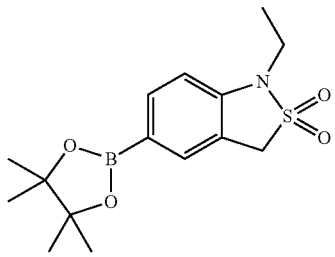 [SMILES: CCN1c2ccc(B3OC(C)(C)C(C)(C)O3)cc2CS1(=O)=O]

To 5-(4,4,5,5-tetramethyl-1,3,2-dioxaborolan-2-yl)-1,3-dihydrobenzo[c]isothiazole 2,2-dioxide (330 mg, 1.12 mmol) in DMF (7.0 mL) were added potassium carbonate (386 mg, 2.80 mmol) and iodoethane (180 μL, 2.24 mmol). The reaction mixture was stirred at RT overnight. The solvent was evaporated and the crude was purified by chromatography on silica gel (cyclohexane/acetone) to give the title compound (300 mg, 83%) as a white solid. $^1$H NMR (500 MHz, CDCl$_3$) ppm=7.79 (d, J=7.9, 1H), 7.69 (s, 1H), 6.75 (d, J=7.9, 1H), 4.33 (s, 2H), 3.73 (q, J=7.2, 2H), 1.42 (t, J=7.2, 3H), 1.35 (s, 12H). LC-MS (ESI, m/z) Rt=2.97 min-232 (M−SO$_2$+H)$^+$ (HPLC method B).

14. Preparation of 1-ethyl-6-(4,4,5,5-tetramethyl-1,3,2-dioxaborolan-2-yl)-1H-indazole

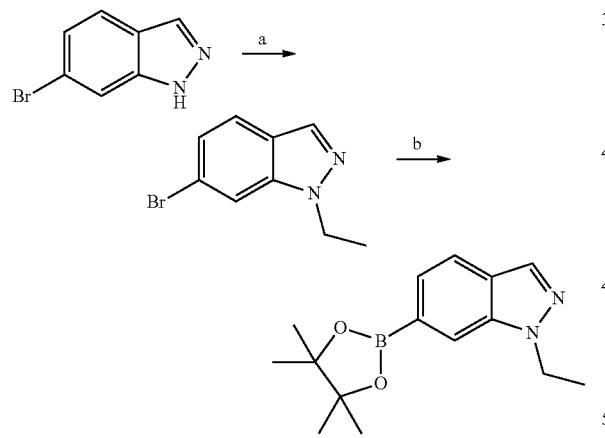

14a. 6-Bromo-1-ethyl-1H-indazole

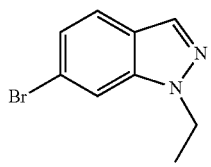

A mixture of 6-bromo-1H-indazole (500 mg, 2.54 mmol), bromo-ethane (0.379 mL, 5.08 mmol) and potassium carbonate (1052 mg, 7.61 mmol) in DMF (8 mL) was heated at 75° C. for 2 h. The mixture was diluted with water and EtOAc and the layers were separated. The aqueous layer was extracted with EtOAc three times. The combined organic layers were dried over MgSO$_4$ and concentrated in vacuum. The resulting brown oil was purified by column chromatography (cyclohexane/EtOAc) to afford the product (336 mg, 59%) as a white solid as well as the corresponding N2-indazole alkylated by-product (210 mg, 37%). $^1$H NMR (500 MHz, CDCl$_3$) ppm=7.97 (d, J=1.0, 1H), 7.61 (s, 1H), 7.60 (dd, J=8.5, 1.2, 1H), 7.25 (dd, J=8.5, 1.2, 1H), 4.40 (q, J=7.3, 2H), 1.52 (t, J=7.3, 3H). HRMS m/z (ESI$^+$) [M+H]$^+$ C$_9$H$_9$BrN$_2$, calc 225.0022, found 225.0020, Rt=2.98 (HPLC method B).

14b. 1-Ethyl-6-(4,4,5,5-tetramethyl-1,3,2-dioxaborolan-2-yl)-1H-indazole

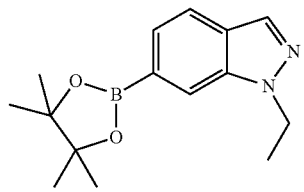 [SMILES: CCn1ncc2ccc(B3OC(C)(C)C(C)(C)O3)cc21]

A mixture of 6-bromo-1-ethyl-1H-indazole (325 mg, 1.444 mmol), bis(pinacolate)diborane (440 mg, 1.733 mmol), Pd(dppf)Cl$_2$.CH$_2$Cl$_2$ (52.8 mg, 0.072 mmol) and potassium acetate (425 mg, 4.33 mmol) in degassed DME (10 mL) was heated at 80° C. for 3 h. The mixture was concentrated under reduced pressure and purified by column chromatography (cyclohexane/EtOAc) to afford the product as a white solid (332 mg, 84%). $^1$H NMR (500 MHz, CDCl$_3$) ppm=8.00 (d, J=1.0, 1H), 7.94 (d, J=1.0, 1H), 7.74 (dd, J=8.0, 0.9, 1H), 7.57 (dd, J=8.0, 0.9, 1H), 4.50 (q, J=7.3, 2H), 1.54 (t, J=7.3, 3H), 1.40 (s, 12H). HRMS m/z (ESI$^+$) [M+H]$^+$ C$_{15}$H$_{21}$N$_2$O$_2$, calc 273.1769, found 273.1765, Rt=3.17 (HPLC method B).

15. Preparation of 1-isopropyl-5-(4,4,5,5-tetramethyl-1,3,2-dioxaborolan-2-yl)-1H-indazole

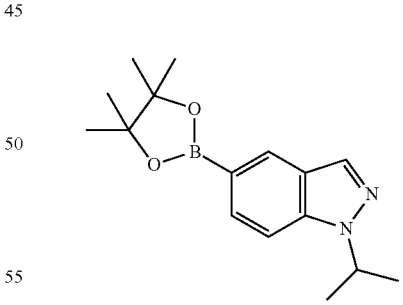

5-Bromo-1-isopropyl indazole (400 mg, 1.673 mmol), bis(pinacolate)diborane (552 mg, 2.175 mmol), Pd(dppf)Cl$_2$.CH$_2$Cl$_2$ (61.2 mg, 0.084 mmol) and potassium acetate (493 mg, 5.02 mmol) were loaded in a microwave vial, degassed DME (12 mL) was added and the mixture was heated at 80° C. in an oil bath overnight. The mixture was concentrated and purified by column chromatography (cyclohexane/EtOAc) to give the product as a colourless oil (382 mg, 80%). $^1$H NMR (500 MHz, CDCl$_3$) ppm=8.29 (s, 1H), 8.03 (s, 1H), 7.79 (dd, J=8.6, 1.1, 2H), 7.44 (d, J=8.6, 1H), 4.87 (p, J=6.7, 1H), 1.61 (d, J=6.7, 6H), 1.38 (s, 12H). HRMS m/z (ESI⁺) [M+H]⁺ $C_{16}H_{24}BN_2O_2$, calc 286.1962, found 286.1957, Rt=1.85 (HPLC method B).

16. Preparation of 1-Isopropyl-6-(4,4,5,5-tetramethyl-1,3,2-dioxaborolan-2-yl)-1H-indazole

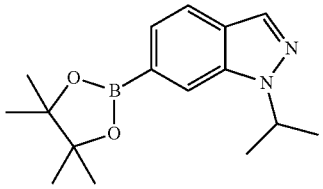 [SMILES: CC(C)n1ncc2ccc(B3OC(C)(C)C(C)(C)O3)cc21]

A mixture of 1H-indazole-6-boronic acid pinacol ester (500 mg, 2.048 mmol), 2-bromopropane (0.352 mL, 4.10 mmol) and potassium carbonate (849 mg, 6.15 mmol) in DMF (8 mL) was heated at 80° C. for 24 h. Additional 2-bromopropane (0.352 mL, 4.10 mmol) was added and the suspension was heated at 85° C. for 48 h before the mixture was diluted with water and EtOAc and the layers were separated. The aqueous layer was extracted with EtOAc three times. The combined organic layers were dried over MgSO₄ and concentrated under reduced pressure. The resulting brown oil was purified by column chromatography (cyclohexane/EtOAc) to afford the product as a white solid (232 mg, 40%) as well as the corresponding N2-indazole alkylated by-product (99 mg, 17%). ¹H NMR (500 MHz, CDCl₃) ppm=8.02 (d, J=1.0, 1H), 7.99 (d, J=1.0, 1H), 7.73 (dd, J=8.1, 1.0, 1H), 7.57 (dd, J=8.1, 1.0, 1H), 4.95 (p, J=6.7, 1H), 1.60 (s, 3H), 1.58 (s, 3H), 1.37 (s, 12H). HRMS m/z (ESI⁺) [M+H]⁺ $C_{16}H_{24}BN_2O_2$, calc 286.1962, found 286.1963, Rt=3.26 (HPLC method B).

17. Preparation of 2-methyl-1-{4-[4-(4,4,5,5-tetramethyl-[1,3,2]dioxaborolan-2-yl)-phenyl]-1-pyrazol-1-yl}-2-ol

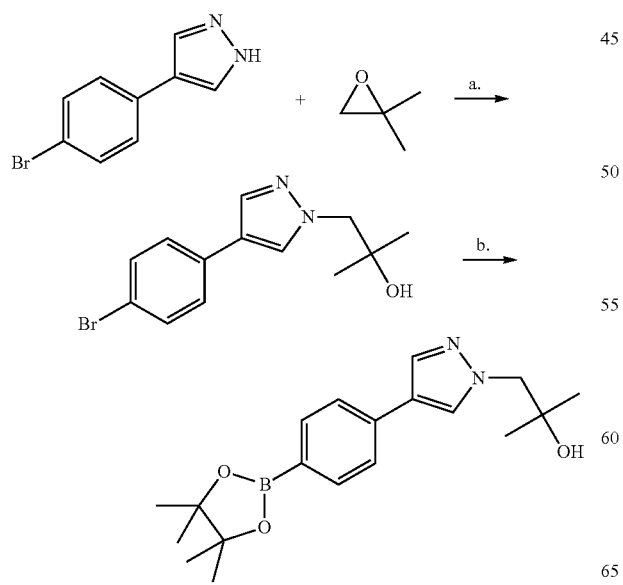

17a. 1-[4-(4-Bromo-phenyl)-pyrazol-1-yl]-2-methyl-propan-2-ol

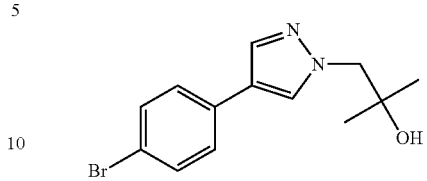

4-(4-Bromo-phenyl)-1H-pyrazole (500 mg, 2.24 mmol.) was dissolved in DMF (5 mL) in a heavy walled reaction tube. Potassium carbonate (435 mg, 3.14 mmol) and 2,2-dimethyl-oxirane (0.40 mL, 4.48 mmol) were added and the tube was sealed with a teflon screw cap and heated to 100° C. for 16 h. After cooling to RT, the reaction was diluted with water and extracted with ethyl acetate. The combined organic layers were dried over Na₂SO₄, filtered, and evaporated to yield in 660 mg (100%) white crystals.

17b. 2-Methyl-1-{4-[4-(4,4,5,5-tetramethyl-[1,3,2]dioxaborolan-2-yl)-phenyl]-pyrazol-1-yl}-propan-2-ol

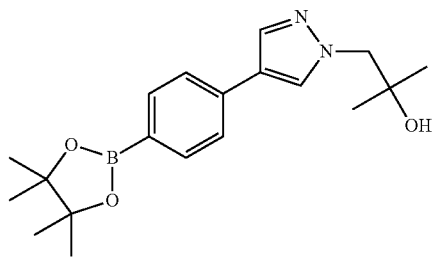 [SMILES: CC(C)(O)Cn1cc(-c2ccc(B3OC(C)(C)C(C)(C)O3)cc2)cn1]

In a screw-capped vessel 1-[4-(4-bromo-phenyl)-pyrazol-1-yl]-2-methyl-propan-2-ol (660 mg, 2.24 mmol), bis(pinacolato)diboron (1.12 g, 4.50 mmol), potassium acetate (660 mg, 6.74 mmol) and Pd(dppf)Cl₂.CH₂Cl₂ (168 mg, 0.224 mmol, 10 mol %) were weighed and suspended in acetonitrile (30 mL). The mixture was stirred overnight at 70° C. The reaction mixture was filtered and evaporated to dryness. The crude residue was purified by flash chromatography. Fractions containing product were evaporated to give 280 mg (25%) of the title compound as a colorless solid. Rt=2.298 min (HPLC method A).

18. Preparation of 1-(2-methanesulfonyl-ethyl)-4-[4-(4,4,5,5-tetramethyl-[1,3,2]dioxaborolan-2-yl)-phenyl]-1H-pyrazole

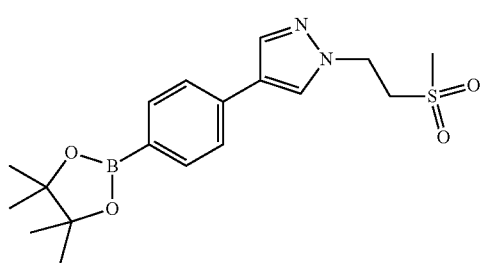 [SMILES: CC1(C)OB(c2ccc(-c3cnn(CCS(C)(=O)=O)c3)cc2)OC1(C)C]

In a 10 mL screw cap vessel 4-bromo-1-(2-methanesulfonyl-ethyl)-1H-pyrazole (200 mg, 0.751 mmol, 1,4-benzenediboronic acid bis(pinacol) ester, 97% (379 mg, 1.13 mmol), potassium carbonate (207 mg, 1.50 mmol) and Pd(dppf)Cl$_2$.CH$_2$Cl$_2$ (30.7 mg, 0.038 mmol) were suspended in acetonitrile (10 mL) and water (2 mL). The mixture was heated 1 h at 100° C. in the microwave oven. The solvents were evaporated, the residue was sonificated in acetonitrile and non-soluble parts were filtered off. The filtrate was evaporated and the crude product was purified by preparative chromatography (acetonitrile/water). Fractions were combined and evaporated to get 108 mg (38%) of a colorless solid.

19. Preparation of 2-(1,1-dioxo-2,3-dihydro-1H-1lambda6-benzo[b]thiophen-5-yl)-4,4,5,5-tetramethyl-[1,3,2]dioxaborolane

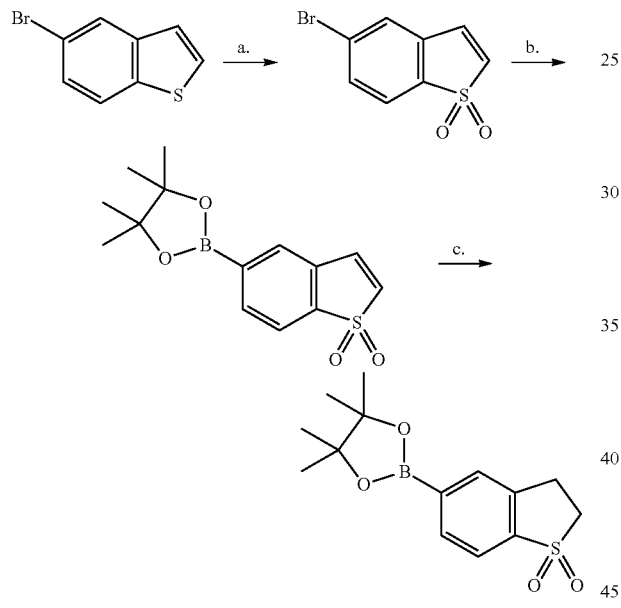

19a. 5-Bromo-benzo[b]thiophene 1,1-dioxide

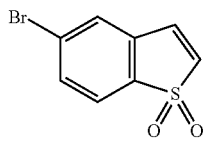

In a 100 mL screwcapped vessel 5-bromobenzo[b]thiophene (2.30 g, 10.8 mmol) was dissolved in acetone (46 ml). Oxone®, monopersulfate (potassium peroxymonosulfate) (27.0 g, 43.2 mmol) and water were added and stirred at 70° C. overnight. To the reaction mixture water and ethyl acetate were added. The organic layer was separated, dried, filtered and the solvent was evaporated to dryness. The yellow residue was purified by flash-chromatography (n-heptane/DCM) to give 769 mg (29%) of the title compound as a white solid. Rt=2.393 min (HPLC method A).

19b. 2-(1,1-Dioxo-1H-1lambda6-benzo[b]thiophen-5-yl)-4,4,5,5-tetramethyl-[1,3,2]dioxaborolane

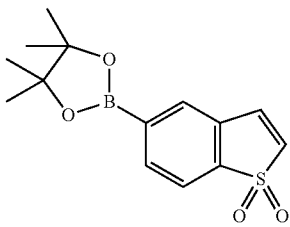 [SMILES: CC1(C)OB(c2ccc3c(c2)C=CS3(=O)=O)OC1(C)C]

In a 100 mL screwcapped vessel 5-bromo-benzo[b]thiophene 1,1-dioxide (767 mg, 3.13 mmol) was dissolved in tetrahydrofuran (50 mL). Bis(pinacolato)diboron (1.19 g, 4.69 mmol), potassium acetate (921 mg, 9.39 mmol) and Pd(dppf)Cl$_2$.CH$_2$Cl$_2$ (256 mg, 0.31 mmol) were added. The red reaction mixture was stirred overnight at 70° C. The crude residue was purified by flash-chromatography (n-heptane/DCM) to give 870 mg (95%) of the title compound as a colorless solid. Rt=1.599 min (HPLC method A).

19c. 2-(1,1-Dioxo-2,3-dihydro-1H-1lambda6-benzo[b]thiophen-5-yl)-4,4,5,5-tetramethyl-[1,3,2]dioxaborolane

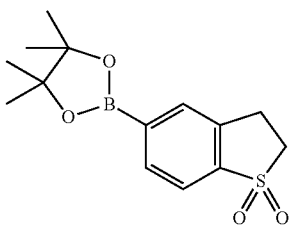 [SMILES: CC1(C)OB(c2ccc3c(c2)CCS3(=O)=O)OC1(C)C]

2-(1,1-Dioxo-1H-1lambda6-benzo[b]thiophen-5-yl)-4,4,5,5-tetramethyl-[1,3,2]dioxaborolane (463 mg, 1.59 mmol) was dissolved in tetrahydrofuran (10 mL), Pd/C (5% E101R, 54% water, 0.10 g) was added and the mixture stirred under hydrogen at RT for 2 h. The reaction mixture was filtered and the solvent removed under reduced pressure to give 454 mg (97%) of the title compound as a white solid. Rt=1.437 (HPLC method A).

Biological Activity

To assess the inhibitory potential of the compounds on the Wnt pathway, IC$_{50}$-values were determined, as shown in Table 1 below. Also shown is the human hepatic microsomal intrinsic clearance (CLint), whereby the following classification is used:

| | |
|---|---|
| CLint < 10 µL/min/mg | "A" |
| 10 µL/min/mg ≤ CLint < 50 µL/min/mg | "B" |
| 50 µL/min/mg ≤ CLint < 100 µL/min/mg | "C" |
| 100 µL/min/mg ≤ CLint < 150 µL/min/mg | "D" |
| 150 µL/min/mg ≤ CLint | "E" |

1. Cellular Assay for Wnt Pathway Activity
LS174T-shl-fLuc Clone 5 (LS174T-L5) Reporter Assay
Principle:

This assay is based on an in-vitro luciferase activity readout. The human colon cancer cell line, LS174T was transduced with a lentivirus encoding a short half-life luciferase (with a destabilised PEST sequence construct; construct F1756): 16×TCF/LEF transcription sites—short half life firefly luciferase on a basal pTA promoter—puromycin resistance gene on an EF-1-α promoter). This construct was made using the lentiviral base vector: pCDF1-MCS2-EF1-Puro from System Biosciences (cat. # CD110B-1). The luciferase has a $T_{1/2}$ of about 60 minutes.

Stable luciferase-expressing clones were selected, using 1 µg/mL puromycin selection and the clones were bulked up. Clone 5 was selected for routine use because it had a good signal to background ratio and was responsive to test reference compounds.

The luciferase readout is analysed as a reporter of TCF-regulated transcription and hence Wnt signalling activation. Compounds that inhibit the Wnt pathway are predicted to inhibit the induction of luciferase transcription by TCF; this will result in reduced luciferase protein production and luciferase signal readout.

Compounds were tested for their Wnt pathway inhibitory activities using the described firefly luciferase reporter cell based assay. An LS174T luciferase reporter cell line was used which contained a T-Cell Factor (TCF) dependent gene promoter firefly luciferase construct.

Compounds, in concentrations from 30 µM to 1 nM, were incubated for 24 hours on the cells. Luciferase activities were determined using the Steady Glo Luciferase Assay System (Promega) and the TOPCOUNT microplate reader (Perkin Elmer). For analysis, the obtained data were normalized against the untreated vehicle control and fitted for determination of the $IC_{50}$ values using the Excel Fit application of the Excel Software (Microsoft).

2. CLint (Intrinsic Clearance) Assay
Instrumentation

A Tecan Genesis workstation (RWS ASY 150/8) was used to perform the microsomal incubations. Analysis was carried out using a Waters ACQUITY UPLC system coupled to an ABSciex API3000 mass spectrometer. Data analysis was performed using Assay Explorer (Symyx).

UPLC Conditions
Column: Acquity UPLC BEH C18, 2.1×50 mm, 1.7 um (Waters)
Mobile phases:
A=0.1% formic acid in water
B=acetonitrile Gradient:

| Time | % A | % B |
|---|---|---|
| initial | 90 | 10 |
| 0.47 | 5 | 95 |
| 0.65 | 5 | 95 |
| 0.66 | 90 | 10 |

Flow rate: 0.750 mL/min
Detection: ESI, MRM
Injection: 10 uL
Column temperature: 50° C.
Chemicals
0.1 M potassium phosphate buffer pH 7.4 containing 1 mM $MgCl_2$
15 mM NADPH in phosphate buffer
5.0 mg protein/mL liver microsomes in phosphate buffer acetonitrile
20% DMSO in water
Microsomal Incubation Each experiment consists of 12 test and 2 reference compounds. The reference compounds are incubated as a cocktail.

Dilution of test compounds was done in 2 steps from a 10 mM DMSO stock solution. First 4 µL stock solution was added to 196 µL of 20% DMSO in potassium phosphate buffer pH 7.4. In a second step 10 µL of the first dilution were added to 1890 µL potassium phosphate buffer and 100 µL internal standard solution to a final concentration of 0.8 µM.

100 µL of the final compound dilution were aliquoted into a 96 deep well plate. 12.5 µL liver microsomes were added to each well (0.5 mg/mL final protein concentration) and the samples preincubated for 5 min at 37° C. and 800 rpm agitation.

After the preincubation, 250 µL cold acetonitrile were added to the 0 min samples to prevent a reaction. Following this, 12.5 µL NADPH solution were added to all wells to start the incubation, with the exception of the 0 min and 30 min controls without cofactor, where the NADPH was substituted for phosphate buffer.

The incubations were stopped after 5, 10, 20 and 30 min by adding 250 µL cold acetonitrile to the individual wells.

The quenched samples were then centrifuged at 4000 g for 1 h at 4° C. 100 µL of the supernatant were transferred into 96 well plates for analysis.

Data Analysis

The metabolic stability of each compound was determined by measurement of the change in LC-MS/MS peak area over time. Assay Explorer software was used to automatically calculate the slope k of the decline. The intrinsic clearance (CLint) of each compound was then calculated according to the formula:

$$CLint(\mu L/min/mg\ protein) = k1000/protein\ concentration.$$

TABLE 1

| No | Chemical Structure | LS174T IC$_{50}$ [μM] | Human CLint [μL/min/mg] | HPLC/MS Rt [min] (method) | Chemical Name | NMR data |
|---|---|---|---|---|---|---|
| E60 | 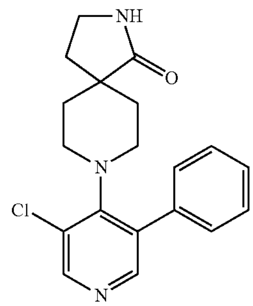 [SMILES: O=C1NCCC12CCN(c1c(Cl)cncc1-c1ccccc1)CC2] | 0.23 | E | | 8-(3-Chloro-5-phenyl-pyridin-4-yl)-2,8-diaza-spiro[4.5]decan-1-one | for analytical data see WO2010041054 |
| 1 | 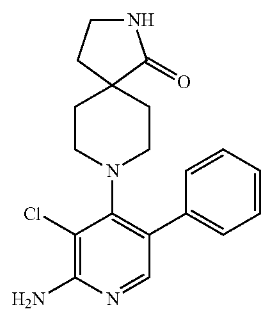 [SMILES: Nc1ncc(-c2ccccc2)c(N2CCC3(CCNC3=O)CC2)c1Cl] | 0.67 | B | 2.00 (A) | 8-(2-Amino-3-chloro-5-phenyl-pyridin-4-yl)-2,8-diaza-spiro[4.5]decan-1-one | 1H NMR (400 MHz, DMSO-d6) ppm = 8.45 (s, 1H), 7.68 (s, 1H), 7.58-7.37 (m, 5H), 7.37-7.27 (m, 2H), 3.22-3.03 (m, 4H), 2.79-2.68 (m, 2H), 1.83 (t, J = 6.8, 2H), 1.71-1.55 (m, 2H), 1.30-1.20 (m, 2H). |
| 2 | 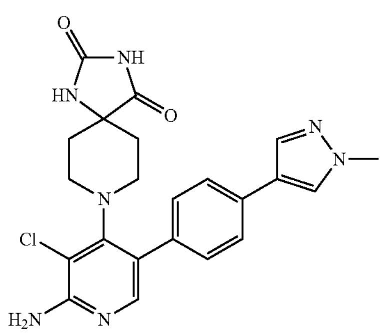 [SMILES: Cn1cc(-c2ccc(-c3cnc(N)c(Cl)c3N3CCC4(CC3)NC(=O)NC4=O)cc2)cn1] | 0.031 | A | 1.96 (A) | 8-{2-Amino-3-chloro-5-[4-(1-methyl-1H-pyrazol-4-yl)-phenyl]-pyridin-4-yl}-1,3,8-triaza-spiro[4.5]decane-2,4-dione | 1H NMR (500 MHz, DMSO-d6) ppm = 10.64-10.59 (m, 1H), 8.54 (s, 1H), 8.17 (s, 1H), 7.92-7.87 (m, 1H), 7.68 (s, 1H), 7.66-7.60 (m, 2H), 7.35-7.26 (m, 2H), 7.26-7.15 (m, 2H), 3.88 (s, 3H), 3.23-3.17 (m, 2H), 3.10-2.98 (m, 2H), 1.87-1.77 (m, 2H), 1.54-1.45 (m, 2H). |
| 3 | 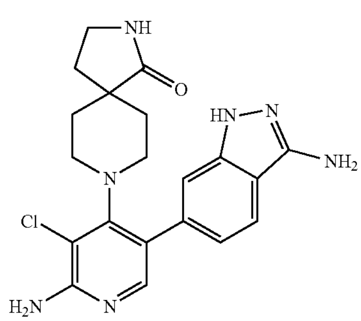 [SMILES: Nc1ncc(-c2ccc3c(N)n[nH]c3c2)c(N2CCC3(CCNC3=O)CC2)c1Cl] | 0.12 | A | 1.62 (A) | 8-[2-Amino-5-(3-amino-1H-indazol-6-yl)-3-chloro-pyridin-4-yl]-2,8-diaza-spiro[4.5]decan-1-one | 1H NMR (500 MHz, DMSO-d6) ppm = 11.80 (s, 1H), 7.79 (d, J = 8.2, 1H), 7.73 (s, 1H), 7.50 (s, 1H), 7.47-7.27 (m, 4H), 7.22 (s, 1H), 6.89-6.84 (m, 1H), 3.24-3.16 (m, 2H), 3.09 (t, J = 6.8, 2H), 2.50 (s, 2H), 1.80 (t, J = 6.8, 2H), 1.68 (td, J = 12.4, 4.1, 2H), 1.32-1.19 (m, 2H). |

TABLE 1-continued

| No | Chemical Structure | LS174T IC$_{50}$ [µM] | Human CLint [µL/min/mg] | HPLC/MS Rt [min] (method) | Chemical Name | NMR data |
|---|---|---|---|---|---|---|
| 4 | 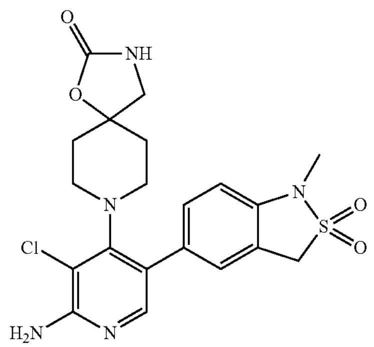 [SMILES: CN1c2ccc(-c3cnc(N)c(Cl)c3N3CCC4(CC3)CNC(=O)O4)cc2CS1(=O)=O] | 0.038 | A | 1.82 (A) | 8-[2-Amino-3-chloro-5-(1-methyl-2,2-dioxo-2,3-dihydro-1H-2l6-benzo[c]isothiazol-5-yl)-pyridin-4-yl]-1-oxa-3,8-diaza-spiro[4.5]decan-2-one | 1H NMR (500 MHz, DMSO-d6) ppm = 7.65 (s, 1H), 7.47 (s, 1H), 7.30 (s, 1H), 7.29-7.25 (m, 1H), 7.18-7.06 (m, 1H), 7.04 (d, J = 8.2, 1H), 7.02-6.72 (m, 1H), 4.69 (s, 2H), 3.19 (s, 2H), 3.09 (s, 3H), 3.03-2.92 (m, 4H), 1.80-1.60 (m, 4H). |
| 5 | 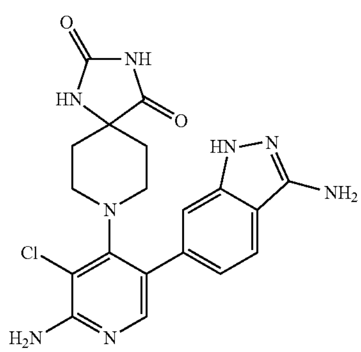 [SMILES: Nc1ncc(-c2ccc3c(N)n[nH]c3c2)c(N2CCC3(CC2)NC(=O)NC3=O)c1Cl] | 1.5 | A | 1.50 (A) | 8-[2-Amino-5-(3-amino-1H-indazol-6-yl)-3-chloro-pyridin-4-yl]-1,3,8-triaza-spiro[4.5]decane-2,4-dione | 1H NMR (500 MHz, DMSO-d6) ppm = 11.79 (s, 1H), 10.60 (s, 1H), 8.45 (s, 1H), 7.80 (d, J = 8.3, 1H), 7.71 (s, 1H), 7.36 (s, 4H), 7.23-7.21 (m, 1H), 6.88 (dd, J = 8.3, 1.4, 1H), 3.27-3.19 (m, 2H), 3.10-3.01 (m, 2H), 1.84-1.74 (m, 2H), 1.53-1.45 (m, 2H). |
| 6 | 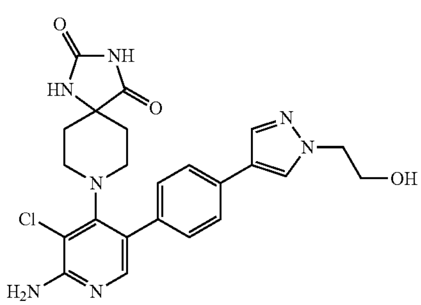 [SMILES: Nc1ncc(-c2ccc(-c3cnn(CCO)c3)cc2)c(N2CCC3(CC2)NC(=O)NC3=O)c1Cl] | 0.39 | B | 1.77 (A) | 8-(2-Amino-3-chloro-5-{4-[1-(2-hydroxy-ethyl)-1H-pyrazol-4-yl]-phenyl}-pyridin-4-yl)-1,3,8-triaza-spiro[4.5]decane-2,4-dione | 1H NMR (500 MHz, DMSO-d6) ppm = 10.61 (s, 1H), 8.53 (s, 1H), 8.18 (s, 1H), 7.92 (s, 1H), 7.69 (s, 1H), 7.66-7.63 (m, 2H), 7.32-7.26 (m, 2H), 7.22 (s, 2H), 4.87 (s, 1H), 4.18 (t, J = 5.6, 2H), 3.77 (t, J = 5.6, 2H), 3.24-3.16 (m, 2H), 3.08-2.99 (m, 2H), 1.87-1.77 (m, 2H), 1.54-1.46 (m, 2H). |
| 7 | 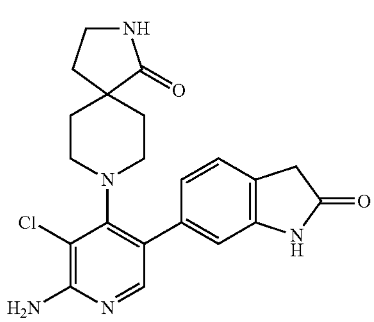 [SMILES: Nc1ncc(-c2ccc3c(c2)NC(=O)C3)c(N2CCC3(CCNC3=O)CC2)c1Cl] | 0.063 | B | 1.72 (B) | 6-(6-Amino-5-chloro-4-(1-oxo-2,8-diazaspiro[4.5]decan-8-yl)pyridin-3-yl)indolin-2-one | 1H-NMR (500 MHz, DMSO-d6) ppm = 10.39 (s, 1H), 7.61 (s, 1H), 7.52 (s, 1H), 7.23 (d, J = 7.6, 1H), 6.81 (dd, J = 7.5, 1.3, 1H), 6.68 (s, 1H), 6.11 (s, 2H), 3.51 (s, 2H), 3.12 (t, J = 6.8, 2H), 2.95 (d, J = 12.6, 2H), 2.65 (d, J = 9.8, 2H), 1.82 (t, J = 6.8, 2H), 1.71 (td, J = 12.6, 3.6, 2H), 1.23 (d, J = 12.6, 2H). |

TABLE 1-continued

| No | Chemical Structure | LS174T IC$_{50}$ [μM] | Human CLint [μL/min/mg] | HPLC/MS Rt [min] (method) | Chemical Name | NMR data |
|----|---|---|---|---|---|---|
| 8 | 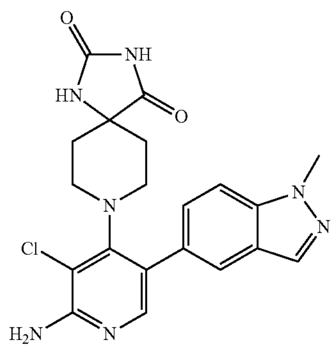 [SMILES: Cn1ncc2cc(-c3cnc(N)c(Cl)c3N3CCC4(CC3)NC(=O)NC4=O)ccc21] | 0.029 | A | 1.80 (A) | 8-[2-Amino-3-chloro-5-(1-methyl-1H-indazol-5-yl)-pyridin-4-yl]-1,3,8-triaza-spiro[4.5]decane-2,4-dione | 1H NMR (500 MHz, DMSO-d6) ppm = 10.58 (s, 1H), 8.45 (s, 1H), 8.08 (s, 1H), 7.72-7.66 (m, 3H), 7.35-7.29 (m, 1H), 7.29-7.11 (m, 2H), 4.09 (s, 3H), 3.23-3.14 (m, 2H), 3.05-2.94 (m, 2H), 1.82-1.69 (m, 2H), 1.51-1.40 (m, 2H). |
| 9 | 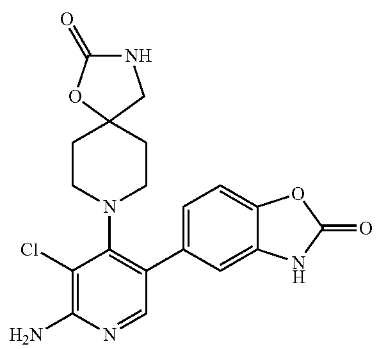 [SMILES: Nc1ncc(-c2ccc3oc(=O)[nH]c3c2)c(N2CCC3(CC2)CNC(=O)O3)c1Cl] | 0.098 | B | 1.75 (A) | 8-[2-Amino-3-chloro-5-(2-oxo-2,3-dihydro-benzooxazol-5-yl)-pyridin-4-yl]-1-oxa-3,8-diaza-spiro[4.5]decan-2-one | 1H NMR (500 MHz, DMSO-d6) ppm = 11.75 (s, 1H), 7.69 (s, 1H), 7.46 (s, 1H), 7.37 (d, J = 8.2, 1H), 7.35-7.07 (m, 2H), 7.06-6.97 (m, 2H), 3.18 (s, 2H), 3.05-2.88 (m, 4H), 1.78-1.61 (m, 4H). |
| 10 | 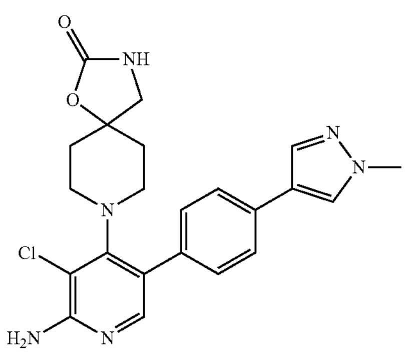 [SMILES: Cn1cc(-c2ccc(-c3cnc(N)c(Cl)c3N3CCC4(CC3)CNC(=O)O4)cc2)cn1] | 0.036 | B | 1.92 (A) | 8-{2-Amino-3-chloro-5-[4-(1-methyl-1H-pyrazol-4-yl)-phenyl]-pyridin-4-yl}-1-oxa-3,8-diaza-spiro[4.5]decan-2-one | 1H NMR (500 MHz, DMSO-d6) ppm = 8.20 (s, 1H), 7.92 (s, 1H), 7.72 (s, 1H), 7.67 (d, J = 8.2, 2H), 7.47 (s, 3H), 7.30 (d, J = 8.3, 2H), 3.87 (s, 3H), 3.19 (s, 2H), 3.09-2.94 (m, 4H), 1.79-1.65 (m, 4H). |
| 11 | 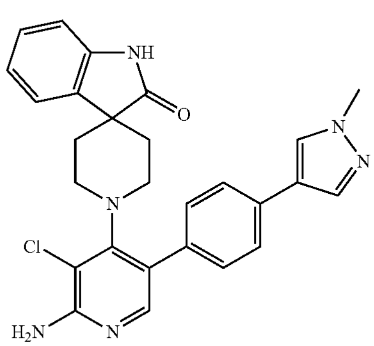 [SMILES: Cn1cc(-c2ccc(-c3cnc(N)c(Cl)c3N3CCC4(CC3)C(=O)Nc3ccccc34)cc2)cn1] | 0.003 | B | 2.38 (B) | 1'-(2-Amino-3-chloro-5-(4-(1-methyl-1H-pyrazol-4-yl)phenyl)pyridin-4-yl)spiro[indoline-3,4'-piperidin]-2-one | $^1$H-NMR (500 MHz, DMSO-d6) ppm = 10.35 (s, 1H), 8.20 (s, 1H), 7.93 (s, 1H), 7.70 (s, 1H), 7.69 (d, J = 6.1, 2H), 7.35 (d, J = 8.0, 2H), 7.30 (d, J = 7.4, 1H), 7.17 (dd, J = 7.7, 0.9, 1H), 6.97 (dd, J = 7.6, 0.9, 1H), 6.83 (d, J = 7.6, 1H), 6.16 (s, 2H), 3.88 (s, 3H), 3.26-3.15 (m, 2H), 3.07-2.98 (m, 2H), 1.89-1.71 (m, 2H), 1.56-1.34 (m, 2H). |

TABLE 1-continued

| No | Chemical Structure | LS174T IC$_{50}$ [μM] | Human CLint [μL/min/mg] | HPLC/MS Rt [min] (method) | Chemical Name | NMR data |
|---|---|---|---|---|---|---|
| 12 | 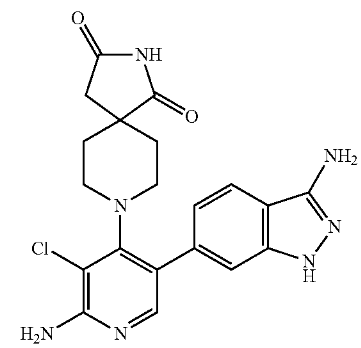 [SMILES: Nc1ncc(-c2ccc3c(N)n[nH]c3c2)c(N2CCC3(CC2)CC(=O)NC3=O)c1Cl] | 0.031 | B | 1.78 (A) | 8-[2-Amino-5-(3-amino-1H-indazol-6-yl)-3-chloro-pyridin-4-yl]-2,8-diaza-spiro[4.5]decane-1,3-dione | nd |
| 13 | 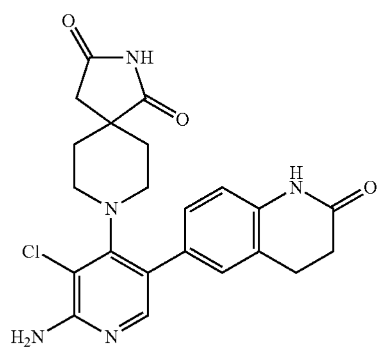 [SMILES: Nc1ncc(-c2ccc3c(c2)CCC(=O)N3)c(N2CCC3(CC2)CC(=O)NC3=O)c1Cl] | 0.014 | A | 1.80 (A) | 8-[2-Amino-3-chloro-5-(2-oxo-1,2,3,4-tetrahydro-quinolin-6-yl)-pyridin-4-yl]-2,8-diaza-spiro[4.5]decane-1,3-dione | 1H NMR (500 MHz, DMSO-d6) ppm = 11.08 (s, 1H), 10.16 (s, 1H), 7.64 (s, 1H), 7.39-6.98 (m, 4H), 6.93 (d, J = 8.1, 1H), 3.12 (d, J = 13.0, 2H), 2.98-2.90 (m, 2H), 2.87-2.74 (m, 2H), 2.56-2.50 (m, 4H), 1.79-1.65 (m, 2H), 1.46 (d, J = 12.9, 2H). |
| 14 | 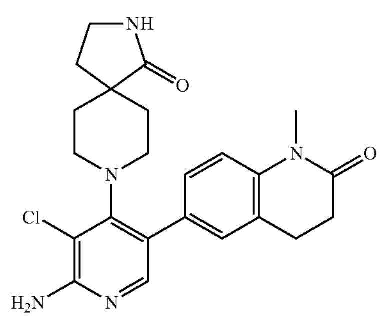 | 0.04 | B | 1.91 (A) | 6-[6-Amino-5-chloro-4-(1-oxo-2,8-diaza-spiro[4.5]dec-8-yl)-pyridin-3-yl]-1-methyl-3,4-dihydro-1H-quinolin-2-one | 1H NMR (500 MHz, DMSO-d6) ppm = 7.60 (s, 1H), 7.44 (s, 1H), 7.38-7.05 (m, 5H), 3.21 (s, 3H), 3.11-3.00 (m, 4H), 2.89-2.82 (m, 2H), 2.80-2.70 (m, 2H), 2.56-2.47 (m, 2H), 1.83-1.75 (m, 2H), 1.62-1.50 (m, 2H), 1.17 (d, J = 13.3, 2H). |
| 15 | 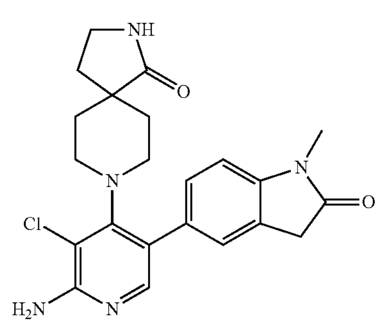 [SMILES: CN1C(=O)Cc2cc(-c3cnc(N)c(Cl)c3N3CCC4(CCNC4=O)CC3)ccc21] | 0.054 | B | 1.89 (A) | 8-[2-Amino-3-chloro-5-(1-methyl-2-oxo-2,3-dihydro-1H-indol-5-yl)-pyridin-4-yl]-2,8-diaza-spiro[4.5]decan-1-one | 1H NMR (500 MHz, DMSO-d6) ppm = 7.64 (s, 1H), 7.52 (s, 1H), 7.37-7.18 (m, 4H), 7.06 (d, J = 7.9, 1H), 3.63 (s, 2H), 3.20-3.08 (m, 7H), 2.85-2.76 (m, 2H), 1.90-1.83 (m, 2H), 1.69-1.59 (m, 2H), 1.24 (d, J = 13.4, 2H). |

TABLE 1-continued

| No | Chemical Structure | LS174T IC$_{50}$ [μM] | Human CLint [μL/min/mg] | HPLC/MS Rt [min] (method) | Chemical Name | NMR data |
|---|---|---|---|---|---|---|
| 16 | 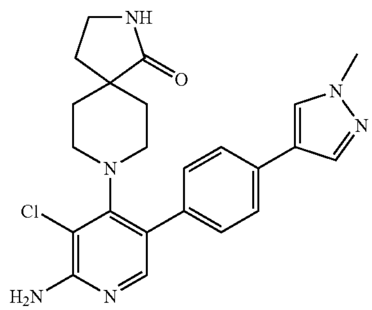 [SMILES: Cn1cc(-c2ccc(-c3cnc(N)c(Cl)c3N3CCC4(CCNC4=O)CC3)cc2)cn1] | 0.025 | D | 1.98 (B) | 8-{2-Amino-3-chloro-5-[4-(1-methyl-1H-pyrazol-4-yl)-phenyl]-pyridin-4-yl}-2,8-diaza-spiro[4.5]decan-1-one | $^1$H-NMR (500 MHz, DMSO-d6) ppm = 8.17 (s, 1H), 7.89 (d, J = 0.6, 1H), 7.64 (s, 1H), 7.60 (d, J = 8.3, 2H), 7.50 (s, 1H), 7.23 (d, J = 8.2, 2H), 6.11 (s, 2H), 3.87 (s, 3H), 3.10 (t, J = 6.8, 2H), 3.01-2.91 (m, 2H), 2.73-2.60 (m 2H), 1.76-1.63 (m, 2H), 1.81 (t, J = 6.8, 2H). |
| 17 | 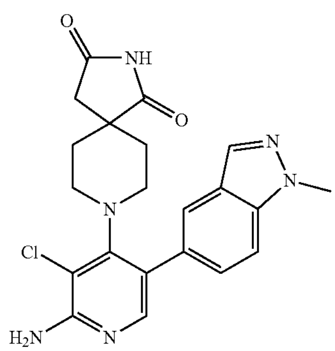 [SMILES: Cn1ncc2cc(-c3cnc(N)c(Cl)c3N3CCC4(CC3)CC(=O)NC4=O)ccc21] | 0.002 | B | 1.82 (A) | 8-[2-Amino-3-chloro-5-(1-methyl-1H-indazol-5-yl)-pyridin-4-yl]-2,8-diaza-spiro[4.5]decane-1,3-dione | 1H NMR (500 MHz, DMSO-d6) ppm = 11.06 (s, 1H), 8.09 (d, J = 1.0, 1H), 7.75-7.67 (m, 3H), 7.34-7.28 (m, 1H), 7.27-6.95 (m, 2H), 4.09 (s, 3H), 3.19-3.09 (m, 2H), 2.74-2.64 (m, 2H), 2.43 (s, 2H), 1.80-1.67 (m, 2H), 1.44 (d, J = 12.9, 2H). |
| 18 | 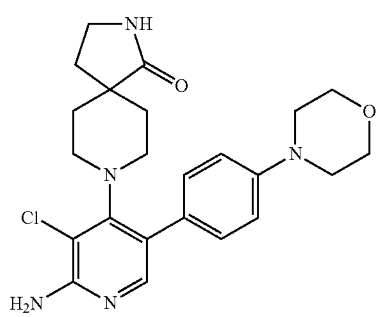 [SMILES: Nc1ncc(-c2ccc(N3CCOCC3)cc2)c(N2CCC3(CCNC3=O)CC2)c1Cl] | 0.12 | C | 1.87 (A) | 8-[2-Amino-3-chloro-5-(4-morpholin-4-yl-phenyl)-pyridin-4-yl]-2,8-diaza-spiro[4.5]decan-1-one | 1H NMR (500 MHz, DMSO-d6) ppm = 7.61 (s, 1H), 7.53 (s, 3H), 7.17 (d, J = 8.7, 2H), 7.02 (d, J = 8.8, 2H), 3.79-3.71 (m, 4H), 3.24-3.18 (m, 2H), 3.18-3.09 (m, 6H), 2.82-2.72 (m, 2H), 1.89-1.81 (m, 2H), 1.74-1.63 (m, 2H), 1.29 (d, J = 13.3, 2H). |
| 19 | 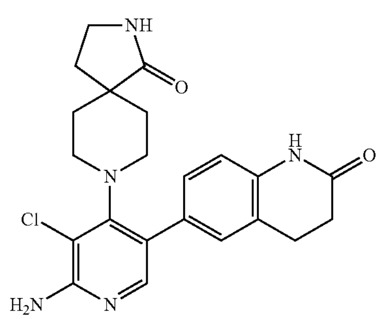 [SMILES: Nc1ncc(-c2ccc3c(c2)CCC(=O)N3)c(N2CCC3(CCNC3=O)CC2)c1Cl] | 0.075 | B | 1.81 (A) | 6-[6-Amino-5-chloro-4-(1-oxo-2,8-diaza-spiro[4.5]dec-8-yl)-pyridin-3-yl]-3,4-dihydro-1H-quinolin-2-one | 1H NMR (500 MHz, DMSO-d6) ppm = 10.16 (s, 1H), 7.64 (s, 1H), 7.51 (s, 1H), 7.35-7.20 (m, 2H), 7.13 (d, J = 1.9, 1H), 7.10-7.05 (m, 1H), 6.92 (d, J = 8.0, 1H), 3.19-3.09 (m, 4H), 2.97-2.90 (m, 2H), 2.86-2.76 (m, 2H), 2.47 (s, 2H), 1.86 (t, J = 6.8, 2H), 1.68-1.59 (m, 2H), 1.24 (d, J = 13.2, 2H). |

TABLE 1-continued

| No | Chemical Structure | LS174T IC$_{50}$ [μM] | Human CLint [μL/min/mg] | HPLC/MS Rt [min] (method) | Chemical Name | NMR data |
|---|---|---|---|---|---|---|
| 20 | 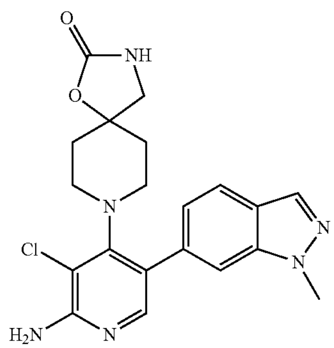 [SMILES: Cn1ncc2ccc(-c3cnc(N)c(Cl)c3N3CCC4(CC3)CNC(=O)O4)cc21] | 0.054 | B | 1.86 (A) | 8-[2-Amino-3-chloro-5-(1-methyl-1H-indazol-6-yl)-pyridin-4-yl]-1-oxa-3,8-diaza-spiro[4.5]decan-2-one | 1H NMR (500 MHz, DMSO-d6) ppm = 8.08 (s, 1H), 7.83 (d, J = 8.3, 1H), 7.78 (s, 1H), 7.61 (s, 1H), 7.43 (s, 1H), 7.15 (s, 2H), 7.05 (d, J = 8.3, 1H), 4.07 (s, 3H), 3.16 (s, 2H), 3.03-2.91 (m, 4H), 1.75-1.63 (m, 4H). |
| 21 | 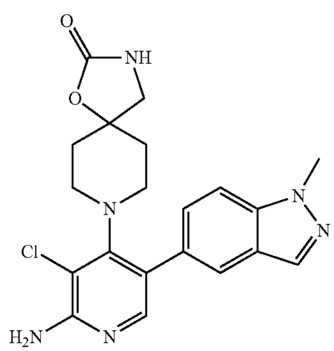 [SMILES: Cn1ncc2cc(-c3cnc(N)c(Cl)c3N3CCC4(CC3)CNC(=O)O4)ccc21] | 0.11 | B | 1.85 (A) | 8-[2-Amino-3-chloro-5-(1-methyl-1H-indazol-5-yl)-pyridin-4-yl]-1-oxa-3,8-diaza-spiro[4.5]decan-2-one | 1H NMR (500 MHz, DMSO-d6) ppm = 8.11 (d, J = 1.0, 1H), 7.77-7.71 (m, 3H), 7.49-7.28 (m, 4H), 4.09 (s, 3H), 3.15 (s, 2H), 3.07-2.99 (m, 2H), 2.97-2.87 (m, 2H), 1.73-1.63 (m, 4H). |
| 22 | 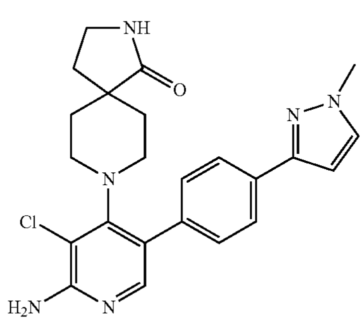 [SMILES: Cn1ccc(-c2ccc(-c3cnc(N)c(Cl)c3N3CCC4(CCNC4=O)CC3)cc2)n1] | 0.038 | B | 2.00 (B) | 8-{2-Amino-3-chloro-5-[4-(1-methyl-1H-pyrazol-3-yl)-phenyl]-pyridin-4-yl}-2,8-diaza-spiro[4.5]decan-1-one | 1H-NMR (500 MHz, DMSO-d6) ppm = 7.82 (d, J = 8.2, 2H), 7.74 (d, J = 2.2, 1H), 7.66 (s, 1H), 7.50 (s, 1H), 7.27 (d, J = 8.2, 2H), 6.72 (d, J = 2.2, 1H), 6.13 (s, 2H), 3.89 (s, 3H), 3.10 (t, J = 6.8, 2H), 2.96 (d, J = 12.4, 2H), 2.74-2.61 (m, 2H), 1.81 (t, J = 6.8, 2H), 1.75-1.63 (m, 2H), 1.25-1.12 (m, 2H). |
| 23 | 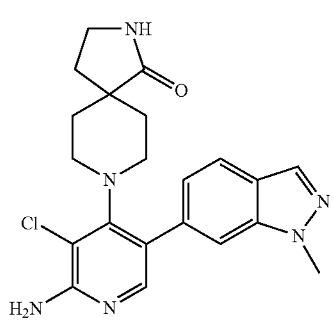 [SMILES: Cn1ncc2ccc(-c3cnc(N)c(Cl)c3N3CCC4(CCNC4=O)CC3)cc21] | 0.021 | B | 1.94 (A) | 8-[2-Amino-3-chloro-5-(1-methyl-1H-indazol-6-yl)-pyridin-4-yl]-2,8-diaza-spiro[4.5]decan-1-one | 1H NMR (500 MHz, DMSO-d6) ppm = 8.10-8.05 (m, 1H), 7.82 (d, J = 8.3, 1H), 7.77 (s, 1H), 7.63 (s, 1H), 7.49 (s, 3H), 7.06 (dd, J = 8.3, 1.4, 1H), 4.08 (s, 3H), 3.24-3.16 (m, 2H), 3.11-3.05 (m, 2H), 2.83-2.73 (m, 2H), 1.84-1.77 (m, 2H), 1.69-1.60 (m, 2H), 1.27-1.19 (m, 2H). |

TABLE 1-continued

| No | Chemical Structure | LS174T IC$_{50}$ [μM] | Human CLint [μL/min/mg] | HPLC/MS Rt [min] (method) | Chemical Name | NMR data |
|---|---|---|---|---|---|---|
| 24 | 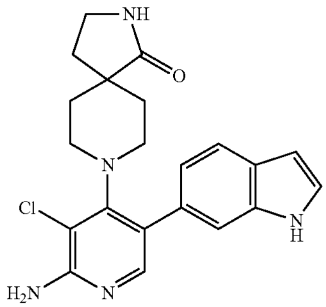 [SMILES: Nc1ncc(-c2ccc3cc[nH]c3c2)c(N2CCC3(CCNC3=O)CC2)c1Cl] | 0.018 | D | 2.11 (A) | 8-[2-Amino-3-chloro-5-(1H-indol-6-yl)-pyridin-4-yl]-2,8-diaza-spiro[4.5]decan-1-one | 1H NMR (500 MHz, DMSO-d6) ppm = 11.21 (s, 1H), 7.70 (s, 1H), 7.60 (d, J = 8.1, 1H), 7.49 (s, 1H), 7.45-7.31 (m, 4H), 6.95-6.86 (m, 1H), 6.47 (s, 1H), 3.19 (d, J = 13.1, 2H), 3.12-3.03 (m, 2H), 2.76-2.66 (m, 2H), 1.83-1.75 (m, 2H), 1.74-1.63 (m, 2H), 1.24 (d, J = 13.3, 2H). |
| 25 | 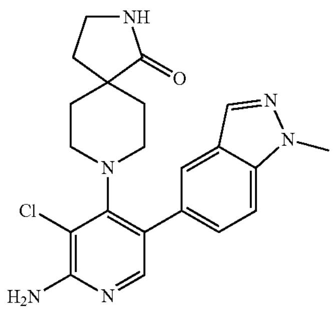 | 0.034 | C | 1.78 (B) | 8-[2-Amino-3-chloro-5-(1-methyl-1H-indazol-5-yl)-pyridin-4-yl]-2,8-diaza-spiro[4.5]decan-1-one | 1H NMR (500 MHz, DMSO-d6) ppm = 8.06 (s, 1H), 7.68-7.64 (m, 2H), 7.48 (s, 1H), 7.27 (dd, J = 8.7, 1.6, 1H), 6.09 (bs, 2H), 4.07 (s, 3H), 3.07 (t, J = 6.8, 2H), 3.01-2.92 (m, 2H), 2.70-2.55 (m, 2H), 1.75 (t, J = 6.8, 2H), 1.71-1.59 (m, 2H), 1.20-1.12 (m, 2H). |
| 26 | 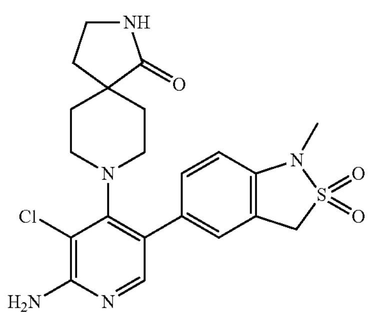 | 0.006 | D | 1.76 (B) | 8-(2-Amino-3-chloro-5-(1-methyl-2,2-dioxido-1,3-dihydro-benzo[c]isothiazol-5-yl)pyridin-4-yl)-2,8-diazaspiro[4.5]decan-1-one | $^1$H NMR (500 MHz, DMSO-d6) ppm = 7.62 (s, 1H), 7.53 (s, 1H), 7.28 (s, 1H), 7.23 (d, J = 8.2, 1H), 6.98 (d, J = 8.2, 1H), 6.14 (bs, 2H), 4.71 (s, 2H), 3.11 (t, J = 6.9, 2H), 3.07 (s, 3H), 2.98-2.91 (m, 2H), 2.77-2.65 (m, 2H), 1.84 (t, J = 6.9, 2H), 1.69-1.60 (m, 2H), 1.21-1.16 (m, 2H) |
| 27 | 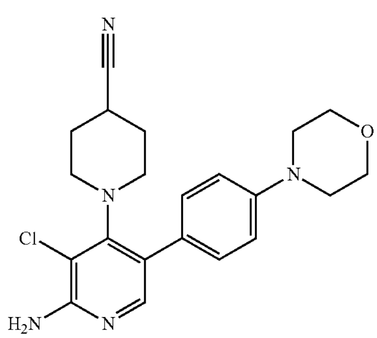 [SMILES: N#CC1CCN(c2c(-c3ccc(N4CCOCC4)cc3)cnc(N)c2Cl)CC1] | 0.034 | D | 2.04 (B) | 1-(2-Amino-3-chloro-5-(4-morpholino-phenyl)pyridin-4-yl)piperidine-4-carbonitrile | $^1$H-NMR (500 MHz, CDCl$_3$) ppm = 7.76 (s, 1H). 7.15-7.11 (m, 2H), 6.97-6.93 (m, 2H), 4.82 (s, 2H), 3.90-3.88 (m, 4H), 3.22-3.20 (m, 4H), 3.13-3.01 (m, 2H), 2.90-2.52 (m, 3H), 1.91-1.76 (m, 4H). |

TABLE 1-continued

| No | Chemical Structure | LS174T IC$_{50}$ [µM] | Human CLint [µL/ min/mg] | HPLC/ MS Rt [min] (method) | Chemical Name | NMR data |
|---|---|---|---|---|---|---|
| 28 | 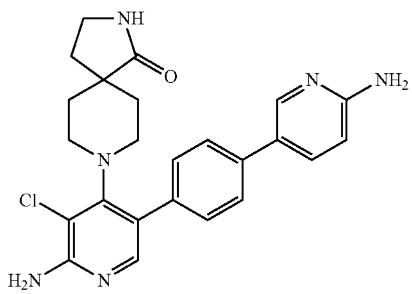 [SMILES: Nc1ccc(-c2ccc(-c3cnc(N)c(Cl)c3N3CCC4(CCNC4=O)CC3)cc2)cn1] | 0.012 | E | 1.76 (A) | 8-{2-Amino-5-[4-(6-amino-pyridin-3-yl)-phenyl]-3-chloro-pyridin-4-yl}-2,8-diaza-spiro[4.5]decan-1-one | 1H NMR (500 MHz, DMSO-d6) ppm = 8.39-8.30 (m, 2H), 8.20-7.82 (m, 2H), 7.76 (d, J = 8.3, 2H), 7.70 (s, 1H), 7.51 (s, 1H), 7.42 (d, J = 8.3, 2H), 7.27-7.09 (m, 2H), 7.07 (d, J = 9.0, 1H), 3.19-3.08 (m, 4H), 2.85-2.71 (m, 2H), 1.90-1.80 (m, 2H), 1.74-1.62 (m, 2H), 1.32-1.20 (m, 2H). |
| 29 | 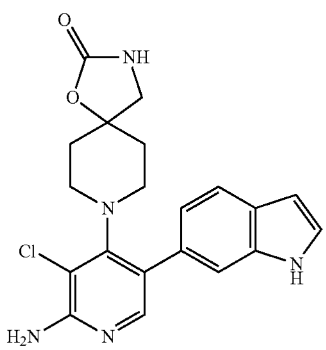 [SMILES: Nc1ncc(-c2ccc3cc[nH]c3c2)c(N2CCC3(CC2)CNC(=O)O3)c1Cl] | 0.03 | D | 2.00 (A) | 8-[2-Amino-3-chloro-5-(1H-indol-6-yl)-pyridin-4-yl]-1-oxa-3,8-diaza-spiro[4.5]decan-2-one | 1H NMR (500 MHz, DMSO-d6) ppm = 11.22 (s, 1H), 7.71 (s, 1H), 7.62 (d, J = 8.1, 1H), 7.49-7.07 (m, 5H), 6.91 (dd, J = 8.1, 1.5, 1H), 6.49-6.45 (m, 1H), 3.15 (s, 2H), 3.06-2.89 (m, 4H), 1.70 (t, J = 4.5, 4H). |
| 30 | 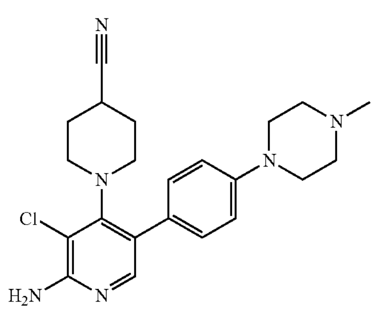 [SMILES: CN1CCN(c2ccc(-c3cnc(N)c(Cl)c3N3CCC(C#N)CC3)cc2)CC1] | 0.012 | B | 1.38 (B) | 1-(2-Amino-3-chloro-5-(4-(4-methyl-piperazin-1-yl)phenyl)pyridin-4-yl)piperidine-4-carbonitrile | $^1$H-NMR (500 MHz, CDCl$_3$) ppm = 7.75 (s, 1H), 7.11 (d, J = 8.7, 2H), 6.96 (d, J = 8.7, 2H), 4.81 (s, 2H), 3.27-3.25 (m, 4H), 3.12-3.03 (m, 2H), 2.85-2.60 (m, 3H), 2.61-2.59 (m, 4H), 2.37 (s, 3H), 1.89-1.77 (m, 4H). |
| 31 | 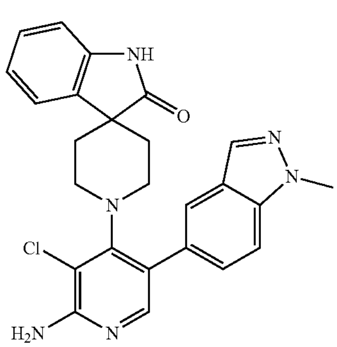 [SMILES: Cn1ncc2cc(-c3cnc(N)c(Cl)c3N3CCC4(CC3)C(=O)Nc3ccccc34)ccc21] | 0.004 | C | 2.33 (B) | 1'-(2-Amino-3-chloro-5-(1-methyl-1H-indazol-5-yl)pyridin-4-yl)spiro[indoline-3,4'-piperidin]-2-one | $^1$H-NMR (500 MHz, DMSO-d6) ppm = 10.34 (s, 1H), 8.15 (s, 1H), 7.83-7.67 (m, 3H), 7.41 (d, J = 8.2, 1H), 7.21 (d, J = 7.5, 1H), 7.15 (dd, J = 7.6, 7.6, 1H), 6.88 (dd, J = 7.6, 7.6, 1H), 6.8 (d, J = 7.5, 1H), 6.15 (s, 2H), 4.09 (s, 3H), 3.23-3.07 (m, 2H), 3.07-2.87 (m, 2H), 1.87-1.62 (m, 2H), 1.53-1.21 (m, 2H). |

TABLE 1-continued

| No | Chemical Structure | LS174T IC$_{50}$ [μM] | Human CLint [μL/min/mg] | HPLC/MS Rt [min] (method) | Chemical Name | NMR data |
|---|---|---|---|---|---|---|
| 32 | 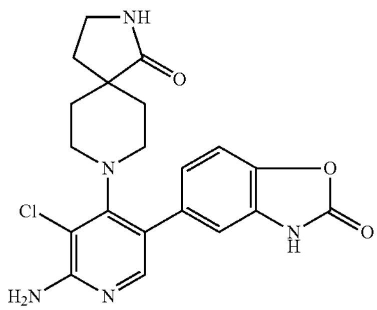 [SMILES: Nc1ncc(-c2ccc3oc(=O)[nH]c3c2)c(N2CCC3(CCNC3=O)CC2)c1Cl] | 0.017 | B | 1.84 (A) | 5-[6-Amino-5-chloro-4-(1-oxo-2,8-diaza-spiro[4.5]dec-8-yl)-pyridin-3-yl]-3H-benzooxazol-2-one | 1H NMR (500 MHz, DMSO-d6) ppm = 11.74 (s, 1H), 7.68 (s, 1H), 7.51 (s, 1H), 7.35 (d, J = 8.1, 1H), 7.30-7.05 (m, 2H), 7.04-6.96 (m, 2H), 3.18-3.07 (m, 4H), 2.76-2.66 (m, 2H), 1.83 (t, J = 6.8, 2H), 1.71-1.60 (m, 2H), 1.25 (d, J = 13.5, 2H). |
| 33 | 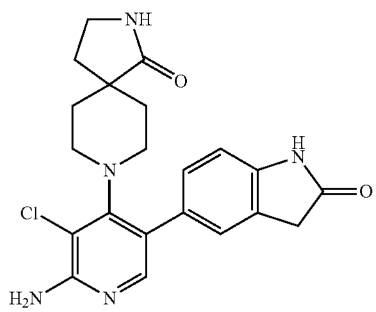 [SMILES: Nc1ncc(-c2ccc3c(c2)CC(=O)N3)c(N2CCC3(CCNC3=O)CC2)c1Cl] | 0.154 | B | 1.75 (A) | 8-[2-Amino-3-chloro-5-(2-oxo-2,3-dihydro-1H-indol-5-yl)-pyridin-4-yl]-2,8-diaza-spiro[4.5]decan-1-one | 1H NMR (500 MHz, DMSO-d6) ppm = 10.45 (s, 1H), 7.62 (s, 1H), 7.50 (s, 1H), 7.33-7.13 (m, 3H), 7.12-7.06 (m, 1H), 6.87 (d, J = 7.9, 1H), 3.56-3.52 (m, 2H), 3.15-3.08 (m, 4H), 2.85-2.74 (m, 2H), 1.89-1.82 (m, 2H), 1.69-1.57 (m, 2H), 1.22 (d, J = 13.2, 2H). |
| 34 | 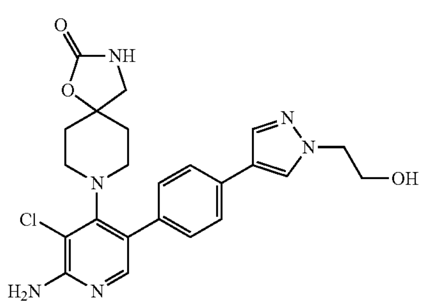 [SMILES: Nc1ncc(-c2ccc(-c3cnn(CCO)c3)cc2)c(N2CCC3(CC2)CNC(=O)O3)c1Cl] | 0.37 | B | 1.92 (A) | 8-(2-Amino-3-chloro-5-{4-[1-(2-hydroxy-ethyl)-1H-pyrazol-4-yl]-phenyl}-pyridin-4-yl)-1-oxa-3,8-diaza-spiro[4.5]decan-2-one | 1H NMR (500 MHz, DMSO-d6) ppm = 8.21 (s, 1H), 7.94 (s, 1H), 7.71 (s, 1H), 7.70-7.66 (m, 2H), 7.46 (s, 1H), 7.32-7.27 (m, 2H), 7.21 (s, 1H), 4.16 (t, J = 5.7, 2H), 3.77 (t, J = 5.7, 2H), 3.22-3.15 (m, 2H), 3.06-2.92 (m, 4H), 1.81-1.66 (m, 4H). |
| 35 | 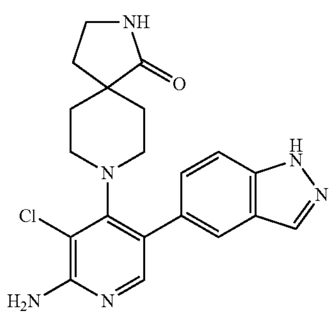 [SMILES: Nc1ncc(-c2ccc3[nH]ncc3c2)c(N2CCC3(CCNC3=O)CC2)c1Cl] | 0.085 | nd | 1.81 (A) | 8-[2-Amino-3-chloro-5-(1H-indazol-5-yl)-pyridin-4-yl]-2,8-diaza-spiro[4.5]decan-1-one | 1H NMR (500 MHz, DMSO-d6) ppm = 13.17 (s, 1H), 8.14 (d, J = 1.1, 1H), 7.76-7.69 (m, 2H), 7.62 (d, J = 8.1, 1H), 7.49 (s, 1H), 7.45-7.19 (m, 3H), 3.23-3.13 (m, 2H), 3.12-3.05 (m, 2H), 2.79-2.67 (m, 2H), 1.83-1.76 (m, 2H), 1.70-1.60 (m, 2H), 1.23 (d, J = 13.4, 2H). |

TABLE 1-continued

| No | Chemical Structure | LS174T IC$_{50}$ [μM] | Human CLint [μL/min/mg] | HPLC/MS Rt [min] (method) | Chemical Name | NMR data |
|---|---|---|---|---|---|---|
| 36 | 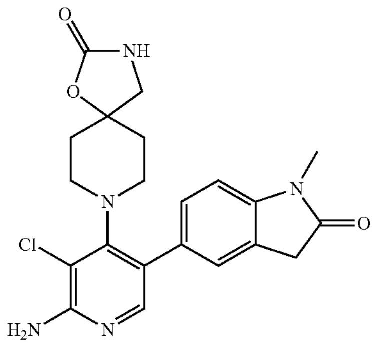 [SMILES: CN1C(=O)Cc2cc(-c3cnc(N)c(Cl)c3N3CCC4(CC3)CNC(=O)O4)ccc21] | >0.3 | nd | 1.79 (A) | 8-[2-Amino-3-chloro-5-(1-methyl-2-oxo-2,3-dihydro-1H-indol-5-yl)-pyridin-4-yl]-1-oxa-3,8-diaza-spiro[4.5]decan-2-one | 1H NMR (500 MHz, DMSO-d6) ppm = 7.64 (s, 1H), 7.46 (s, 1H), 7.35-7.24 (m, 2H), 7.24-7.22 (m, 1H), 7.21-7.16 (m, 1H), 7.08 (d, J = 8.0, 1H), 3.59 (s, 2H), 3.20 (s, 2H), 3.16 (s, 3H), 3.04-2.93 (m, 4H), 1.78-1.65 (m, 4H). |
| 37 | 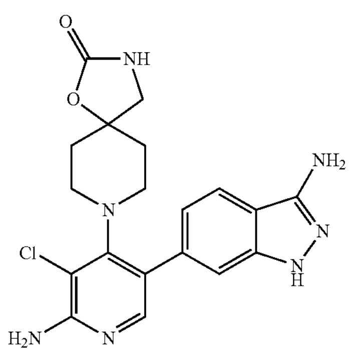 [SMILES: Nc1ncc(-c2ccc3c(N)n[nH]c3c2)c(N2CCC3(CC2)CNC(=O)O3)c1Cl] | 2.3 | nd | 1.66 (A) | 8-[2-Amino-5-(3-amino-1H-indazol-6-yl)-3-chloro-pyridin-4-yl]-1-oxa-3,8-diaza-spiro[4.5]decan-2-one | 1H NMR (500 MHz, DMSO-d6) ppm = 11.86 (s, 1H), 7.82 (d, J = 8.3, 1H), 7.75 (s, 1H), 7.67-7.43 (m, 2H), 7.41-7.27 (m, 2H), 7.26-7.06 (m, 2H), 6.91-6.84 (m, 1H), 3.19-3.15 (m, 2H), 3.07-2.86 (m, 4H), 1.82-1.60 (m, 4H). |
| 38 | 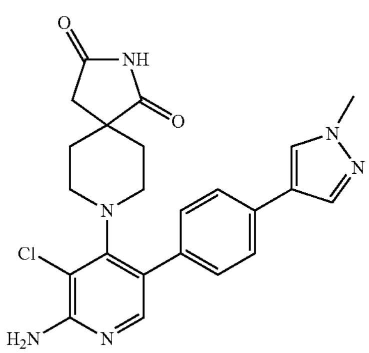 [SMILES: Cn1cc(-c2ccc(-c3cnc(N)c(Cl)c3N3CCC4(CC3)CC(=O)NC4=O)cc2)cn1] | 0.002 | nd | 1.93 (B) | 8-{2-Amino-3-chloro-5-[4-(1-methyl-1H-pyrazol-4-yl)-phenyl]-pyridin-4-yl}-2,8-diaza-spiro[4.5]decane-1,3-dione | $^1$H-NMR (500 MHz, DMSO-d6) ppm = 8.18 (s, 1H), 7.90 (d, J = 0.5, 1H), 7.65 (s, 1H), 7.61 (d, J = 8.2, 2H), 7.24 (d, J = 8.2, 2H), 6.13 (s, 2H), 3.87 (s, 3H), 2.98 (d, J = 12.8, 2H), 2.74-2.58 (m, 2H), 2.43 (s, 2H), 1.78 (t, J = 11.9, 2H), 1.44 (d, J = 11.9, 2H). |
| 39 | 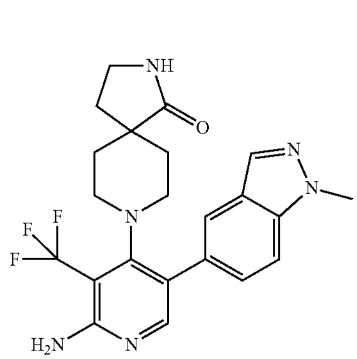 [SMILES: Cn1ncc2cc(-c3cnc(N)c(C(F)(F)F)c3N3CCC4(CCNC4=O)CC3)ccc21] | 0.035 | C | 1.94 (B) | 8-[2-Amino-5-(1-methyl-1H-indazol-5-yl)-3-trifluoromethyl-pyridin-4-yl]-2,8-diazaspiro[4.5]decan-1-one | $^1$H-NMR (500 MHz, CDCl$_3$) ppm = 8.03 (d, J = 1.0, 1H), 7.94 (s, 1H), 7.63 (dd, J = 1.6, 0.8, 1H), 7.49 (d, J = 8.6, 1H), 7.36 (d, J = 8.6, 1H), 5.33 (bs, 1H), 5.07 (bs, 2H), 4.14 (s, 3H), 3.21 (t, J = 6.8, 2H), 3.07 (dt, J = 12.3, 3.4, 2H), 2.85-2.71 (m, 2H), 1.87-1.71 (m, 4H), 1.16 (d, J = 13.1, 2H). |

TABLE 1-continued

| No | Chemical Structure | LS174T IC$_{50}$ [μM] | Human CLint [μL/ min/mg] | HPLC/ MS Rt [min] (method) | Chemical Name | NMR data |
|---|---|---|---|---|---|---|
| 40 | 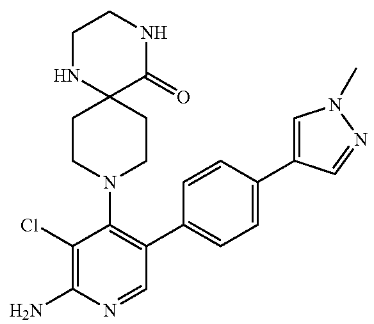 [SMILES: Cn1cc(-c2ccc(-c3cnc(N)c(Cl)c3N3CCC4(CC3)NCCNC4=O)cc2)cn1] | 0.1 | B | 1.37 (B) | 9-{2-Amino-3-chloro-5-[4-(1-methyl-1H-pyrazol-4-yl)-phenyl]-pyridin-4-yl}-1,4,9-triaza-spiro[5.5]undecan-5-one | $^1$H NMR (500 MHz, DMSO-d6) ppm = 8.17 (s, 1H), 7.89 (s, 1H), 7.60 (s, 1H), 7.59 (d, J = 8.3, 2H), 7.42 (s, 1H), 7.22 (d, J = 8.3, 2H), 6.06 (bs, 2H), 3.87 (s, 3H), 3.08-3.04 (m, 2H), 3.00-2.91 (m, 2H), 2.79-2.71 (m, 4H), 2.01-1.93 (m, 2H), 1.44-1.38 (m, 2H) |
| 41 | 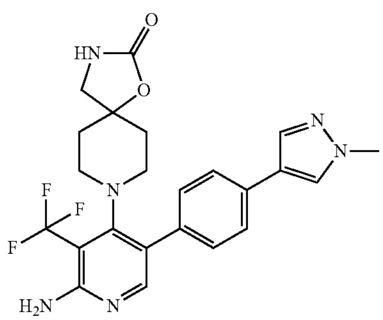 [SMILES: Cn1cc(-c2ccc(-c3cnc(N)c(C(F)(F)F)c3N3CCC4(CC3)CNC(=O)O4)cc2)cn1] | 0.075 | A | 1.95 (A) | 8-{2-Amino-5-[4-(1-methyl-1H-pyrazol-4-yl)-phenyl]-3-trifluoromethyl-pyridin-4-yl}-1-oxa-3,8-diaza-spiro[4.5]decan-2-one | 1H NMR (500 MHz, DMSO-d6) ppm = 8.18 (s, 1H), 7.92-7.89 (m, 1H), 7.77 (s, 1H), 7.68-7.62 (m, 2H), 7.42 (s, 1H), 7.37-7.31 (m, 2H), 7.23-6.95 (m, 2H), 3.87 (s, 3H), 3.12 (s, 2H), 3.10-3.01 (m, 2H), 3.01-2.93 (m, 2H), 1.62-1.54 (m, 2H), 1.53-1.46 (m, 2H). |
| 42 | 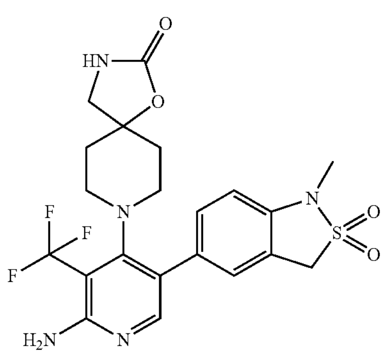 [SMILES: CN1c2ccc(-c3cnc(N)c(C(F)(F)F)c3N3CCC4(CC3)CNC(=O)O4)cc2CS1(=O)=O] | 0.011 | B | 1.85 (A) | 8-[2-Amino-5-(1-methyl-2,2-dioxo-2,3-dihydro-1H-2l6-benzo[c]isothiazol-5-yl)-3-trifluoromethyl-pyridin-4-yl]-1-oxa-3,8-diaza-spiro[4.5]decan-2-one | 1H NMR (400 MHz, DMSO-d6) ppm = 7.84 (s, 1H), 7.45 (s, 1H), 7.36-7.30 (m, 2H), 7.04 (d, J = 8.1, 1H), 6.37 (s, 2H), 4.70 (s, 2H), 3.14 (s, 2H), 3.11 (s, 3H), 3.04-2.93 (m, 2H), 2.87-2.77 (m, 2H), 1.65-1.55 (m, 2H), 1.53-1.41 (m, 2H). |
| 43 | 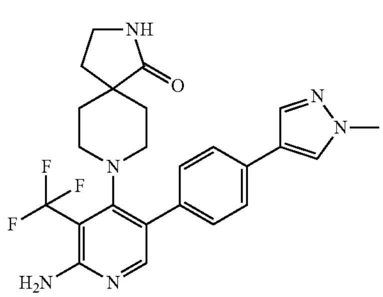 [SMILES: Cn1cc(-c2ccc(-c3cnc(N)c(C(F)(F)F)c3N3CCC4(CCNC4=O)CC3)cc2)cn1] | 0.046 | B | 2.07 (A) | 8-{2-Amino-5-[4-(1-methyl-1H-pyrazol-4-yl)-phenyl]-3-trifluoromethyl-pyridin-4-yl}-2,8-diaza-spiro[4.5]decan-1-one | 1H NMR (500 MHz, DMSO-d6) ppm = 8.17 (s, 1H), 7.91-7.88 (m, 1H), 7.74 (s, 1H), 7.66-7.61 (m, 2H), 7.45 (s, 1H), 7.36-7.32 (m, 2H), 7.26-7.02 (m, 2H), 3.87 (s, 3H), 3.18-3.11 (m, 2H), 3.07 (t, J = 6.8, 2H), 2.85 (t, J = 12.1, 2H), 1.77 (t, J = 6.8, 2H), 1.54 (td, J = 12.4, 4.2, 2H), 1.14-1.06 (m, 2H). |

TABLE 1-continued

| No | Chemical Structure | LS174T IC$_{50}$ [μM] | Human CLint [μL/min/mg] | HPLC/MS Rt [min] (method) | Chemical Name | NMR data |
|---|---|---|---|---|---|---|
| 44 | 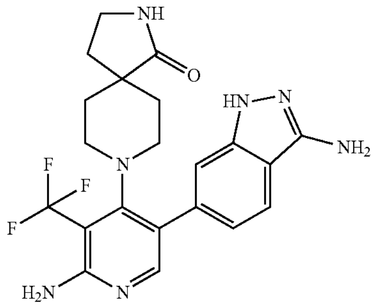 [SMILES: Nc1ncc(-c2ccc3c(N)n[nH]c3c2)c(N2CCC3(CCNC3=O)CC2)c1C(F)(F)F] | 0.27 | B | 1.73 (A) | 8-[2-Amino-5-(3-amino-1H-indazol-6-yl)-3-trifluoro-methyl-pyridin-4-yl]-2,8-diaza-spiro[4.5]decan-1-one | 1H NMR (500 MHz, DMSO-d6) ppm = 11.77 (s, 1H), 7.80-7.75 (m, 2H), 7.45 (s, 1H), 7.23 (s, 1H), 7.14-6.96 (m, 4H), 6.95-6.91 (m, 1H), 3.18-3.11 (m, 2H), 3.05 (t, J = 6.8, 2H), 2.86-2.77 (m, 2H), 1.72 (t, J = 6.8, 2H), 1.57-1.49 (m, 2H), 1.12-1.05 (m, 2H). |
| 45 | 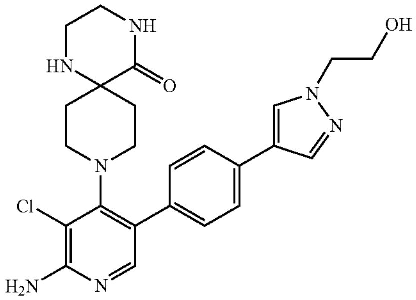 [SMILES: Nc1ncc(-c2ccc(-c3cnn(CCO)c3)cc2)c(N2CCC3(CC2)NCCNC3=O)c1Cl] | 0.56 | nd | 1.34 (B) | 9-(2-Amino-3-chloro-5-{4-[1-(2-hydroxy-ethyl)-1H-pyrazol-4-yl]-phenyl}-pyridin-4-yl)-1,4,9-triaza-spiro[5.5]undecan-5-one | $^1$H NMR (500 MHz, DMSO-d6) ppm = 8.19 (s, 1H), 7.93 (s, 1H), 7.61 (s, 1H), 7.60 (d, J = 8.2, 2H), 7.44 (bs, 1H), 7.23 (d, J = 8.2, 2H), 6.07 (bs, 2H), 4.94 (t, J = 5.6, 1H), 4.17 (t, J = 5.6, 2H), 3.77 (q, J = 5.6, 2H), 3.09-3.04 (m, 2H), 3.01-2.91 (m, 2H), 2.80-2.71 (m, 4H), 2.02-1.93 (m, 2H), 1.44-1.38 (m, 2H) |
| 46 | 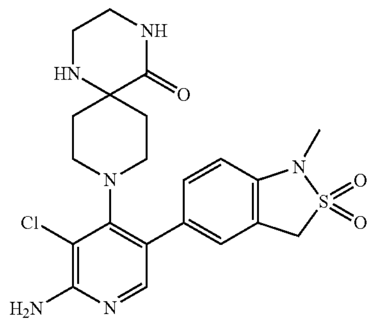 [SMILES: CN1c2ccc(-c3cnc(N)c(Cl)c3N3CCC4(CC3)NCCNC4=O)cc2CS1(=O)=O] | 0.15 | C | 1.02 (B) | 9-[2-Amino-3-chloro-5-(1-methyl-2,2-dioxo-2,3-dihydro-1H-2l6-benzo[c]isothiazol-5-yl)-pyridin-4-yl]-1,4,9-triaza-spiro[5.5]undecan-5-one | $^1$H NMR (500 MHz, DMSO-d6) ppm = 7.59 (s, 1H), 7.47 (s, 1H), 7.34 (s, 1H), 7.21 (d, J = 8.2, 1H), 6.97 (d, J = 8.2, 1H), 6.09 (bs, 2H), 4.73 (s, 2H), 3.09-3.05 (m, 4H), 3.06 (s, 3H), 2.78-2.71 (m, 4H), 1.93-1.82 (m, 2H), 1.41-1.33 (m, 2H) |
| 47 | 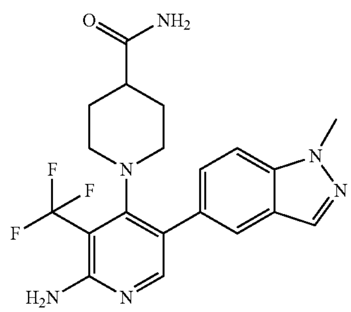 [SMILES: Cn1ncc2cc(-c3cnc(N)c(C(F)(F)F)c3N3CCC(C(N)=O)CC3)ccc21] | 0.11 | C | 1.84 (A) | 2'-Amino-5'-(1-methyl-1H-indazol-5-yl)-3'-trifluoromethyl-3,4,5,6-tetrahydro-2H-[1,4']bipyridinyl-4-carboxylic acid amide | 1H NMR (500 MHz, DMSO-d6) ppm = 8.08 (d, J = 0.9, 1H), 7.76 (s, 1H), 7.72-7.68 (m, 2H), 7.34 (dd, J = 8.7, 1.4, 1H), 7.05 (s, 3H), 6.63 (s, 1H), 4.08 (s, 3H), 3.17-3.11 (m, 2H), 2.71-2.62 (m, 2H), 2.01-1.92 (m, 1H), 1.41-1.26 (m, 4H). |
| 48 | 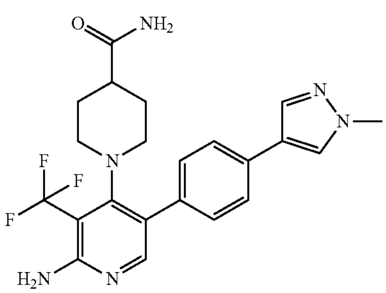 [SMILES: Cn1cc(-c2ccc(-c3cnc(N)c(C(F)(F)F)c3N3CCC(C(N)=O)CC3)cc2)cn1] | 0.16 | nd | 1.93 (A) | 2'-Amino-5'-[4-(1-methyl-1H-pyrazol-4-yl)-phenyl]-3'-trifluoro-methyl-3,4,5,6-tetrahydro-2H-[1,4']bipyridinyl-4-carboxylic acid amide | 1H NMR (500 MHz, DMSO-d6) ppm = 8.18 (s, 1H), 7.91 (d, J = 0.8, 1H), 7.75 (s, 1H), 7.65-7.61 (m, 2H), 7.32-7.28 (m, 2H), 7.09 (s, 1H), 6.95 (s, 2H), 6.65 (s, 1H), 3.87 (s, 3H), 3.15-3.07 (m, 2H), 2.75-2.66 (m, 2H), 2.07-1.97 (m, 1H), 1.47-1.33 (m, 4H). |

TABLE 1-continued

| No | Chemical Structure | LS174T IC$_{50}$ [μM] | Human CLint [μL/min/mg] | HPLC/MS Rt [min] (method) | Chemical Name | NMR data |
|---|---|---|---|---|---|---|
| 49 | 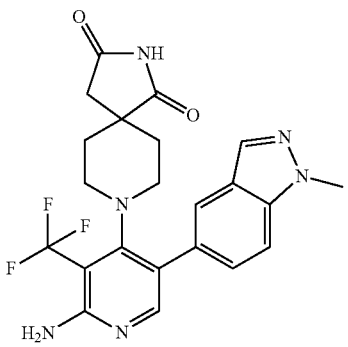 [SMILES: Cn1ncc2cc(-c3cnc(N)c(C(F)(F)F)c3N3CCC4(CC3)CC(=O)NC4=O)ccc21] | 0.004 | B | 1.88 (A) | 8-[2-Amino-5-(1-methyl-1H-indazol-5-yl)-3-trifluoromethyl-pyridin-4-yl]-2,8-diaza-spiro[4.5]decane-1,3-dione | nd |
| 50 | 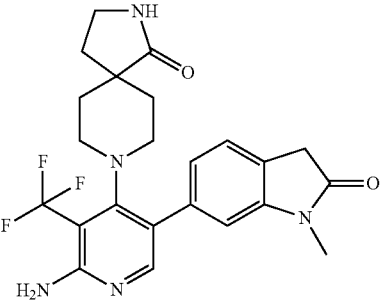 [SMILES: CN1C(=O)Cc2ccc(-c3cnc(N)c(C(F)(F)F)c3N3CCC4(CCNC4=O)CC3)cc21] | 0.817 | B | 1.927 (A) | 8-[2-Amino-5-(1-methyl-2-oxo-2,3-dihydro-1H-indol-6-yl)-3-trifluoromethyl-pyridin-4-yl]-2,8-diaza-spiro[4.5]decan-1-one | 1H NMR (500 MHz, DMSO-d6) ppm = 7.72 (s, 1H), 7.47 (s, 1H), 7.43-7.12 (m, 3H), 7.03 (d, J = 1.5, 1H), 6.99 (dd, J = 7.5, 1.5, 1H), 3.59 (s, 2H), 3.23-3.15 (m, 5H), 3.09 (t, J = 6.8, 2H), 2.92 (t, J = 12.0, 2H), 1.83 (t, J = 6.8, 2H), 1.59-1.49 (m, 2H), 1.11 (d, J = 13.0, 2H). |
| 51 | 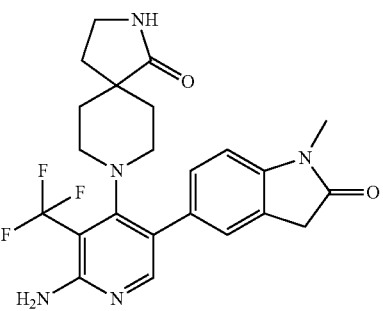 [SMILES: CN1C(=O)Cc2cc(-c3cnc(N)c(C(F)(F)F)c3N3CCC4(CCNC4=O)CC3)ccc21] | 0.455 | B | 1.947 (A) | 8-[2-Amino-5-(1-methyl-2-oxo-2,3-dihydro-1H-indol-5-yl)-3-trifluoromethyl-pyridin-4-yl]-2,8-diaza-spiro[4.5]decan-1-one | 1H NMR (500 MHz, DMSO-d6) ppm = 7.71 (s, 1H), 7.48 (s, 1H), 7.43-7.15 (m, 4H), 7.06 (d, J = 8.0, 1H), 3.66 (s, 2H), 3.18-3.11 (m, 5H), 3.08 (t, J = 6.8, 2H), 2.94-2.85 (m, 2H), 1.83 (t, J = 6.8, 2H), 1.51-1.38 (m, 2H), 1.06 (d, J = 13.0, 2H). |
| 52 | 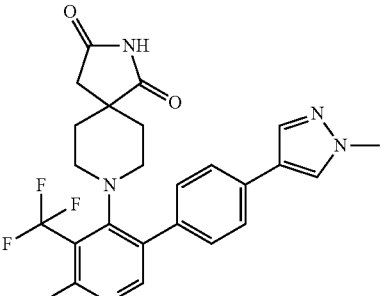 | 0.0012 | B | 1.973 (A) | 8-{2-Amino-5-[4-(1-methyl-1H-pyrazol-4-yl)-phenyl]-3-trifluoromethyl-pyridin-4-yl}-2,8-diaza-spiro[4.5]decane-1,3-dione | 1H NMR (500 MHz, DMSO-d6) ppm = 11.04 (s, 1H), 8.18 (s, 1H), 7.90 (s, 1H), 7.77 (s, 1H), 7.65 (d, J = 8.2, 2H), 7.34 (d, J = 8.1, 2H), 7.10 (s, 2H), 3.88 (s, 3H), 3.20-3.04 (m, 2H), 2.81 (t, J = 12.1, 2H), 2.42 (s, 2H), 1.66-1.56 (m, 2H), 1.36-1.28 (m, 2H). |

TABLE 1-continued

| No | Chemical Structure | LS174T IC$_{50}$ [µM] | Human CLint [µL/ min/mg] | HPLC/ MS Rt [min] (method) | Chemical Name | NMR data |
|---|---|---|---|---|---|---|
| 53 | 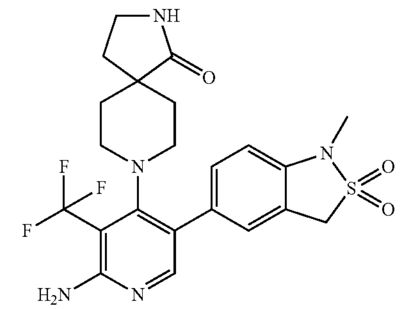 [SMILES: CN1c2ccc(-c3cnc(N)c(C(F)(F)F)c3N3CCC4(CCNC4=O)CC3)cc2CS1(=O)=O] | 0.00829 | C | 1.982 (A) | 8-[2-Amino-5-(1-methyl-2,2-dioxo-2,3-dihydro-1H-2l6-benzo[c]isothiazol-5-yl)-3-trifluoro-methyl-pyridin-4-yl]-2,8-diaza-spiro[4.5]decan-1-one | 1H NMR (500 MHz, DMSO-d6) ppm = 7.75 (s, 1H), 7.53 (s, 1H), 7.40-7.37 (m, 1H), 7.34 (dd, J = 8.1, 1.8, 1H), 7.32-7.17 (m, 2H), 7.03 (d, J = 8.1, 1H), 4.75 (s, 2H), 3.14-3.08 (m, 4H), 3.07 (s, 3H), 2.88 (t, J = 12.0, 2H), 1.83 (t, J = 6.8, 2H), 1.48-1.36 (m, 2H), 1.12-1.00 (m, 2H). |
| 54 | 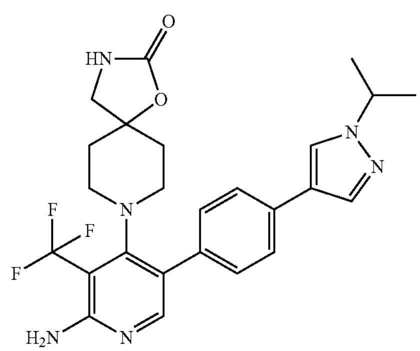 [SMILES: CC(C)n1cc(-c2ccc(-c3cnc(N)c(C(F)(F)F)c3N3CCC4(CC3)CNC(=O)O4)cc2)cn1] | 0.088 | B | 1.956 (A) | 8-{2-Amino-5-[4-(1-isopropyl-1H-pyrazol-4-yl)-phenyl]-3-trifluoro-methyl-pyridin-4-yl}-1-oxa-3,8-diaza-spiro[4.5]decan-2-one | 1H NMR (400 MHz, DMSO-d6) ppm = 8.31-8.23 (m, 1H), 7.95-7.87 (m, 1H), 7.83 (s, 1H), 7.65 (d, J = 8.2, 2H), 7.39 (s, 1H), 7.30 (d, J = 8.2, 2H), 6.32 (s, 2H), 4.52 (hept, J = 6.6, 1H), 3.11 (s, 2H), 3.02-2.88 (m, 2H), 2.88-2.75 (m, 2H), 1.67-1.51 (m, 4H), 1.47 (d, J = 6.7, 6H). |
| 55 | 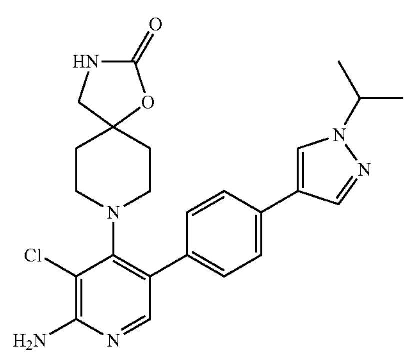 [SMILES: CC(C)n1cc(-c2ccc(-c3cnc(N)c(Cl)c3N3CCC4(CC3)CNC(=O)O4)cc2)cn1] | 0.17 | B | 1.921 (A) | 8-{2-Amino-3-chloro-5-[4-(1-isopropyl-1H-pyrazol-4-yl)-phenyl]-pyridin-4-yl}-1-oxa-3,8-diaza-spiro[4.5]decan-2-one | 1H NMR (400 MHz, DMSO-d6) ppm = 8.28 (s, 1H), 7.91 (s, 1H), 7.70-7.61 (m, 3H), 7.43 (s, 1H), 7.25 (d, J = 8.3, 2H), 6.11 (s, 2H), 4.52 (hept, J = 6.8, 1H), 3.19 (s, 2H), 3.04-2.76 (m, 4H), 1.79-1.65 (m, 4H), 1.47 (d, J = 6.7, 6H). |
| 56 | 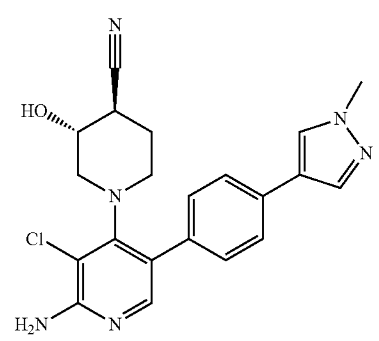 [SMILES: Cn1cc(-c2ccc(-c3cnc(N)c(Cl)c3N3CC[C@H](C#N)[C@@H](O)C3)cc2)cn1] | 0.531 | B | 1.435 (D) | rac (3R,4R)-2'-Amino-3'-chloro-3-hydroxy-5'-[4-(1-methyl-1H-pyrazol-4-yl)-phenyl]-3,4,5,6-tetrahydro-2H-[1,4']bipyridinyl-4-carbonitrile | 1H NMR (500 MHz, DMSO-d6) ppm = 8.16 (d, J = 0.8, 1H), 7.89 (d, J = 0.8, 1H), 7.66 (s, 1H), 7.60 (d, J = 8.2, 2H), 7.21 (d, J = 8.0, 2H), 6.18 (s, 2H), 5.55 (d, J = 5.8, 1H), 3.87 (s, 3H), 3.64-3.43 (m, 1H), 3.11-3.02 (m, 1H), 3.02-2.90 (m, 1H), 2.63-2.23 (m, 3H), 1.94-1.84 (m, 1H), 1.77-1.59 (m, 1H). |

TABLE 1-continued

| No | Chemical Structure | LS174T IC$_{50}$ [μM] | Human CLint [μL/min/mg] | HPLC/MS Rt [min] (method) | Chemical Name | NMR data |
|---|---|---|---|---|---|---|
| 57 | 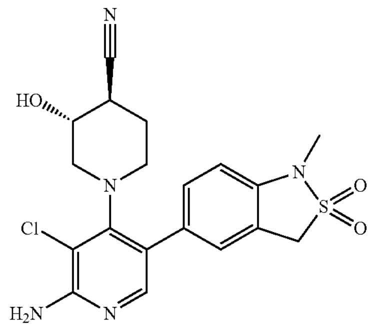 [SMILES: CN1c2ccc(-c3cnc(N)c(Cl)c3N3CC[C@H](C#N)[C@@H](O)C3)cc2CS1(=O)=O] | 0.0286 | B | 1.372 (D) | rac (3R,4R)-2'-Amino-3'-chloro-3-hydroxy-5'-(1-methyl-2,2-dioxo-2,3-dihydro-1H-2I6-benzo[c]isothiazol-5-yl)-3,4,5,6-tetrahydro-2H-[1,4']bipyridinyl-4-carbonitrile | 1H NMR (500 MHz, DMSO-d6) ppm = 7.63 (s, 1H), 7.24-7.15 (m, 2H), 6.98 (d, J = 8.1, 1H), 6.15 (s, 2H), 5.60 (d, J = 5.4, 1H), 4.68 (s, 2H), 3.68-3.38 (m, 1H), 3.14-3.01 (m, 4H), 2.96-2.83 (m, 1H), 2.65-2.22 (m, 3H), 1.98-1.81 (m, 1H), 1.76-1.58 (m, 1H). |
| 58 | 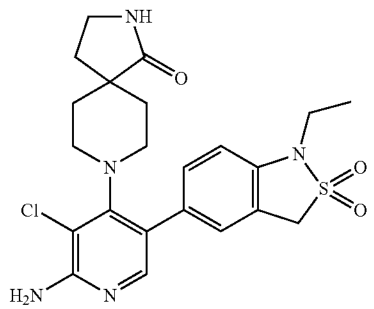 [SMILES: CCN1c2ccc(-c3cnc(N)c(Cl)c3N3CCC4(CCNC4=O)CC3)cc2CS1(=O)=O] | 0.0076 | E | 2.028 (A) | 8-[2-Amino-3-chloro-5-(1-ethyl-2,2-dioxo-2,3-dihydro-1H-2I6-benzo[c]isothiazol-5-yl)-pyridin-4-yl]-2,8-diaza-spiro[4.5]decan-1-one | 1H NMR (500 MHz, DMSO-d6) ppm = 7.63 (s, 1H), 7.49 (s, 1H), 7.27 (s, 1H), 7.25-7.20 (m, 1H), 7.01 (d, J = 8.2, 1H), 6.08 (s, 2H), 4.68 (s, 2H), 3.67 (q, J = 7.1, 2H), 3.12 (t, J = 6.8, 2H), 2.99-2.90 (m, 2H), 2.80-2.66 (m, 2H), 1.85 (t, J = 6.8, 2H), 1.71-1.58 (m, 2H), 1.29 (t, J = 7.1, 3H), 1.22-1.15 (m, 2H). |
| 59 | 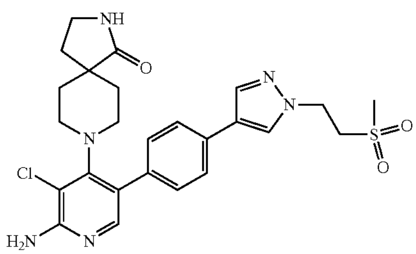 [SMILES: CS(=O)(=O)CCn1cc(-c2ccc(-c3cnc(N)c(Cl)c3N3CCC4(CCNC4=O)CC3)cc2)cn1] | 0.045 | B | 1.412 (D) | 8-(2-Amino-3-chloro-5-{4-[1-(2-methanesulfonyl-ethyl)-1H-pyrazol-4-yl]-phenyl}-pyridin-4-yl)-2,8-diaza-spiro[4.5]decan-1-one | 1H NMR (500 MHz, DMSO-d6) ppm = 8.30 (s, 1H), 7.99 (s, 1H), 7.64 (s, 1H), 7.61 (d, J = 8.2, 2H), 7.47 (s, 1H), 7.25 (d, J = 8.2, 2H), 6.08 (s, 2H), 4.58 (t, J = 6.9, 2H), 3.74 (t, J = 6.9, 2H), 3.10 (t, J = 6.8, 2H), 3.02-2.93 (m, 2H), 2.91 (s, 3H), 2.78-2.60 (m, 2H), 1.82 (t, J = 6.8, 2H), 1.77-1.61 (m, 2H), 1.29-1.12 (m, 2H). |
| 60 | 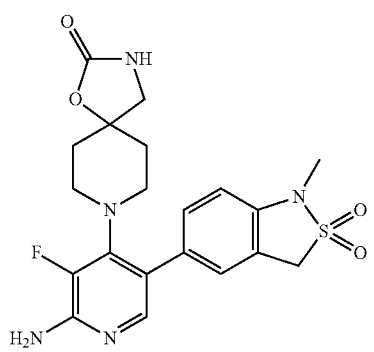 [SMILES: CN1c2ccc(-c3cnc(N)c(F)c3N3CCC4(CC3)CNC(=O)O4)cc2CS1(=O)=O] | 0.103 | A | 1.63 (B) | 8-[2-Amino-3-fluoro-5-(1-methyl-2,2-dioxo-2,3-dihydro-1H-2I6-benzo[c]isothiazol-5-yl)-pyridin-4-yl]-1-oxa-3,8-diaza-spiro[4.5]decan-2-one | 1H NMR (500 MHz, DMSO-d6) ppm = 7.484 (s, 1H), 7.477 (s, 1H), 7.44-7.41 (m, 2H), 6.98 (d, J = 8.8, 1H), 6.06 (s, 2H), 4.69 (s, 2H), 3.22 (s, 2H), 3.11-3.03 (m, 2H), 3.06 (s, 3H), 2.96-2.90 (m, 2H), 1.70-1.56 (m, 4H) |
| 61 | 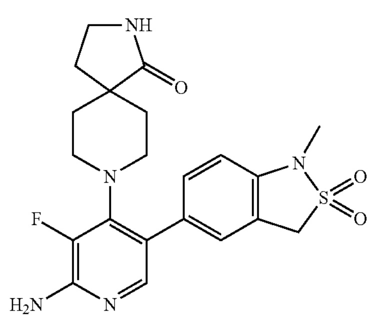 [SMILES: CN1c2ccc(-c3cnc(N)c(F)c3N3CCC4(CCNC4=O)CC3)cc2CS1(=O)=O] | 0.0601 | B | 1.73 (B) | 8-[2-Amino-3-fluoro-5-(1-methyl-2,2-dioxo-2,3-dihydro-1H-2I6-benzo[c]isothiazol-5-yl)-pyridin-4-yl]-2,8-diaza-spiro[4.5]decan-1-one | 1H NMR (500 MHz, DMSO-d6) ppm = 7.54 (s, 1H), 7.48 (s, 1H), 7.45 (s, 1H), 7.41 (d, J = 8.2, 1H), 6.97 (d, J = 8.2, 1H), 6.02 (s, 2H), 4.67 (s, 2H), 3.13 (t, J = 6.8, 2H), 3.07 (s, 3H), 3.07-3.01 (m, 2H), 2.92-2.86 (m, 2H), 1.91 (t, J = 6.8, 2H), 1.60-1.53 (m, 2H), 1.20-1.15 (m, 2H) |

TABLE 1-continued

| No | Chemical Structure | LS174T IC$_{50}$ [μM] | Human CLint [μL/ min/mg] | HPLC/ MS Rt [min] (method) | Chemical Name | NMR data |
|---|---|---|---|---|---|---|
| 62 | 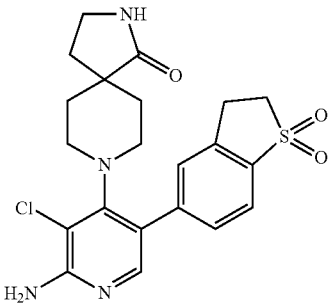 [SMILES: Nc1ncc(-c2ccc3c(c2)CCS3(=O)=O)c(N2CCC3(CCNC3=O)CC2)c1Cl] | 0.45 | B | 1.789 (A) | 8-[2-Amino-3-chloro-5-(1,1-dioxo-2,3-dihydro-1H-1I6-benzo[b]thiophen-5-yl)-pyridin-4-yl]-2,8-diaza-spiro[4.5]decan-1-one | 1H NMR (500 MHz, DMSO-d6) ppm = 7.80 (d, J = 8.0, 1H), 7.73 (s, 1H), 7.53 (s, 1H), 7.50 (s, 1H), 7.47-7.43 (m, 1H), 7.37-6.79 (m, 2H), 3.68-3.59 (m, 2H), 3.47-3.38 (m, 2H), 3.16-3.07 (m, 4H), 2.88-2.74 (m, 2H), 1.87 (t, J = 6.8, 2H), 1.71-1.58 (m, 2H), 1.29-1.21 (m, 2H). |
| 63 | 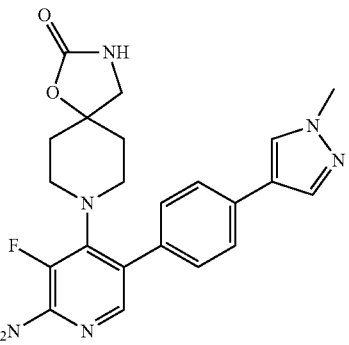 | 0.237 | B | 1.85 (B) | 8-{2-Amino-3-fluoro-5-[4-(1-methyl-1H-pyrazol-4-yl)-phenyl]-pyridin-4-yl}-1-oxa-3,8-diaza-spiro[4.5]decan-2-one | 1H NMR (500 MHz, DMSO-d6) ppm = 8.16 (s, 1H), 7.88 (d, J = 0.8, 1H), 7.59 (d, J = 8.4, 2H), 7.51 (s, 1H), 7.48 (s, 1H), 7.43 (d, J = 8.4, 2H), 6.04 (s, 2H), 3.87 (s, 3H), 3.21 (s, 2H), 3.11-3.05 (m, 2H), 2.98-2.92 (m, 2H), 1.71-1.58 (m, 4H) |
| 64 | 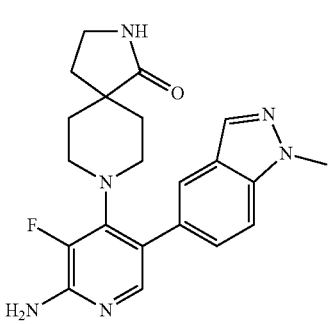 | 0.644 | B | 1.82 (B) | 8-[2-Amino-3-fluoro-5-(1-methyl-1H-indazol-5-yl)-pyridin-4-yl]-2,8-diaza-spiro[4.5]decan-1-one | 1H NMR (500 MHz, DMSO-d6) ppm = 8.03 (d, J = 0.9, 1H), 7.73-7.71 (m, 1H), 7.64 (d, J = 8.5, 1H), 7.51-7.48 (m, 3H), 5.98 (s, 2H), 4.06 (s, 3H), 3.11-3.03 (m, 4H), 2.90-2.83 (m, 2H), 1.87 (t, J = 6.8, 2H), 1.56-1.49 (m, 2H), 1.17-1.11 (m, 2H) |
| 65 | 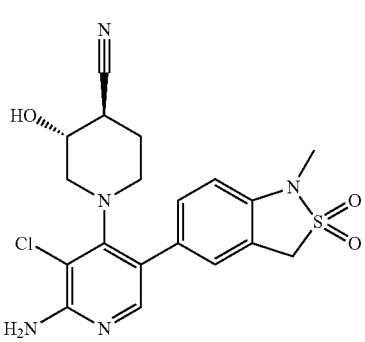 [SMILES: CN1c2ccc(-c3cnc(N)c(Cl)c3N3CC[C@H](C#N)[C@@H](O)C3)cc2CS1(=O)=O] | 0.014 | B | 1.357 (D) | (3R,4R)-2'-Amino-3'-chloro-3-hydroxy-5'-(1-methyl-2,2-dioxo-2,3-dihydro-1H-2I6-benzo[c]isothiazol-5-yl)-3,4,5,6-tetrahydro-2H-[1,4']bipyridinyl-4-carbonitrile | 1H NMR (500 MHz, DMSO-d6) ppm = 7.63 (s, 1H), 7.25-7.15 (m, 2H), 6.98 (d, J = 8.1, 1H), 6.14 (s, 2H), 5.60 (d, J = 5.6, 1H), 4.68 (s, 2H), 3.63-3.37 (m, 1H), 3.13-3.00 (m, 4H), 2.99-2.83 (m, 1H), 2.66-2.19 (m, 3H), 1.97-1.83 (m, 1H), 1.83-1.51 (m, 1H). |

TABLE 1-continued

| No | Chemical Structure | LS174T IC50 [μM] | Human CLint [μL/min/mg] | HPLC/MS Rt [min] (method) | Chemical Name | NMR data |
|---|---|---|---|---|---|---|
| 66 | 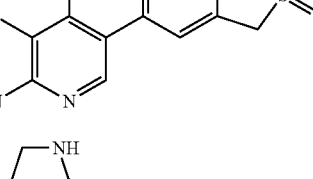 | 0.403 | B | 1.370 (D) | (3S,4S)-2'-Amino-3'-chloro-3-hydroxy-5'-(1-methyl-2,2-dioxo-2,3-dihydro-1H-2l6-benzo[c]isothiazol-5-yl)-3,4,5,6-tetrahydro-2H-[1,4']bipyridinyl-4-carbonitrile | 1H NMR (500 MHz, DMSO-d6) ppm = 7.63 (s, 1H), 7.25-7.16 (m, 2H), 6.98 (d, J = 8.1, 1H), 6.14 (s, 2H), 5.60 (d, J = 5.7, 1H), 4.68 (s, 2H), 3.64-3.42 (m, 1H), 3.12-3.01 (m, 4H), 2.97-2.86 (m, 1H), 2.62-2.21 (m, 3H), 1.94-1.83 (m, 1H), 1.79-1.49 (m, 1H). |
| 67 | 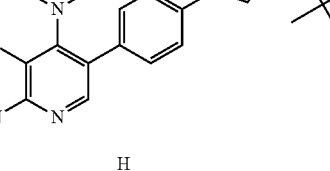 | 0.049 | B | 1.439 (D) | 8-(2-Amino-3-chloro-5-{4-[1-(2-hydroxy-2-methyl-propyl)-1H-pyrazol-4-yl]-phenyl}-pyridin-4-yl)-2,8-diaza-spiro[4.5]decan-1-one | 1H NMR (500 MHz, DMSO-d6) ppm = 8.11 (s, 1H), 7.90 (s, 1H), 7.64 (s, 1H), 7.63-7.58 (m, 2H), 7.46 (s, 1H), 7.27-7.21 (m, 2H), 6.07 (s, 2H), 4.71 (s, 1H), 4.04 (s, 2H), 3.10 (t, J = 6.8, 2H), 3.02-2.93 (m, 2H), 2.74-2.64 (m, 2H), 1.82 (t, J = 6.8, 2H), 1.75-1.65 (m, 2H), 1.26-1.17 (m, 2H), 1.10 (s, 6H). |
| 68 | 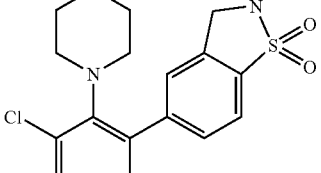 | 0.059 | A | 1.93 (A) | 8-[2-Amino-3-chloro-5-(2-ethyl-1,1-dioxo-2,3-dihydro-1H-1l6-benzo[d]isothiazol-5-yl)-pyridin-4-yl]-2,8-diaza-spiro[4.5]decan-1-one | 1H NMR (500 MHz, DMSO-d6) ppm = 7.85 (d, J = 8.0, 1H), 7.70 (s, 1H), 7.58-7.52 (m, 1H), 7.50 (s, 1H), 7.49-7.44 (m, 1H), 6.28 (s, 2H), 4.50 (s, 2H), 3.35-3.23 (m, 4H), 3.12 (t, J = 6.8, 2H), 3.04-2.93 (m, 2H), 1.86 (t, J = 6.8, 2H), 1.72-1.60 (m, 2H), 1.28 (t, J = 7.2, 3H), 1.25-1.18 (m, 2H). |
| 69 | 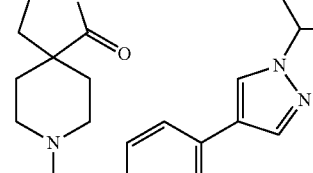 | 0.052 | C | 2.26 (B) | 8-{2-Amino-3-chloro-5-[4-(1-isopropyl-1H-pyrazol-4-yl)-phenyl]-pyridin-4-yl}-2,8-diaza-spiro[4.5]decan-1-one | 1H NMR (500 MHz, CDCl3) ppm = 7.82 (s, 1H), 7.75 (s, 1H), 7.72 (s, 1H), 7.52 (d, J = 8.3, 2H), 7.23 (d, J = 8.3, 2H), 6.42 (s, 1H), 4.93 (s, 2H), 4.53 (septuplet, J = 6.7, 1H), 3.26 (t, J = 6.9, 2H), 3.14-3.08 (m, 2H), 2.78-2.67 (m, 2H), 2.02-1.92 (m, 4H), 1.55 (d, J = 6.7, 6H), 1.33-1.28 (m, 2H). |
| 70 | 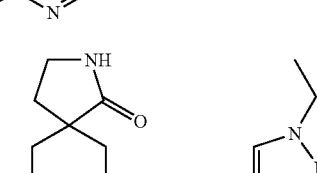 | 0.023 | E | 2.16 (B) | 8-{2-Amino-3-chloro-5-[4-(1-ethyl-1H-pyrazol-4-yl)-phenyl]-pyridin-4-yl}-2,8-diaza-spiro[4.5]decan-1-one | 1H NMR (500 MHz, DMSO-d6) ppm = 8.23 (s, 1H), 7.90 (s, 1H), 7.64 (s, 1H), 7.61 (d, J = 8.4, 2H), 7.51 (s, 1H), 7.23 (d, J = 8.4, 2H), 6.13 (s, 2H), 4.15 (q, J = 7.3, 2H), 3.10 (t, J = 6.8, 2H), 3.00-2.93 (m, 2H), 2.72-2.62 (m, 2H), 1.81 (t, J = 6.8, 2H), 1.74-1.65 (m, 2H), 1.41 (t, J = 7.3, 3H), 1.23-1.18 (m, 2H). |

TABLE 1-continued

| No | Chemical Structure | LS174T IC$_{50}$ [μM] | Human CLint [μL/min/mg] | HPLC/MS Rt [min] (method) | Chemical Name | NMR data |
|---|---|---|---|---|---|---|
| 71 | 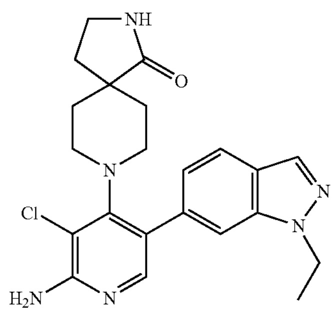 [SMILES: CCn1ncc2ccc(-c3cnc(N)c(Cl)c3N3CCC4(CCNC4=O)CC3)cc21] | 0.181 | B | 2.05 (B) | 8-[2-Amino-3-chloro-5-(1-ethyl-1H-indazol-6-yl)-pyridin-4-yl]-2,8-diaza-spiro[4.5]decan-1-one | 1H-NMR (500 MHz, DMSO) ppm = 8.06 (d, J = 0.9, 1H), 7.76 (d, J = 8.0, 1H), 7.73 (s, 1H), 7.54 (s, 1H), 7.49 (s, 1H), 7.03 (d, J = 8.0, 1H), 6.16 (s, 2H), 4.46 (q, J = 7.2, 2H), 3.07 (t, J = 6.8, 2H), 3.03-2.95 (m, 2H), 2.72-2.57 (m, 2H), 1.75 (t, J = 6.8, 2H), 1.72-1.61 (m, 2H), 1.42 (t, J = 7.2, 3H), 1.21-1.13 (m, 2H). |
| 72 | 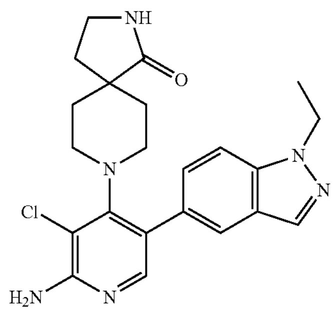 [SMILES: CCn1ncc2cc(-c3cnc(N)c(Cl)c3N3CCC4(CCNC4=O)CC3)ccc21] | 0.155 | D | 1.97 (B) | 8-[2-Amino-3-chloro-5-(1-ethyl-1H-indazol-5-yl)-pyridin-4-yl]-2,8-diaza-spiro[4.5]decan-1-one | 1H-NMR (500 MHz, MeOD) ppm = 8.02 (d, J = 1.0, 1H), 7.67 (s, 1H), 7.61 (s, 1H), 7.55 (d, J = 8.7, 1H), 7.30 (dd, J = 8.7, 1.6, 1H), 4.48 (q, J = 7.2, 2H), 3.24 (dd, J = 7.1, 6.4, 2H), 3.13 (dt, J = 12.5, 3.8, 2H), 2.80-2.64 (m, 2H), 1.95-1.81 (m, 2H), 1.92 (t, J = 7.1, 2H), 1.53 (t, J = 7.2, 3H), 1.31-1.23 (m, 2H). |
| 73 | | 0.054 | D | 2.13 (B) | 8-[2-Amino-3-chloro-5-(1-isopropyl-1H-indazol-6-yl)-pyridin-4-yl]-2,8-diaza-spiro[4.5]decan-1-one | 1H-NMR (500 MHz, CDCl3/MeOD, 1:1) ppm = 8.02 (d, J = 0.9, 1H), 7.77 (dd, J = 8.2, 0.9, 1H), 7.71 (s, 1H), 7.37 (d, J = 0.9, 1H), 7.04 (dd, J = 8.2, 0.9, 1H), 4.91 (p, J = 6.7, 1H), 3.24 (t, J = 6.9, 2H), 3.15 (dt, J = 13.2, 3.7, 2H), 2.72 (t, J = 10.5, 2H), 1.97-1.84 (m, 4H, spiro-4H), 1.61 (s, 3H), 1.60 (s, 3H), 1.33-1.25 (m, 2H). | nd = not determined

The invention also relates to the following compounds which can be made and tested according to the methods described above:

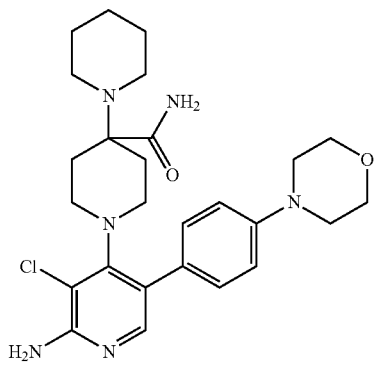

-continued

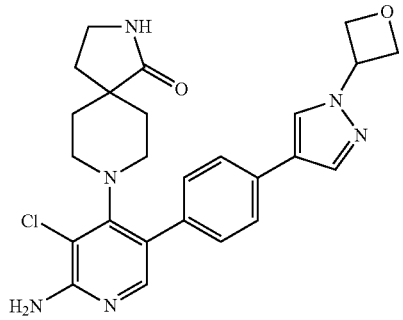

109
-continued
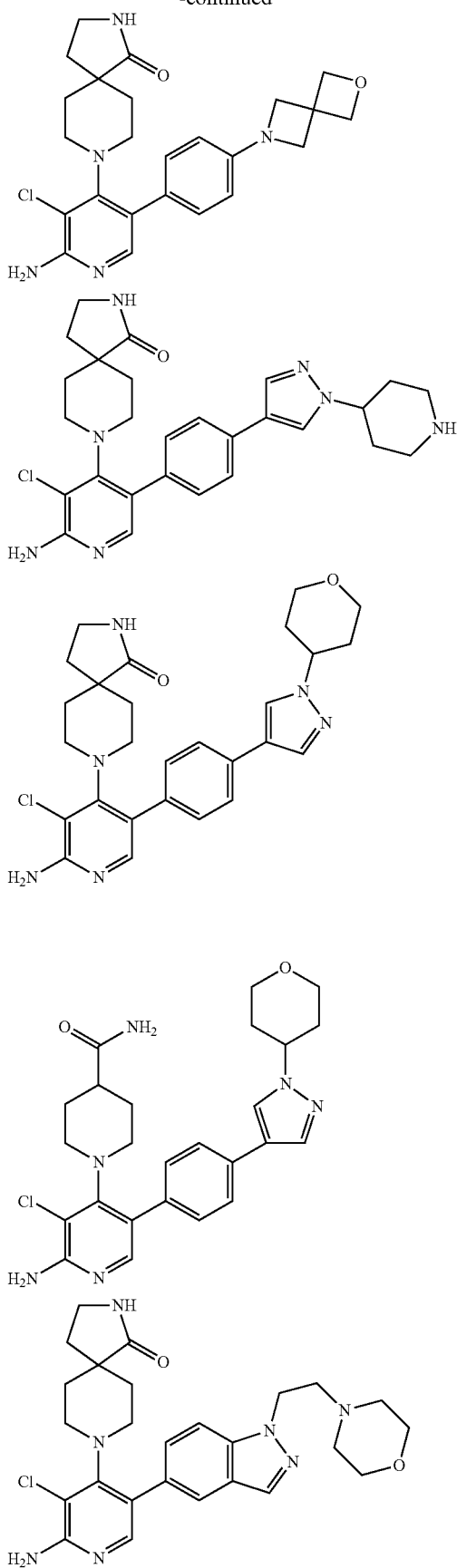
110
-continued
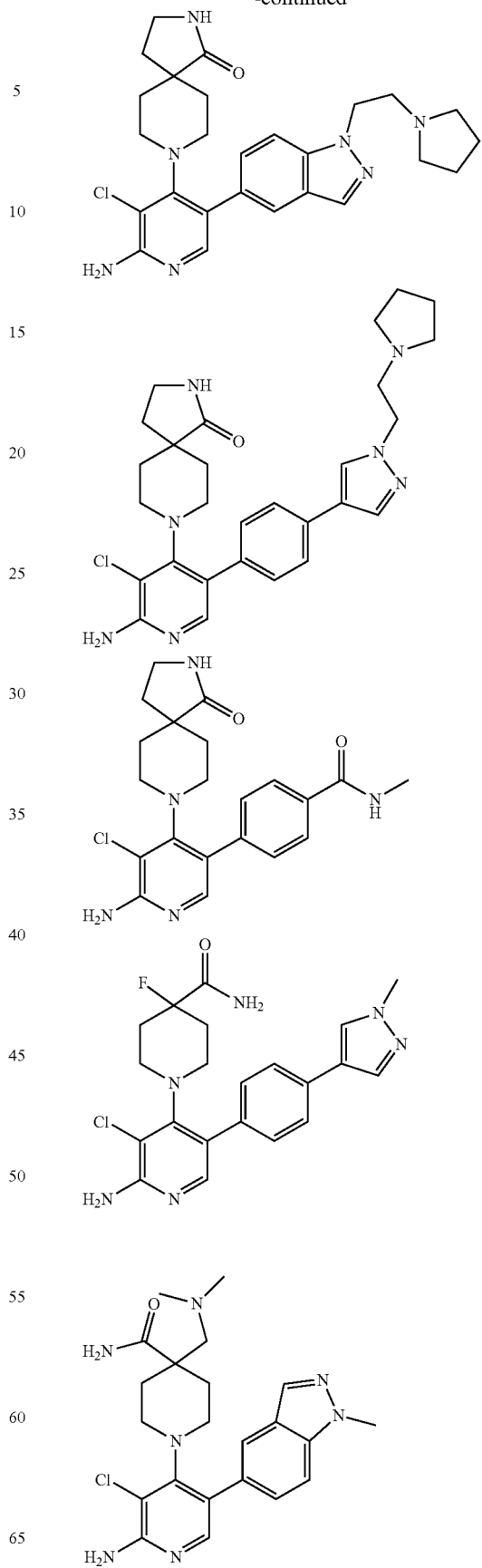

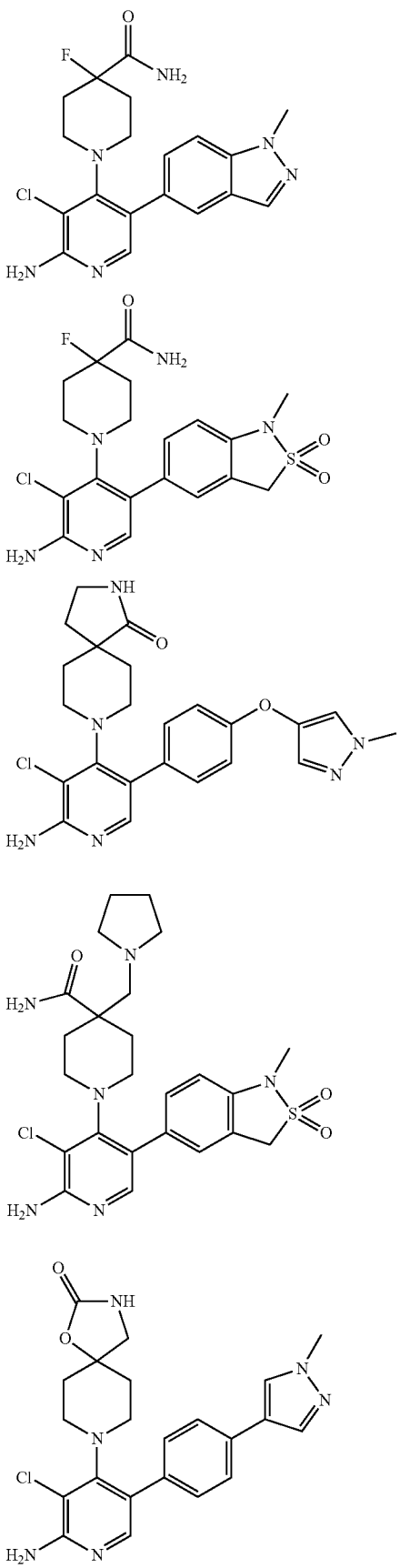

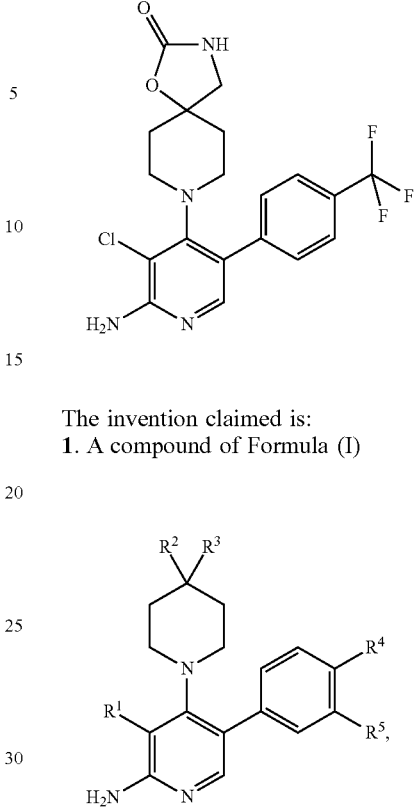

The invention claimed is:
1. A compound of Formula (I)

(I)

or its stereoisomers or tautomers, or pharmaceutically acceptable salts of each of the foregoing, including mixtures thereof in all ratios, wherein
$R^1$ is H, LA, Hal, CN, S(LA), or CA,
$R^2$ is H, NH$_2$, LA, NH(LA), Hal, or X-Cyc,
$R^3$ is LA, Hal, CN, CONH$_2$, or CONH(LA)
or
$R^2$ and $R^3$ together with the C atom they are attached to, form a 5 or 6 membered aliphatic heterocycle, having 1-3 heteroatoms, selected from O, S and N, which is substituted by 1 or 2 oxo groups, which heterocycle may further be monosubstituted by LA, and which heterocycle may form a condensed ring system with a phenyl or pyridyl group,
$R^4$ is H, LA, CONH(LA) or X-Cyc,
$R^5$ is H, or F,
or
$R^4$ and $R^5$ together with the atoms they are attached to, form a 5 or 6 membered heterocycle, having 1-3 heteroatoms, selected from O, S and N, which is, optionally, independently mono-, di- or trisubstituted by oxo, LA, NH$_2$, NH(LA), N(LA)$_2$, or HO(LA)-, or which is, optionally, monosubstituted by CA,
$R^6$ is H, LA, OH or F,
Cyc is a 5 or 6 membered monocyclic, aliphatic or aromatic homo- or heterocycle having 1-3 heteroatoms, selected from O, S and N, which may be mono- or di-substituted by oxo, LA, NH$_2$, NH(LA), N(LA)$_2$, or HO(LA)-, or monosubstituted by CA,
X is —CH$_2$—, —C$_2$H$_4$—, —NH—, —O—, or a bond,
LA is unbranched or branched alkyl, having 1, 2, 3, 4 or 5 carbon atoms, which may be saturated or partially unsaturated, wherein 1, 2 or 3H atoms may be replaced by Hal, and/or 1 CH₂ group may be replaced by —O—, —NH— or —SO₂—, and/or
1 CH group may be replaced by N,
CA is cycloalkyl having 3, 4, 5 or 6 carbon atoms, or cycloalkyl alkyl having 3, 4, 5 or 6 ring carbon atoms and 1 or 2 non-ring carbon atoms, and
Hal is F, Cl, Br or I.

2. The compound according to claim 1, or its stereoisomers or tautomers, or pharmaceutically acceptable salts of each of the foregoing, including mixtures thereof in all ratios, in which the residues not designated in greater detail have the meaning indicated for Formula (I), but in which
in Subformula 1
R² and R³ together with the piperidine ring they are attached to, form (2,8-diaza-spiro[4.5]decan-1-one)-8-yl, (2,8-diaza-spiro[4.5]decane-1,3-dione)-8-yl, (1-oxa-3,8-diaza-spiro[4.5]decan-2-one)-8-yl, (1,3,8-triaza-spiro[4.5]decane-2,4-dione)-8-yl, or (1,4,9-triaza-spiro[5.5]undecan-5-one)-9-yl, (4-oxo-1,3,8-triazaspiro[4.5]decan-8-yl,
R⁶ is H,
in Subformula 2
R² and R³ together with the C atom they are attached to, form 1,3-Dihydro-indol-2-one-3-yl or Aza-1,3-dihydro-indol-2-one-3-yl
R⁶ is H,
in Subformula 3
R⁴ is morpholin-4-yl, piperazin-1-yl, 1H-pyrazol-3-yl, pyridin-3-yl, or 1H-pyrazol-4-yl,
each of which may be unsubstituted, or monosubstituted by LA, OH, NH₂, HO(LA)- or NH₂(LA)-,
R⁵ is H,
in Subformula 4
R⁴ and R⁵ together with the phenyl ring they are attached to, form 1H-indazol-5-yl, 1H-indazol-6-yl, 2-oxo-2,3-dihydro-benzooxazol-5-yl, 2-oxo-2,3-dihydro-1H-indol-5-yl, 2-oxo-2,3-dihydro-1H-indol-6-yl, (3,4-dihydro-1H-quinolin-2-one)-6-yl, 1H-indol-6-yl, 2-oxo-2,3-dihydro-1H-indol-6-yl, (3,4-dihydro-1H-quinolin-2-one)-6-yl, 2,2-dioxo-2,3-dihydro-1H-2l6-benzo[c]isothiazol-5-yl, 2,2-dioxo-2,3-dihydro-1H-2l6-benzo[c]isothiazol-6-yl, 1,1-dioxo-2,3-dihydro-1H-1l6-benzo[b]thiophen-5-yl, or 1-dioxido-2,3-dihydrobenzo[d]isothiazol-6-yl,
each of which may be unsubstituted, or substituted by LA, OH, NH₂, HO(LA)- or NH₂(LA)-,
in Subformula 6
R¹ is Hal or C(Hal)₃,
in Subformula 7
R⁴ is morpholin-4-yl, 4-methyl-piperazin-1-yl, 1-methyl-1H-pyrazol-3-yl, 6-amino-pyridin-3-yl, 1-(2-hydroxyethyl)-1H-pyrazol-4-yl, or 1-methyl-1H-pyrazol-4-yl
R⁵ is H,
in Subformula 8
R⁴ and R⁵ together with the phenyl ring they are attached to, form 1-methyl-1H-indazol-5-yl, 1H-indazol-5-yl, 1-methyl-1H-indazol-6-yl, 1-ethyl-1H-indazol-5-yl, 1-ethyl-1H-indazol-6-yl, 1-isopropyl-1H-indazol-6-yl, 2-oxo-2,3-dihydro-benzooxazol-5-yl, (3H-benzooxazol-2-one)-5-yl, 1-methyl-2-oxo-2,3-dihydro-1H-indol-5-yl, 2-oxo-2,3-dihydro-1H-indol-5-yl, 1-methyl-2-oxo-2,3-dihydro-1H-indol-6-yl, (3,4-dihydro-1H-quinolin-2-one)-6-yl, 1H-indol-6-yl, 2-oxo-2,3-dihydro-1H-indol-6-yl, (1-methyl-3,4-dihydro-1H-quinolin-2-one)-6-yl, 3-amino-1H-indazol-6-yl, 1-methyl-2,2-dioxo-2,3-dihydro-1H-2l6-benzo[c]isothiazol-5-yl, 1-ethyl-2,2-dioxo-2,3-dihydro-1H-2l6-benzo[c]isothiazol-5-yl, 2,2-dioxo-2,3-dihydro-1H-2l6-benzo[c]isothiazol-6-yl, 1,1-dioxo-2,3-dihydro-1H-1l6-benzo[b]thiophen-5-yl, or 2-ethyl-1,1-dioxido-2,3-dihydrobenzo[d]isothiazol-6-yl,
in Subformula 9
R¹ is F, Cl or CF₃,
in Subformula 10
R² and R³ together with the piperidine ring they are attached to, form (2,8-diaza-spiro[4.5]decan-1-one)-8-yl, (1-oxa-3,8-diaza-spiro[4.5]decan-2-one)-8-yl, or (1,3,8-triaza-spiro[4.5]decane-2,4-dione)-8-yl,
R⁶ is H,
in Subformula 11
R¹ is F, Cl or CF₃,
R² and R³ together with the piperidine ring they are attached to, form (2,8-diaza-spiro[4.5]decan-1-one)-8-yl, (1-oxa-3,8-diaza-spiro[4.5]decan-2-one)-8-yl, or (1,3,8-triaza-spiro[4.5]decane-2,4-dione)-8-yl,
R⁶ is H,
in Subformula 12
R² is H,
R³ is CN, CONH₂,
R⁶ is H,
in Subformula 13
R² is H,
R³ is CN,
R⁶ is OH.

3. The compound according to claim 1, wherein the compound is selected from the group consisting of:
8-(2-Amino-3-chloro-5-phenyl-pyridin-4-yl)-2,8-diaza-spiro[4.5]decan-1-one,
8-{2-Amino-3-chloro-5-[4-(1-methyl-1H-pyrazol-4-yl)-phenyl]-pyridin-4-yl}-1,3,8-triaza-spiro[4.5]decane-2,4-dione,
8-[2-Amino-5-(3-amino-1H-indazol-6-yl)-3-chloro-pyridin-4-yl]-2,8-diaza-spiro[4.5]decan-1-one,
8-[2-Amino-3-chloro-5-(1-methyl-2,2-dioxo-2,3-dihydro-1H-2l6-benzo[c]isothiazol-5-yl)-pyridin-4-yl]-1-oxa-3,8-diaza-spiro[4.5]decan-2-one,
8-[2-Amino-5-(3-amino-1H-indazol-6-yl)-3-chloro-pyridin-4-yl]-1,3,8-triaza-spiro[4.5]decane-2,4-dione,
8-(2-Amino-3-chloro-5-{4-[1-(2-hydroxy-ethyl)-1H-pyrazol-4-yl]-phenyl}-pyridin-4-yl)-1,3,8-triaza-spiro[4.5]decane-2,4-dione,
6-(6-Amino-5-chloro-4-(1-oxo-2,8-diazaspiro[4.5]decan-8-yl)pyridin-3-yl)indolin-2-one,
8-[2-Amino-3-chloro-5-(1-methyl-1H-indazol-5-yl)-pyridin-4-yl]-1,3,8-triaza-spiro[4.5]decane-2,4-dione,
8-[2-Amino-3-chloro-5-(2-oxo-2,3-dihydro-benzooxazol-5-yl)-pyridin-4-yl]-1-oxa-3,8-diaza-spiro[4.5]decan-2-one,
8-{2-Amino-3-chloro-5-[4-(1-methyl-1H-pyrazol-4-yl)-phenyl]-pyridin-4-yl}-1-oxa-3,8-diaza-spiro[4.5]decan-2-one,
1'-(2-Amino-3-chloro-5-(4-(1-methyl-1H-pyrazol-4-yl)phenyl)pyridin-4-yl)spiro[indoline-3,4'-piperidin]-2-one,
8-[2-Amino-5-(3-amino-1H-indazol-6-yl)-3-chloro-pyridin-4-yl]-2,8-diaza-spiro[4.5]decane-1,3-dione,
8-[2-Amino-3-chloro-5-(2-oxo-1,2,3,4-tetrahydro-quinolin-6-yl)-pyridin-4-yl]-2,8-diaza-spiro[4.5]decane-1,3-dione,
6-[6-Amino-5-chloro-4-(1-oxo-2,8-diaza-spiro[4.5]decan-8-yl)-pyridin-3-yl]-1-methyl-3,4-dihydro-1H-quinolin-2-one, 8-[2-Amino-3-chloro-5-(1-methyl-2-oxo-2,3-dihydro-1H-indol-5-yl)-pyridin-4-yl]-2,8-diaza-spiro[4.5]decan-1-one, 8-{2-Amino-3-chloro-5-[4-(1-methyl-1H-pyrazol-4-yl)-phenyl]-pyridin-4-yl}-2,8-diaza-spiro[4.5]decan-1-one, 8-[2-Amino-3-chloro-5-(1-methyl-1H-indazol-5-yl)-pyridin-4-yl]-2,8-diaza-spiro[4.5]decane-1,3-dione, 8-[2-Amino-3-chloro-5-(4-morpholin-4-yl-phenyl)-pyridin-4-yl]-2,8-diaza-spiro[4.5]decan-1-one, 6-[6-Amino-5-chloro-4-(1-oxo-2,8-diaza-spiro[4.5]decan-8-yl)-pyridin-3-yl]-3,4-dihydro-1H-quinolin-2-one, 8-[2-Amino-3-chloro-5-(1-methyl-1H-indazol-6-yl)-pyridin-4-yl]-1-oxa-3,8-diaza-Spiro[4.5]decan-2-one, 8-[2-Amino-3-chloro-5-(1-methyl-1H-indazol-5-yl)-pyridin-4-yl]-1-oxa-3,8-diaza-spiro[4.5]decan-2-one, 8-{2-Amino-3-chloro-5-[4-(1-methyl-1H-pyrazol-3-yl)-phenyl]-pyridin-4-yl}-2,8-diaza-spiro[4.5]decan-1-one, 8-[2-Amino-3-chloro-5-(1-methyl-1H-indazol-6-yl)-pyridin-4-yl]-2,8-diaza-spiro[4.5]decan-1-one, 8-[2-Amino-3-chloro-5-(1H-indol-6-yl)-pyridin-4-yl]-2,8-diaza-spiro[4.5]decan-1-one, 8-[2-Amino-3-chloro-5-(1-methyl-1H-indazol-5-yl)-pyridin-4-yl]-2,8-diaza-spiro[4.5]decan-1-one, 8-(2-Amino-3-chloro-5-(1-methyl-2,2-dioxido-1,3-dihydrobenzo[c]isothiazol-5-yl)pyridin-4-yl)-2,8-diazaspiro[4.5]decan-1-one, 1-(2-Amino-3-chloro-5-(4-morpholinophenyl)pyridin-4-yl)piperidine-4-carbonitrile, 8-{2-Amino-5-[4-(6-amino-pyridin-3-yl)-phenyl]-3-chloro-pyridin-4-yl}-2,8-diaza-spiro[4.5]decan-1-one, 8-[2-Amino-3-chloro-5-(1H-indol-6-yl)-pyridin-4-yl]-1-oxa-3,8-diaza-spiro[4.5]decan-2-one, 1-(2-Amino-3-chloro-5-(4-(4-methylpiperazin-1-yl)phenyl)pyridin-4-yl)piperidine-4-carbonitrile, 1'-(2-Amino-3-chloro-5-(1-methyl-1H-indazol-5-yl)pyridin-4-yl)spiro[indoline-3,4'-piperidin]-2-one, 5-[6-Amino-5-chloro-4-(1-oxo-2,8-diaza-spiro[4.5]dec-8-yl)-pyridin-3-yl]-3H-benzooxazol-2-one, 8-[2-Amino-3-chloro-5-(2-oxo-2,3-dihydro-1H-indol-5-yl)-pyridin-4-yl]-2,8-diaza-spiro[4.5]decan-1-one, 8-(2-Amino-3-chloro-5-{4-[1-(2-hydroxy-ethyl)-1H-pyrazol-4-yl]-phenyl}-pyridin-4-yl)-1-oxa-3,8-diazaspiro[4.5]decan-2-one, 8-[2-Amino-3-chloro-5-(1H-indazol-5-yl)-pyridin-4-yl]-2,8-diaza-spiro[4.5]decan-1-one, 8-[2-Amino-3-chloro-5-(1-methyl-2-oxo-2,3-dihydro-1H-indol-5-yl)-pyridin-4-yl]-1-oxa-3,8-diaza-spiro[4.5]decan-2-one, 8-[2-Amino-5-(3-amino-1H-indazol-6-yl)-3-chloro-pyridin-4-yl]-1-oxa-3,8-diaza-spiro[4.5]decan-2-one, 8-{2-Amino-3-chloro-5-[4-(1-methyl-1H-pyrazol-4-yl)-phenyl]-pyridin-4-yl}-2,8-diaza-spiro[4.5]decane-1,3-dione, 8-[2-Amino-5-(1-methyl-1H-indazol-5-yl)-3-trifluoromethyl-pyridin-4-yl]-2,8-diaza-spiro[4.5]decan-1-one, 9-{2-Amino-3-chloro-5-[4-(1-methyl-1H-pyrazol-4-yl)-phenyl]-pyridin-4-yl}-1,4,9-triaza-spiro[5.5]undecan-5-one, 8-{2-Amino-5-[4-(1-methyl-1H-pyrazol-4-yl)-phenyl]-3-trifluoromethyl-pyridin-4-yl}-1-oxa-3,8-diaza-spiro[4.5]decan-2-one, 8-[2-Amino-5-(1-methyl-2,2-dioxo-2,3-dihydro-1H-2l6-benzo[c]isothiazol-5-yl)-3-trifluoromethyl-pyridin-4-yl]-1-oxa-3,8-diaza-spiro[4.5]decan-2-one, 8-{2-Amino-5-[4-(1-methyl-1H-pyrazol-4-yl)-phenyl]-3-trifluoromethyl-pyridin-4-yl}-2,8-diaza-spiro[4.5]decan-1-one, 8-[2-Amino-5-(3-amino-1H-indazol-6-yl)-3-trifluoromethyl-pyridin-4-yl]-2,8-diaza-spiro[4.5]decan-1-one, 9-(2-Amino-3-chloro-5-{4-[1-(2-hydroxy-ethyl)-1H-pyrazol-4-yl]-phenyl}-pyridin-4-yl)-1,4,9-triaza-spiro[5.5]undecan-5-one, 9-[2-Amino-3-chloro-5-(1-methyl-2,2-dioxo-2,3-dihydro-1H-2l6-benzo[c]isothiazol-5-yl)-pyridin-4-yl]-1,4,9-triaza-spiro[5.5]undecan-5-one, 2'-Amino-5'-(1-methyl-1H-indazol-5-yl)-3'-trifluoromethyl-3,4,5,6-tetrahydro-2H-[1,4']bipyridinyl-4-carboxylic acid amide, 2'-Amino-5'-[4-(1-methyl-1H-pyrazol-4-yl)-phenyl]-3'-trifluoromethyl-3,4,5,6-tetrahydro-2H-[1,4']bipyridinyl-4-carboxylic acid amide, 8-[2-Amino-5-(1-methyl-1H-indazol-5-yl)-3-trifluoromethyl-pyridin-4-yl]-2,8-diaza-spiro[4.5]decane-1,3-dione, 8-{2-Amino-5-[4-(1-methyl-1H-pyrazol-4-yl)-phenyl]-3-trifluoromethyl-pyridin-4-yl}-2,8-diaza-spiro[4.5]decane-1,3-dione, 8-[2-Amino-3-fluoro-5-(1-methyl-2,2-dioxo-2,3-dihydro-1H-2l6-benzo[c]isothiazol-5-yl)-pyridin-4-yl]-1-oxa-3,8-diaza-spiro[4.5]decan-2-one, 8-{2-Amino-5-[4-(1-isopropyl-1H-pyrazol-4-yl)-phenyl]-3-trifluoromethyl-pyridin-4-yl}-1-oxa-3,8-diaza-spiro[4.5]decan-2-one, rac (3R,4R)-2'-Amino-3'-chloro-3-hydroxy-5'-(1-methyl-2,2-dioxo-2,3-dihydro-1H-2l6-benzo[c]isothiazol-5-yl)-3,4,5,6-tetrahydro-2H-[1,4']bipyridinyl-4-carbonitrile, 8-(2-Amino-3-chloro-5-{4-[1-(2-methanesulfonyl-ethyl)-1H-pyrazol-4-yl]-phenyl}-pyridin-4-yl)-2,8-diazaspiro[4.5]decan-1-one, 8-[2-Amino-3-fluoro-5-(1-methyl-2,2-dioxo-2,3-dihydro-1H-2l6-benzo[c]isothiazol-5-yl)-pyridin-4-yl]-2,8-diaza-spiro[4.5]decan-1-one, 8-[2-Amino-3-chloro-5-(1-ethyl-2,2-dioxo-2,3-dihydro-1H-2l6-benzo[c]isothiazol-5-yl)-pyridin-4-yl]-2,8-diaza-spiro[4.5]decan-1-one, 8-[2-Amino-5-(1-methyl-2-oxo-2,3-dihydro-1H-indol-6-yl)-3-trifluoromethyl-pyridin-4-yl]-2,8-diaza-spiro[4.5]decan-1-one, 8-[2-Amino-5-(1-methyl-2-oxo-2,3-dihydro-1H-indol-5-yl)-3-trifluoromethyl-pyridin-4-yl]-2,8-diaza-spiro[4.5]decan-1-one, 8-[2-Amino-5-(1-methyl-2,2-dioxo-2,3-dihydro-1H-2l6-benzo[c]isothiazol-5-yl)-3-trifluoromethyl-pyridin-4-yl]-2,8-diaza-spiro[4.5]decan-1-one, 8-{2-Amino-3-chloro-5-[4-(1-isopropyl-1H-pyrazol-4-yl)-phenyl]-pyridin-4-yl}-1-oxa-3,8-diaza-spiro[4.5]decan-2-one, rac (3R,4R)-2'-Amino-3'-chloro-3-hydroxy-5'-[4-(1-methyl-1H-pyrazol-4-yl)-phenyl]-3,4,5,6-tetrahydro-2H-[1,4']bipyridinyl-4-carbonitrile, 8-[2-Amino-3-chloro-5-(1-ethyl-2,2-dioxo-2,3-dihydro-1H-2l6-benzo[c]isothiazol-5-yl)-pyridin-4-yl]-2,8-diaza-spiro[4.5]decan-1-one, 8-[2-Amino-3-chloro-5-(1,1-dioxo-2,3-dihydro-1H-1l6-benzo[b]thiophen-5-yl)-pyridin-4-yl]-2,8-diaza-spiro[4.5]decan-1-one, 8-{2-Amino-3-fluoro-5-[4-(1-methyl-1H-pyrazol-4-yl)-phenyl]-pyridin-4-yl}-1-oxa-3,8-diaza-spiro[4.5]decan-2-one, 8-[2-Amino-3-fluoro-5-(1-methyl-1H-indazol-5-yl)-pyridin-4-yl]-2,8-diaza-spiro[4.5]decan-1-one,
(3R,4R)-2'-Amino-3'-chloro-3-hydroxy-5'-(1-methyl-2,2-dioxo-2,3-dihydro-1H-2l6-benzo[c]isothiazol-5-yl)-3,4,5,6-tetrahydro-2H-[1,4']bipyridinyl-4-carbonitrile,
(3S,4S)-2'-Amino-3'-chloro-3-hydroxy-5'-(1-methyl-2,2-dioxo-2,3-dihydro-1H-2l6-benzo[c]isothiazol-5-yl)-3,4,5,6-tetrahydro-2H-[1,4']bipyridinyl-4-carbonitrile,
8-(2-Amino-3-chloro-5-{4-[1-(2-hydroxy-2-methyl-propyl)-1H-pyrazol-4-yl]-phenyl}-pyridin-4-yl)-2,8-diaza-spiro[4.5]decan-1-one,
8-{2-Amino-3-chloro-5-[4-(1-isopropyl-1H-pyrazol-4-yl)-phenyl]-pyridin-4-yl}-2,8-diaza-spiro[4.5]decan-1-one,
8-{2-Amino-3-chloro-5-[4-(1-ethyl-1H-pyrazol-4-yl)-phenyl]-pyridin-4-yl}-2,8-diaza-spiro[4.5]decan-1-one,
8-[2-Amino-3-chloro-5-(1-ethyl-1H-indazol-6-yl)-pyridin-4-yl]-2,8-diaza-spiro[4.5]decan-1-one,
8-[2-Amino-3-chloro-5-(1-ethyl-1H-indazol-5-yl)-pyridin-4-yl]-2,8-diaza-spiro[4.5]decan-1-one,
and
8-[2-Amino-3-chloro-5-(1-isopropyl-1H-indazol-6-yl)-pyridin-4-yl]-2,8-diaza-spiro[4.5]decan-1-one,
and stereoisomers, tautomers, and pharmaceutically acceptable salts of each of the foregoing, including mixtures thereof in all ratios.

4. A pharmaceutical composition comprising a compound according to claim 1, or its stereoisomers or tautomers, or pharmaceutically acceptable salts of each of the foregoing, including mixtures thereof in all ratios, as active ingredient, together with a pharmaceutically acceptable carrier.

5. A method for the treatment of colon cancer comprising administering a compound according to claim 1, or its stereoisomers or tautomers, or pharmaceutically acceptable salts thereof, including mixtures thereof in all ratios.

6. A kit consisting of separate packs of
a) an effective amount of a compound according to claim 1, or its stereoisomers or tautomers, or pharmaceutically acceptable salts of each of the foregoing, including mixtures thereof in all ratios, and
b) an effective amount of a further medicament active ingredient.

7. A compound of Formula (I)

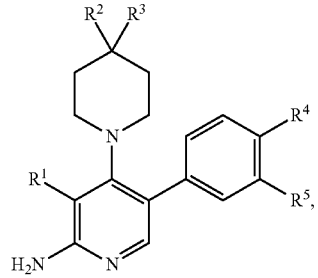

or a stereoisomer, tautomer or pharmaceutically acceptable salt thereof, including mixtures thereof in all ratios, wherein $R^1$ is H, LA, Hal, CN, S(LA), or CA, $R^2$ and $R^3$ together with the C atom they are attached to, form a 5 or 6 membered aliphatic heterocycle, having 1-3 heteroatoms, selected from O, S and N, which is substituted by 1 or 2 oxo groups, which heterocycle may further be monosubstituted by LA, and which heterocycle may form a condensed ring system with a phenyl or pyridyl group, $R^4$ and $R^5$ together with the atoms they are attached to, form a 5 or 6 membered heterocycle, having 1-3 heteroatoms, selected from O, S and N, which is, optionally, independently mono-, di- or trisubstituted by oxo, LA, $NH_2$, NH(LA), $N(LA)_2$, or HO(LA)-, or which is, optionally, monosubsituted by CA, $R^6$ is H, LA, OH or F, X is —$CH_2$—, —$C_2H_4$—, —NH—, —O—, or a bond, LA is unbranched or branched alkyl, having 1, 2, 3, 4 or 5 carbon atoms, which may be saturated or partially unsaturated, wherein 1, 2 or 3 H atoms may be replaced by Hal, and/or
1 $CH_2$ group may be replaced by —O—, —NH— or —$SO_2$—, and/or
1 CH group may be replaced by N, CA is cycloalkyl having 3, 4, 5 or 6 carbon atoms, or cycloalkyl alkyl having 3, 4, 5 or 6 ring carbon atoms and 1 or 2 non-ring carbon atoms, and Hal is F, Cl, Br or I.

* * * * *